US011783914B2

(12) United States Patent
Apte et al.

(10) Patent No.: US 11,783,914 B2
(45) Date of Patent: *Oct. 10, 2023

(54) METHOD AND SYSTEM FOR PANEL CHARACTERIZATIONS

(71) Applicant: PSOMAGEN, INC., Rockville, MD (US)

(72) Inventors: Zachary Apte, San Francisco, CA (US); Jessica Richman, San Francisco, CA (US); Daniel Almonacid, San Francisco, CA (US); Laurens Kraal, San Francisco, CA (US); Francisco Ossandon, San Francisco, CA (US); Juan Pablo Cardenas, San Francisco, CA (US); Elisabeth Bik, San Francisco, CA (US); Audrey Goddard, San Francisco, CA (US)

(73) Assignee: PSOMAGEN, INC., Rockville, MD (US)

( * ) Notice: Subject to any disclaimer, the term of this patent is extended or adjusted under 35 U.S.C. 154(b) by 394 days.

This patent is subject to a terminal disclaimer.

(21) Appl. No.: 15/707,907

(22) Filed: Sep. 18, 2017

(65) Prior Publication Data

US 2018/0137239 A1  May 17, 2018

Related U.S. Application Data

(63) Continuation-in-part of application No. 15/606,743, filed on May 26, 2017, now Pat. No. 10,803,991, which is a continuation-in-part of application No. 14/919,614, filed on Oct. 21, 2015, now Pat. No. 9,703,929.

(60) Provisional application No. 62/525,379, filed on Jun. 27, 2017, provisional application No. 62/520,058, filed on Jun. 15, 2017, provisional application No. 62/395,939, filed on Sep. 16, 2016, provisional application No. 62/206,654, filed on Aug. 18, 2015, provisional application No. 62/147,362, filed on Apr. 14, 2015, provisional application No. 62/147,376, filed on Apr. 14, 2015, provisional application No. 62/147,212, filed on Apr. 14, 2015, provisional application No. 62/146,855, filed on Apr. 13, 2015, provisional application No. 62/092,999, filed on Dec. 17, 2014, provisional application No. 62/087,551, filed on Dec. 4, 2014, provisional application No. 62/066,369, filed on Oct. 21, 2014.

(51) Int. Cl.
| | | |
|---|---|---|
| G01N 33/48 | (2006.01) |
| G01N 33/50 | (2006.01) |
| G16B 30/10 | (2019.01) |
| G16H 20/60 | (2018.01) |
| G16B 30/00 | (2019.01) |
| G16B 40/00 | (2019.01) |
| G16H 10/40 | (2018.01) |
| G16H 50/20 | (2018.01) |
| G16B 20/00 | (2019.01) |
| G16B 40/20 | (2019.01) |

(52) U.S. Cl.
CPC ............. *G16B 30/10* (2019.02); *G16B 20/00* (2019.02); *G16B 30/00* (2019.02); *G16B 40/00* (2019.02); *G16B 40/20* (2019.02); *G16H 10/40* (2018.01); *G16H 20/60* (2018.01); *G16H 50/20* (2018.01); *Y02A 90/10* (2018.01)

(58) Field of Classification Search
CPC ........ G16B 30/00; G16B 30/10; G16B 40/00; G16B 20/00; G16B 40/20; G16H 10/40; G16H 50/20; G16H 20/60
See application file for complete search history.

(56) References Cited

U.S. PATENT DOCUMENTS

| | | | |
|---|---|---|---|
| 107,557 | A | 9/1870 | Smith et al. |
| 521,843 | A | 6/1894 | Baker |
| 6,033,864 | A | 3/2000 | Braun et al. |

(Continued)

FOREIGN PATENT DOCUMENTS

| | | |
|---|---|---|
| CN | 105407728 | 3/2015 |
| EP | 2631240 | 8/2013 |

(Continued)

OTHER PUBLICATIONS

Slatko et al. "First Generation" Automated NDA Sequencing Technology Current Protocols in Molecular Biology pp. 7.2.1-7.2.28 (Year: 2011).*

(Continued)

*Primary Examiner* — Russell S Negin
*Assistant Examiner* — Steven W. Bailey
(74) *Attorney, Agent, or Firm* — LEX IP MEISTER, PLLC

(57) ABSTRACT

Embodiments of a system and method for characterizing a panel of conditions associated with a set of taxa related to microorganisms can include a taxonomic database including reference microbiome features for the set of taxa associated with the panel of conditions; a handling operable to collect a container including biological material from a user, the handling system comprising a sequencer system operable to determine a microorganism sequence dataset; and a panel characterization system operable to: determine user microbiome features for the set of taxa for the user based on the microorganism sequence dataset, generate a comparison between the user microbiome features and the reference microbiome features, and determine a panel characterization for the panel of conditions for the user based on the comparison; and a treatment system operable to promote a therapy for a condition of the panel of conditions based on the panel characterization.

9 Claims, 18 Drawing Sheets

Specification includes a Sequence Listing.

(56) References Cited

U.S. PATENT DOCUMENTS

| | | | |
|---|---|---|---|
| 6,309,643 | B1 | 10/2001 | Braun et al. |
| 6,632,641 | B1 | 10/2003 | Brennan et al. |
| 6,861,053 | B1 | 3/2005 | Lin et al. |
| 7,048,906 | B2 | 5/2006 | Lin et al. |
| 7,176,002 | B2 | 2/2007 | Lao et al. |
| 8,478,544 | B2 | 7/2013 | Colwell et al. |
| 8,598,203 | B2 | 12/2013 | Tarcic et al. |
| 8,883,264 | B2 | 11/2014 | Yang et al. |
| 9,028,841 | B2 | 5/2015 | Henn et al. |
| 9,149,473 | B2 | 10/2015 | Ecker et al. |
| 9,289,418 | B2 | 3/2016 | Pimentel et al. |
| 9,433,651 | B2 | 9/2016 | Jones et al. |
| 9,447,195 | B2 | 9/2016 | Cordova et al. |
| 9,506,109 | B2 | 11/2016 | Savelkoul et al. |
| 9,663,831 | B2 | 5/2017 | Apte et al. |
| 9,700,586 | B2 | 7/2017 | Bicalho et al. |
| 9,703,929 | B2 * | 7/2017 | Apte ............ C12Q 1/689 |
| 9,707,207 | B2 | 7/2017 | Finegold |
| 9,710,606 | B2 | 7/2017 | Apte et al. |
| 2002/0012926 | A1 | 1/2002 | Quake et al. |
| 2003/0190314 | A1 | 10/2003 | Campbell et al. |
| 2005/0196785 | A1 | 9/2005 | Quake et al. |
| 2006/0073501 | A1 | 4/2006 | Van Den Boom et al. |
| 2006/0089310 | A1 | 4/2006 | Goldstein et al. |
| 2007/0134652 | A1 | 6/2007 | Slepnev et al. |
| 2007/0259337 | A1 | 11/2007 | Hully et al. |
| 2008/0131556 | A1 | 6/2008 | De Simone et al. |
| 2010/0035232 | A1 | 2/2010 | Ecker et al. |
| 2010/0129816 | A1 | 5/2010 | Savelkoul et al. |
| 2010/0172874 | A1 | 7/2010 | Turnbaugh et al. |
| 2010/0331641 | A1 | 12/2010 | Bangera et al. |
| 2011/0027219 | A1 | 2/2011 | Tarcic et al. |
| 2011/0177976 | A1 | 7/2011 | Gordon et al. |
| 2012/0045771 | A1 | 2/2012 | Beier et al. |
| 2012/0129794 | A1 | 5/2012 | Dowd et al. |
| 2012/0149584 | A1 | 6/2012 | Olle et al. |
| 2012/0189621 | A1 | 7/2012 | Dean et al. |
| 2012/0252775 | A1 | 10/2012 | Finegold |
| 2013/0017999 | A1 | 1/2013 | Fremont et al. |
| 2013/0045874 | A1 * | 2/2013 | Ehrlich ............ C12Q 1/6883 435/6.12 |
| 2013/0108598 | A1 | 5/2013 | Oresic et al. |
| 2013/0121968 | A1 | 5/2013 | Quay |
| 2013/0184302 | A1 | 7/2013 | Bortey et al. |
| 2014/0093478 | A1 | 4/2014 | Turnbaugh et al. |
| 2014/0136120 | A1 | 5/2014 | Colwell et al. |
| 2014/0179726 | A1 | 6/2014 | Bajaj et al. |
| 2014/0199281 | A1 | 7/2014 | Henn et al. |
| 2014/0242080 | A1 | 8/2014 | Jaeger et al. |
| 2014/0315929 | A1 | 10/2014 | Chiosis |
| 2014/0341853 | A1 | 11/2014 | Hovanky |
| 2014/0363399 | A1 | 12/2014 | Jones et al. |
| 2014/0377270 | A1 | 12/2014 | Moore et al. |
| 2015/0050245 | A1 | 2/2015 | Herman et al. |
| 2015/0056206 | A1 | 2/2015 | Zhou |
| 2015/0211055 | A1 | 7/2015 | Apte et al. |
| 2015/0211078 | A1 | 7/2015 | Apte et al. |
| 2015/0213193 | A1 | 7/2015 | Apte et al. |
| 2015/0259728 | A1 | 9/2015 | Cutliffe et al. |
| 2015/0374761 | A1 | 12/2015 | Sadowsky et al. |
| 2016/0017058 | A1 | 1/2016 | Kim et al. |
| 2016/0032363 | A1 | 2/2016 | Stintzi et al. |
| 2016/0040216 | A1 | 2/2016 | Akins et al. |
| 2016/0110515 | A1 | 4/2016 | Apte et al. |
| 2016/0138089 | A1 | 5/2016 | Harris et al. |
| 2016/0223553 | A1 | 8/2016 | Sears et al. |
| 2016/0228003 | A1 | 8/2016 | Apte et al. |
| 2016/0290132 | A1 | 10/2016 | Knight et al. |
| 2017/0039347 | A1 | 2/2017 | Apte et al. |
| 2017/0081707 | A1 | 3/2017 | Dillon et al. |
| 2017/0235902 | A1 | 8/2017 | Almonacid et al. |
| 2017/0262608 | A1 | 9/2017 | Apte et al. |
| 2017/0268045 | A1 | 9/2017 | Apte et al. |
| 2017/0268046 | A1 | 9/2017 | Apte et al. |
| 2017/0270268 | A1 | 9/2017 | Apte et al. |
| 2017/0270269 | A1 | 9/2017 | Apte et al. |
| 2017/0270270 | A1 | 9/2017 | Apte et al. |
| 2017/0270271 | A1 | 9/2017 | Apte et al. |
| 2017/0270272 | A1 | 9/2017 | Apte et al. |
| 2017/0286619 | A1 | 10/2017 | Apte et al. |
| 2017/0286620 | A1 | 10/2017 | Apte et al. |
| 2017/0327864 | A1 | 11/2017 | Apte et al. |
| 2017/0344719 | A1 | 11/2017 | Apte et al. |
| 2018/0070827 | A1 | 3/2018 | Apte et al. |
| 2019/0085396 | A1 | 3/2019 | Apte et al. |

FOREIGN PATENT DOCUMENTS

| | | |
|---|---|---|
| EP | 2994756 | 3/2016 |
| JP | 2016-525355 | 8/2016 |
| WO | 39234 | 5/2003 |
| WO | 113066 | 9/2011 |
| WO | 50513 | 4/2012 |
| WO | 121298 | 8/2014 |
| WO | 138999 | 9/2014 |
| WO | 144092 | 9/2014 |
| WO | 145958 | 9/2014 |
| WO | 2015/013214 | 1/2015 |
| WO | 13214 | 1/2015 |
| WO | 2015/066625 | 5/2015 |
| WO | 85326 | 6/2015 |
| WO | 95241 | 6/2015 |
| WO | 103165 | 7/2015 |
| WO | 112352 | 7/2015 |
| WO | 2015/170979 | 11/2015 |
| WO | 170979 | 11/2015 |
| WO | 2015/095241 A4 | 12/2015 |
| WO | 2016/065075 A1 | 4/2016 |
| WO | 138337 | 9/2016 |
| WO | 172643 | 10/2016 |
| WO | 2016168352 | 10/2016 |
| WO | 44902 | 3/2017 |

OTHER PUBLICATIONS

Morgan et al. Meta'omic Analytic Techniques for Studying the Intestinal Microbiome Gastroenterology vol. 146, pp. 1437-1448 (Year: 2014).*

Li et al. An integrated catalog of reference genes in the human gut microbiome Nature Biotechnology vol. 32, pp. 834-841 (Year: 2014).*

Preidis et al. Targeting the Human Microbiome With Antibiotics, Probiotics, and Prebiotics: Gastroenterology Enters the Metagenomics Era. Gastroenterology vol. 136 pp. 2015-2031 (Year: 2009).*

"K03100: IepB: signal peptidase I," KEGG, Aug. 7, 2012 (Jul. 8, 2012), p. 1 of 1. Retrieved from the Internet: on Jun. 12, 2016 (Jun. 12, 2016).

"KEGG: Aminoacyl-tRNA biosynthesis—Reference pathway," Jul. 20, 2013 (Jul. 20, 2013). Retrieved from the internet: <http://web:archive.org/web/20130720015616/http:www.genome.jp/kegg-bin/show_pathway?map=map00970&show_description=show. on Jun. 20, 2016 (20.06.

Avila, Maria et al., The Oral Microbiota: Living with a Permanent Guest, DNA and Cell Biology, Nov. 8, 2009, vol. 28, No. 8.

Carroll et al. "Alterations in composition and diversity of the intestinal microbiota in patients with diarrhea-predominant irritable bowel syndrome," Feb. 20, 2012 (Feb. 29, 2012), vol. 24, pp. 1-19 [Original pp. 5215-5230] entire document.

Cho et al. "The Human Microbiome: at the Interface of Health and Disease," Nature Reviews Genetics, Apr. 1, 2012 (Apr. 1, 2012), vol. 13, pp. 260-270.

Dewhirst, Floyd et al., The Human Oral Microbiome, Journal of Bacteriology, Oct. 2010, vol. 192, No. 19, pp. 5002-5017.

Evans, Morgan, Prosthetic valve endocarditis due to Neisseria elongata subsp. elongata in a patient with Klinefelter's syndrome, Journal of Medical Microbiology, Jun. 1, 2007, vol. 56, No. 6, pp. 860-862.

(56) References Cited

OTHER PUBLICATIONS

Greenblum et al. "Metagenomic Systems Biology of the Human Gut Microbiome Reveals Topological Shifts Associated with Obesity and Inflammatory Bowel Disease," Proceeding of the National Academy of Sciences, Dec. 19, 2011 (Dec. 19, 2011), vol. 109, p. 594.
Kanehisa et al. KEGG: Kyoto encyclopedia of genes and genomes, Nucleic Acids Research, Jan. 1, 2000 (Jan. 1, 2000), vol. 28, No. 1, pp. 27-30.
Mak et al. "MetaboLyzer: A Novel Statistical Workflow for Analyzing Post Processed LC/MS Metabolomics Data," Anal Chem, Jan. 7, 2014 (Jan. 7, 2014), vol. 86, pp. 506-513.
Morgan et al. "Dysfunction of the intestinal microbiome in inflammatory bowel disease and treatment," Genome Biol. Apr. 16, 2012 (Apr. 16, 2012), vol. 13(9):R79, pp. 1-18. entire document.
Mutlu et al. "A Compositional Look at the Human Gastrointestinal Microbiome and Immune Activation Parameters in HIV Infected Subjects," PLoS Pathogens, Feb. 20, 2014 (Feb. 20, 2014), vol. 10, pp. 1-18.
Nakayama et al. "Aberrant Structures of Fecal Bacterial Community in Allergic Infants Profiled by 16S rRNA Gene Pyrosequencing," FEMS Immunology & Medical Microbiology, Dec. 1, 2011 (Dec. 1, 2011), vol. 63, pp. 397-406.
Ponnusamy et al. "Microbial community and metabolomic comparison of irritable bowel syndrome faeces," Feb. 17, 2011 (Feb. 17, 2011), vol. 60, pp. 817-827. entire document.
Blanton, et al., "Gut Bacteria That Prevent Growth Impairments Transmitted by Microbiota from Malnourished Children", Science, vol. 351, No. 6275, Feb. 19, 2016, 18 pages.
Canadian Application No. 2,962,466, Examination Report dated Mar. 23, 2018, 4 pages.
European Application No. 15852829.9, Extended European Search Report dated May 14, 2018, 8 pages.
International Application No. PCT/US2015/056767, International Preliminary Report on Patentability dated May 4, 2017, 9 pages.
International Application No. PCT/US2015/056767, International Search Report and Written Opinion dated Jan. 11, 2016, 10 pages.
International Application No. PCT/US2017/052098, International Search Report and Written Opinion dated Jan. 29, 2018, 13 pages.
Kinross, et al., "Gut Microbiome-host Interactions in Health and Disease", Genome Medicine, vol. 3, No. 14, 2011, pp. 1-12.
Morgan, et al., "Biodiversity and Functional Genomics in the Human Microbiome", Trends Genet., vol. 29, No. 1, Jan. 2013, pp. 51-58.
U.S. Appl. No. 14/919,614, Non-Final Office Action dated Jul. 14, 2016, 10 pages.
U.S. Appl. No. 14/919,614, Notice of Allowance dated May 19, 2017, 10 pages.
U.S. Appl. No. 15/606,743, Non-Final Office Action dated Dec. 19, 2017, 10 pages.
U.S. Appl. No. 15/606,743, Notice of Allowance dated Sep. 20, 2018, 5 pages.
U.S. Appl. No. 15/606,824, Final Office Action dated Sep. 20, 2018, 8 pages.
U.S. Appl. No. 15/606,824, Non-Final Office Action dated Jan. 16, 2018, 10 pages.
U.S. Appl. No. 15/606,874, Final Office Action dated Aug. 31, 2018, 8 pages.
U.S. Appl. No. 15/606,874, Non-Final Office Action dated Feb. 9, 2018, 10 pages.
U.S. Appl. No. 15/606,874, Notice of Allowance datedd Jan. 17, 2019, 5 pages.
U.S. Appl. No. 15/606,909, Final Office Action dated Sep. 20, 2018, 8 pages.
U.S. Appl. No. 15/606,909, Non-Final Office Action dated Mar. 9, 2018, 10 pages.
U.S. Appl. No. 15/606,909, Notice of Allowance dated Feb. 20, 2019, 5 pages.
U.S. Appl. No. 15/606,943, Final Office Action dated Nov. 1, 2018, 7 pages.
U.S. Appl. No. 15/606,943, Non-Final Office Action dated Apr. 10, 2018, 10 pages.
U.S. Appl. No. 15/606,943, Notice of Allowance dated Mar. 8, 2019, 5 pages.
U.S. Appl. No. 15/606,975, Final Office Action dated Jun. 14, 2018, 8 pages.
U.S. Appl. No. 15/606,975, Non-Final Office Action dated Sep. 25, 2017, 10 pages.
U.S. Appl. No. 15/606,975, Notice of Allowance dated Oct. 19, 2018, 5 pages.
U.S. Appl. No. 15/621,144, Final Office Action dated Nov. 1, 2018, 7 pages.
U.S. Appl. No. 15/621,144, Non-Final Office Action dated Apr. 10, 2018, 10 pages.
U.S. Appl. No. 15/621,144, Notice of Allowance dated Mar. 8, 2019, 6 pages.
U.S. Appl. No. 15/621,152, Final Office Action dated Nov. 1, 2018, 7 pages.
U.S. Appl. No. 15/621,152, Non-Final Office Action dated Apr. 10, 2018, 10 pages.
U.S. Appl. No. 15/621,152, Notice of Allowance dated Mar. 8, 2019, 6 pages.
Nadja B Kristensen et al., "Alterations in fecal microbiota composition by probiotic supplementation in healthy adults: a systematic review of randomized controlled trials", Genome Med. May 10, 2016;8(1):52. doi: 10.1186/s13073-016-0300-5.
Vincent Thomas et al., "Fecal microbiota analysis: an overview of sample collection methods and sequencing strategies", Future Microbiology, Future Medicine LTD, GB, vol. 10, No. 9, Jan. 1, 2015 (Jan. 1, 2015), pp. 1485-1504, XP009194769.
Stephan J Ott et al., "Quantification of intestinal bacterial populations by real-time PCR with a universal primer set and minor groove binder probes: a global approach to the enteric flora", J Clin Microbiol., Jun. 2004;42(6):2566-72. doi: 10.1128/JCM.42.6.2566-2572.2004.
Rachel Poretsky et al., "Strengths and limitations of 16S rRNA gene amplicon sequencing in revealing temporal microbial community dynamics", Plos One, vol. 9, No. 4, Apr. 8, 2014 (Apr. 8, 2014), page e93827, XP55820823, DOI: 10.1371/journal.pone.0093827.
Chih-Min Chiu et al., "Clinical detection of human probiotics and human pathogenic bacteria by using a novel high-throughput platform based on next generation sequencing", Journal of Clinical Bioinformatics, Biomed Central LTD, London, UK, vol. 4, No. 1, Jan. 13, 2014 (Jan. 13, 2014), p. 1, XP021175161.
Umberto Simeoni et al., "Gut microbiota analysis reveals a marked shift to bifidobacteria by a starter infant formula containing a synbiotic of bovine milk-derived oligosaccharides and *Bifidobacterium animalis* subsp. lactis CNCM I-3446", Environmental microbiology, vol. 18, No. 7, Dec. 2, 2015 (Dec. 2, 2015), pp. 2185-2195, XP55820498.
Daniel E. Almonacid et al., "16S rRNA Gene Sequencing as a Clinical Diagnostic Aid for Gastrointestinal-related Conditions", bioRxiv, Oct. 31, 2016 (Oct. 31, 2016), XP55820608.
Daniel E Almonacid et al., "16S rRNA gene sequencing and healthy reference ranges for 28 clinically relevant microbial taxa from the human gut microbiome", PLOS One, May 3, 2017 (May 3, 2017), page e0176555, XP55820597.
EPO, Search Report of EP. 17851735.5 dated Jul. 14, 2021.
IP Australia, Office Action of the corresponding Australian Patent Application No. 2017326564 dated Sep. 6, 2022.
Blanton, Laura V., et al. "Gut bacteria that prevent growth impairments transmitted by microbiota from malnourished children." Science 351.6275 (Feb. 19, 2016): aad3311.
IP Australia, Office Action of AU 2017326564 dated Apr. 13, 2023.
IP Australia, Office Action of AU 2017326564 dated Jun. 21, 2023.
Arthur Escalas et al., "Microbial functional diversity: From concepts to applications", Ecology and Evolution. Oct. 2019;9(20):12000-12016.
Cameron S. Dodd et al., "Functional Diversity within Gut Microbiomes: Implications for Conserving Biodiversity", Conservation. Oct. 25, 2021;1(4):311-326.

\* cited by examiner

Genera

| Target | Sensitivity | Specificity | Precision | NPV |
|---|---|---|---|---|
| Alistipes | 98.74 | 100.00 | 99.55 | 100.00 |
| Barnesiella | 99.32 | 100.00 | 99.73 | 100.00 |
| Bifidobacterium | 97.76 | 100.00 | 99.93 | 100.00 |
| Campylobacter | 98.60 | 100.00 | 99.90 | 100.00 |
| Peptoclostridium | 93.05 | 100.00 | 96.58 | 99.99 |
| Escherichia / Shigella | 98.06 | 99.99 | 98.91 | 99.98 |
| Fusobacterium | 98.02 | 100.00 | 99.59 | 99.99 |
| Lactobacillus | 98.02 | 99.98 | 98.45 | 99.97 |
| Odoribacter | 98.87 | 100.00 | 99.86 | 100.00 |
| Prevotella | 98.63 | 100.00 | 99.88 | 100.00 |
| Pseudoflavonifractor | 15.38 | 100.00 | 100.00 | 100.00 |
| Roseburia | 91.34 | 99.97 | 91.85 | 99.97 |
| Ruminococcus | 94.97 | 99.99 | 95.45 | 99.99 |
| Salmonella | 97.09 | 100.00 | 98.69 | 100.00 |
| Veillonella | 99.07 | 100.00 | 99.97 | 100.00 |

FIGURE 9A

Species

| Target | Sensitivity | Specificity | Precision | NPV |
|---|---|---|---|---|
| Akkermansia muciniphila | 100.00 | 100.00 | 100.00 | 100.00 |
| Anaerotruncus colihominis | 100.00 | 100.00 | 100.00 | 100.00 |
| Bacteroides fragilis | 97.32 | 99.99 | 99.60 | 99.99 |
| Bacteroides vulgatus | 8.82 | 100.00 | 100.00 | 99.99 |
| Bifidobacterium longum | 10.11 | 100.00 | 100.00 | 99.99 |
| Butyrivibrio crossotus | 100.00 | 100.00 | 100.00 | 100.00 |
| Campylobacter jejuni | 6.73 | 100.00 | 100.00 | 99.97 |
| Campylobacter coli | 18.30 | 99.99 | 92.85 | 99.99 |
| Campylobacter lari | 7.93 | 100.00 | 100.00 | 99.99 |
| Peptoclostridium difficile | 98.42 | 100.00 | 100.00 | 99.99 |
| Collinsella aerofaciens | 99.54 | 99.99 | 97.74 | 99.99 |
| Coprococcus eutactus | 50.00 | 100.00 | 100.00 | 99.99 |
| Desulfovibrio piger | 100.00 | 100.00 | 100.00 | 100.00 |
| Dialister invisus | 100.00 | 99.99 | 90.00 | 100.00 |
| Escherichia coli | 99.40 | 99.93 | 89.72 | 99.99 |
| Escherichia coli O157 | 3.18 | 99.99 | 53.84 | 99.98 |
| Faecalibacterium prausnitzii | 16.66 | 100.00 | 100.00 | 99.99 |
| Methanobrevibacter smithii | 100.00 | 100.00 | 100.00 | 100.00 |
| Oxalobacter formigenes | 100.00 | 100.00 | 100.00 | 100.00 |
| Ruminococcus albus | 100.00 | 100.00 | 100.00 | 100.00 |
| Ruminococcus bromii | 20.00 | 100.00 | 100.00 | 99.99 |
| Ruminococcus gnavus | 20.00 | 99.99 | 66.66 | 99.99 |
| Salmonella enterica | 98.99 | 99.99 | 99.84 | 99.99 |
| Salmonella bongori | 4.16 | 100.00 | 100.00 | 99.99 |
| Shigella boydii | 14.46 | 99.99 | 30.26 | 99.99 |
| Shigella sonnei | 35.06 | 99.99 | 72.00 | 99.99 |
| Shigella flexneri | 12.03 | 99.99 | 35.25 | 99.97 |
| Shigella dysenteriae | 49.35 | 99.99 | 60.31 | 99.99 |
| Streptococcus sanguinis | 93.25 | 100.00 | 100.00 | 99.99 |
| Streptococcus thermophilus | 8.69 | 100.00 | 100.00 | 99.99 |
| Vibrio cholerae | 98.84 | 99.99 | 96.79 | 99.99 |
| Yersinia enterocolitica | 8.18 | 99.99 | 63.63 | 99.99 |

METHOD AND SYSTEM FOR PANEL CHARACTERIZATIONS

CROSS-REFERENCE TO RELATED APPLICATIONS

This application is a continuation-in-part of U.S. Application Ser. No. 15/606,743, filed 26 May 2017, which is a continuation-in-part of U.S. application Ser. No. 14/919,614, filed 21 Oct. 2015, which claims the benefit of U.S. Provisional Application Ser. No. 62/066,369 filed 21 Oct. 2014, U.S. Provisional Application Ser. No. 62/087,551 filed 4 Dec. 2014, U.S. Provisional Application Ser. No. 62/092,999 filed 17 Dec. 2014, U.S. Provisional Application Ser. No. 62/147,376 filed 14 Apr. 2015, U.S. Provisional Application Ser. No. 62/147,212 filed 14 Apr. 2015, U.S. Provisional Application Ser. No. 62/147,362 filed 14 Apr. 2015, U.S. Provisional Application Ser. No. 62/146,855 filed 13 Apr. 2015, and U.S. Provisional Application Ser. No. 62/206,654 filed 18 Aug. 2015, which are each incorporated in their entirety herein by this reference. This application also claims the benefit of U.S. Provisional Application Ser. No. 62/395,939, filed 16 Sep. 2017, U.S. Provisional Application Ser. No. 62/520,058, file 15 Jun. 2017 and U.S. Provisional Application Ser. No. 62/525,379, filed 27 Jun. 2017, which are each incorporated in their entirety herein by this reference.

TECHNICAL FIELD

This invention relates generally to the field of microbiology and more specifically to a new and useful method and system for characterizing a panel of conditions in the field of microbiology.

BRIEF DESCRIPTION OF THE FIGURES

FIGS. 9A-9B are examples of target taxa;

Figure 11:
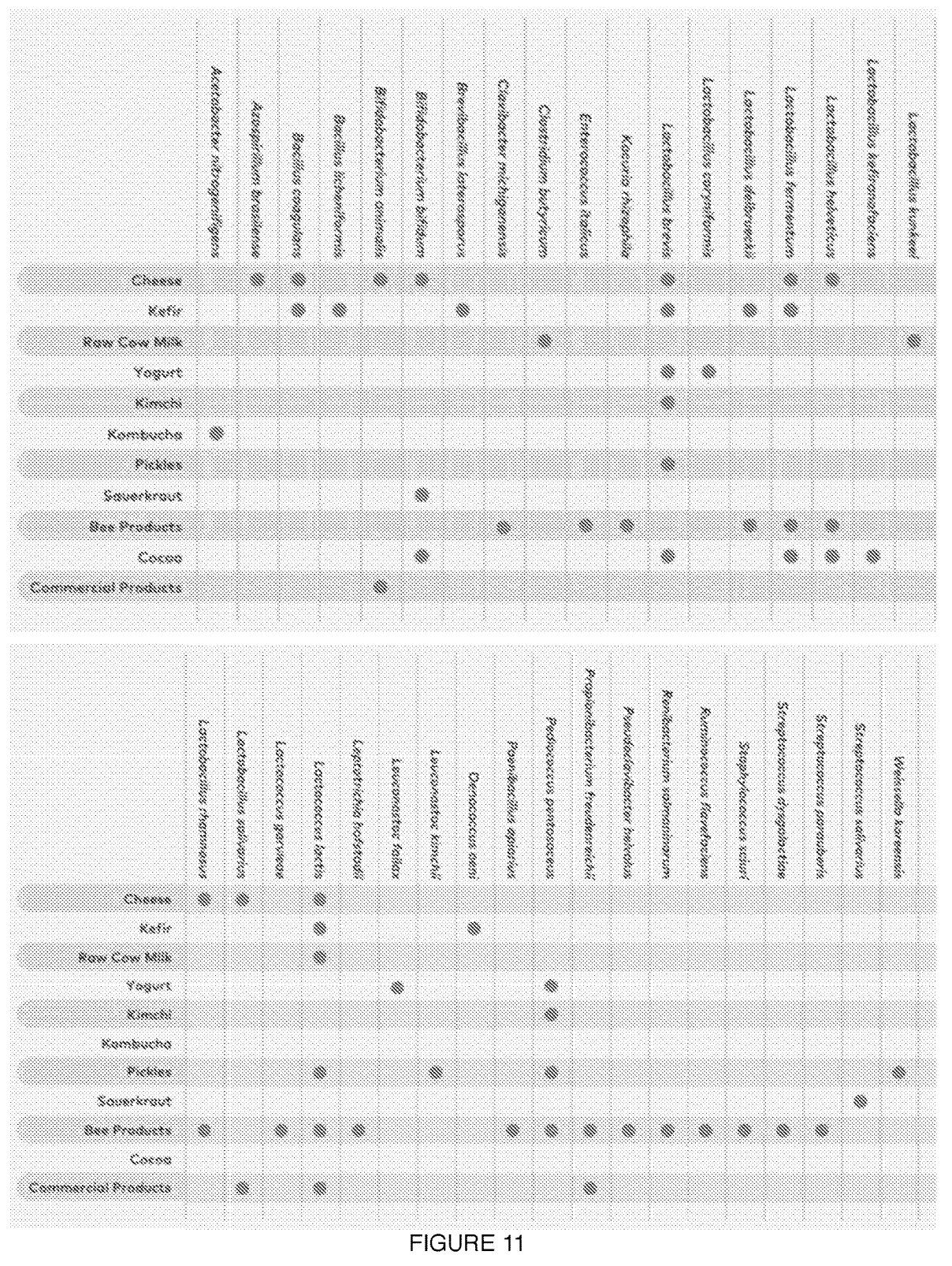

FIGS. 11-12 are examples of probiotics and associated taxonomic groups;

DESCRIPTION OF THE EMBODIMENTS

The following description of the embodiments of the invention is not intended to limit the invention to these embodiments, but rather to enable any person skilled in the art to make and use this invention.

1. Overview.

Figure 3:
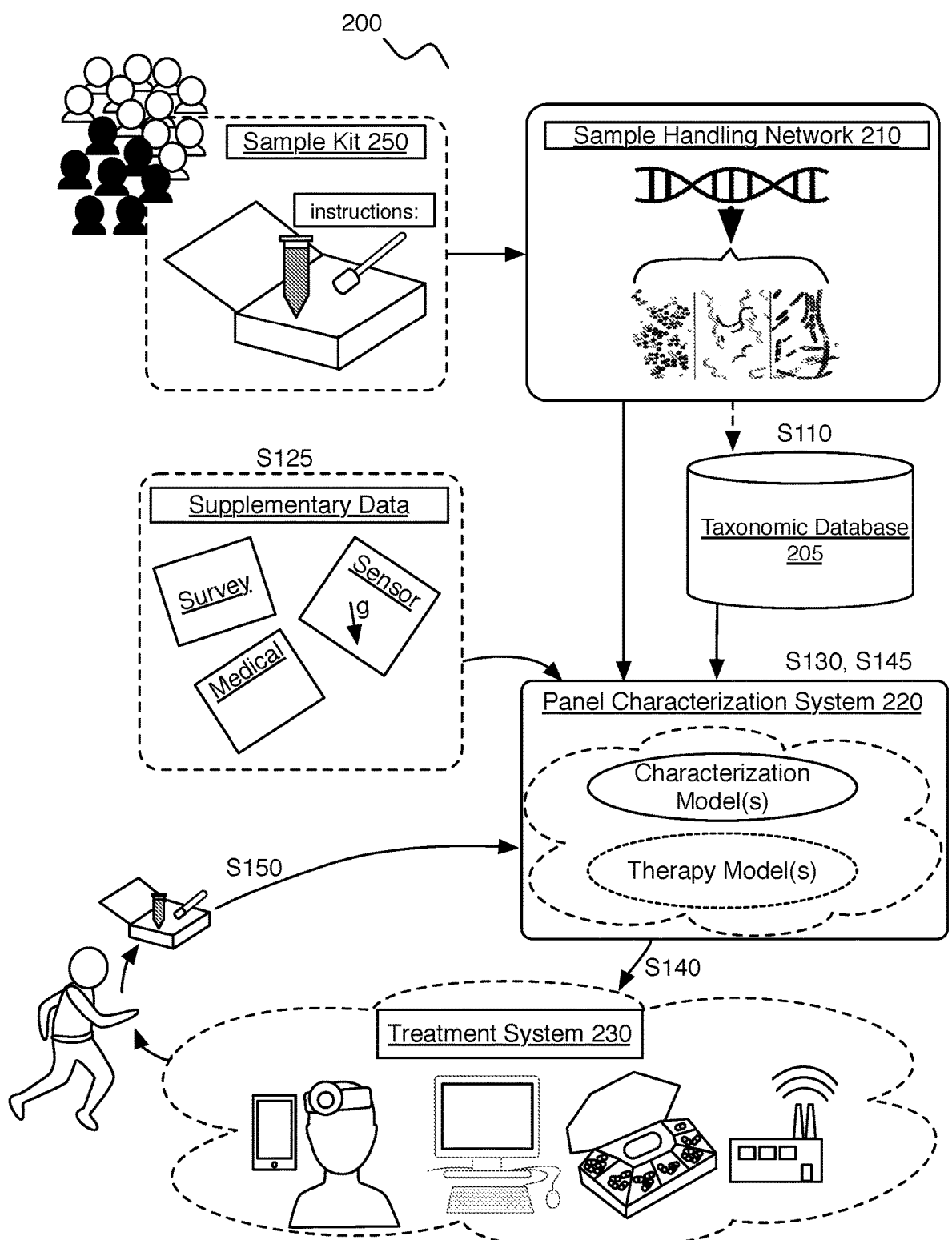
FIG. 3 is a schematic representation of an embodiment of a system.

As shown in FIG. 3, embodiments of a system 200 for characterizing a panel (e.g., plurality) of conditions (e.g., gut-related conditions) associated with a set of taxa related to microorganisms can include a taxonomic database 205 including reference microbiome features (e.g., microbiome composition diversity features; microbiome functional diversity features; microbiome pharmacogenomics features; etc.) for the set of taxa associated with the panel of conditions; a handling system 210 (e.g., a sample handling system, etc.) operable to collect a container including biological material (e.g., nucleic acid material, etc.) from a user (e.g., a human subject, patient, animal subject, environmental ecosystem, care provider, etc.), the handling system 210 including a sequencer system operable to determine a microorganism sequence dataset for the user from the biological material; a panel characterization system 220 operable to: determine user microbiome features (e.g., relative abundance ranges) for the set of taxa for the user based on the microorganism sequence dataset, generate a comparison between the user microbiome features and the reference microbiome features (e.g., reference relative abundance ranges, etc.), and determine a panel characterization for the panel of conditions for the user based on the comparison; and a treatment system 230 operable to promote a therapy for a condition of the panel of conditions based on the panel characterization (e.g., where the therapy is operable to modulate a user microbiome composition for improving a state of the condition, etc.).

The method 100 and/or system 200 can function to characterize, for a user, microbiome composition and/or microbiome functional diversity across a plurality of taxa (e.g., microorganisms across a plurality of species and genera) based on a biological sample of the user, in order to characterize a plurality of conditions associated with the plurality of taxa. In variations, the method 100 and/or system 200 can function to substantially concurrently generate characterizations in a multiplex manner for a plurality of users based on a plurality of biological samples derived for the plurality of users. However, the method 100 and/or system 200 can function in any manner analogous to that described in U.S. application Ser. No. 14/593,424 filed 9 Jan. 2015 and U.S. application Ser. No. 14/919,614, filed 21 Oct. 2015, each of which is herein incorporated in its entirety by this reference and/or can function in any suitable manner. The method 100 and/or system 200 can additionally or alternatively function to promote (e.g., provide) therapies (e.g., treatments, etc.) such as therapeutic measures to users for treating conditions of a panel of conditions (e.g., based on a panel characterization) and/or perform any suitable function. Variations of the system 200 and/or method 100 can further facilitate monitoring and/or adjusting of such therapies provided to a subject, for instance, through reception, processing, and analysis of additional samples from a subject throughout the course of therapy (e.g., for evaluating and/or improving a plurality of conditions from a panel).

In examples, the method 100 and/or system 200 can generate and/or promote characterizations and/or therapies for a panel of conditions including one or more of: symptoms, causes, diseases, disorders, microbiome pharmacogenomics profiles (e.g., describing resistance and/or susceptibility to antibiotics) and/or any other suitable aspects associated with the panel of conditions. The panel of conditions preferably includes a panel of gut-related conditions including any one or more of: flatulence, bloating, diarrhea, gastroenteritis, indigestion, abdominal pain, abdominal tenderness, constipation, infection, cancer, dysbiosis, irritable bowel syndrome (IBS), inflammatory bowel disease (IBD), ulcerative colitis, Crohn's disease, Celiac disease, bowel control problems (e.g., fecal incontinence), lactose intolerance, diverticulosis, diverticulitis, acid reflux (e.g., GER, GERD, etc.), Hirschsprung disease, abdominal adhesions, appendicitis, colon polyps, foodborne illnesses, gallstones, gastritis, gastroparesis, gastrointestinal bleeding, hemorrhoids, pancreatitis, ulcers, whipple disease, Zollinger-Ellison syndrome, related conditions, and/or any other suitable gut-related conditions. Additionally or alternatively, the panel of conditions can include one or more of: probiotics-related conditions (e.g., associated with microorganism taxonomic groups included in, affected by, and/or otherwise related to taxonomic groups included in probiotics; treatable with one or more probiotics; etc.); vaginal-related conditions (e.g., human Papillomavirus infection, syphilis, cervical cancer, squamous intraepithelial lesions for high- and low-grade, sexually transmitted infection, cervicitis, pelvic inflammatory disease, bacterial vaginosis, aerobic vaginitis, idiopathic infertility, etc.); psychiatric and behavioral conditions (e.g., a psychological disorder; depression; psychosis; anxiety; etc.); communication-related conditions (e.g., expressive language disorder; stuttering; phonological disorder; autism disorder; voice conditions; hearing conditions; eye conditions; etc.); sleep-related conditions (e.g., insomnia, sleep apnea; etc.); a cardiovascular-related condition (e.g., coronary artery disease; high blood pressure; etc.); metabolic-related conditions (e.g., diabetes, etc.), rheumatoid-related conditions (e.g., arthritis, etc.); weight-related conditions (e.g., obesity, etc.); pain-related conditions; endocrine-related conditions; genetic-related conditions; chronic disease; and/or any other suitable type of conditions. However, the method 100 and/or system 200 can be configured in any suitable manner.

2. Benefits

Microbiome analysis can enable accurate and efficient characterization and/or therapy provision for a panel of conditions caused by and/or otherwise associated with microorganisms. The technology can overcome several challenges faced by conventional approaches in characterizing and/or promoting therapies for a condition. First, conventional approaches can require patients to visit one or more care providers to receive a characterization and/or a therapy recommendation for a condition, which can amount to inefficiencies and health-risks associated with the amount of time elapsed before diagnosis and/or treatment. Second, conventional approaches can require a number of different diagnostic tests to be performed to characterize a panel of conditions, which can additionally amount to inefficiencies and health-risks. Third, conventional genetic sequencing and analysis technologies for human genome sequencing can be incompatible and/or inefficient when applied to the microbiome (e.g., where the human microbiome can include over 10 times more microbial cells than human cells; where optimal sample processing techniques can differ; where scaling sample processing procedures for characterizing a panel of conditions can be different; where the types of conditions can differ; where sequence reference databases can differ; where the microbiome can vary across different body regions of the user; etc.). Fourth, the onset of sequencing technologies (e.g., next-generation sequencing) has given rise to technological issues (e.g., data processing issues, issues with processing in a multiplex manner, information display issues, microbiome analysis issues, therapy prediction issues, therapy provision issues, etc.) that would not exist but for the unprecedented advances in speed and data generation associated with sequencing genetic material. Examples of the system 200 and the method 100 can confer technologically-rooted solutions to at least the challenges described above.

First, the technology can confer improvements in computer-related technology (e.g., modeling associated with characterizing and/or promoting therapies for a panel of conditions; improving computational efficiency in storing, retrieving, and/or processing microorganism-related data for a panel of conditions; computational processing associated with biological sample processing; etc.) by facilitating computer performance of functions not previously performable. For example, the technology can computationally generate panel characterizations and/or associated recommended therapies based on techniques (e.g., leveraging microorganism taxonomic databases, etc.) that are recently viable due to advances in sample processing techniques and sequencing technology.

Second, the technology can confer improvements in processing speed, panel characterization accuracy, microbiome-related therapy determination and promotion, and/or other suitable aspects in relation to a panel of conditions. For example, the technology can generate and apply feature-selection rules (e.g., microbiome diversity feature-selection rules for composition, function, pharmacogenomics, etc.) to select an optimized subset of features (e.g., microbiome composition diversity features such as reference relative abundance features indicative of healthy ranges of taxonomic groups associated with a panel of conditions; user relative abundance features that can be compared to the reference relative abundance features; etc.) out of a vast potential pool of features (e.g., extractable from the plethora of microbiome data such as sequence data) for generating and/or applying characterization models and/or therapy models. The potential size of microbiomes (e.g., human microbiomes, animal microbiomes, etc.) can translate into a plethora of data, giving rise to questions of how to process and analyze the vast array of data to generate actionable microbiome insights in relation to a panel of conditions. However, the feature-selection rules and/or other suitable computer-implementable rules can enable shorter generation and execution times (e.g., for generating and/or applying taxonomic databases; for determining panel characterizations and/or associated therapies; etc.), model simplification facilitating efficient interpretation of results, reduction in overfitting, improvements in data sources (e.g., for generating taxonomic databases, etc.), improvements in identifying and presenting panel condition insights in relation to the microbiome (e.g., through collecting and processing an increasing amount of data associated with an increasing number of users to improve predictive power of the technology), improvements in data storage and retrieval (e.g., storing specific models, microorganism sequences, features, and/or other suitable data in association with a user and/or set of users to improve delivery of personalized characterizations and/or treatments for panels of conditions, etc.), and other suitable improvements to facilitate rapid determination of characterizations and/or therapies.

Third, the technology can transform entities (e.g., users, biological samples, treatment systems including medical devices, etc.) into different states or things. For example, the technology can transform a biological sample into a panel characterization for a plurality of conditions. In another example, the system 200 and/or method 100 can identify therapies to promote to a patient to modify a microbiome composition, microbiome functional diversity, a microbiome pharmacogenomics profile and/or other microbiome-related aspects to prevent and/or ameliorate one or more conditions of a panel of conditions, thereby transforming the microbiome and/or health of the patient. In another example, the technology can transform a biological sample (e.g., through fragmentation, multiplex amplification, sequencing, etc.) received by patients into microbiome datasets, which can subsequently be transformed into features correlated with a panel of conditions, in order to generate panel characterization models and/or therapy models. In another example, the technology can control treatment systems to promote therapies (e.g., by generating control instructions for the treatment system to execute), thereby transforming the treatment system. In another example, the improvements in computer-related technology can drive transformations in the biological sample processing approaches, such as selecting a subset of primers compatible with genetic targets associated with a panel of conditions.

Fourth, the technology can amount to an inventive distribution of functionality across a network including a taxonomic database, a sample handling system, a panel characterization system, and a plurality of users, where the sample handling system can handle substantially concurrent processing of biological samples (e.g., in a multiplex manner) from the plurality of users, which can be leveraged, along with the taxonomic database, by the panel characterization system in generating personalized characterizations and/or therapies (e.g., customized to the user's microbiome such as in relation to the user's dietary behavior, probiotics-associated behavior, medical history, demographics, other behaviors, preferences, etc.) for a panel of conditions.

Fifth, the technology can improve the technical fields of at least computational modeling of a panel of conditions in relation to microbiome digital medicine, digital medicine generally, genetic sequencing, and/or other relevant fields. Sixth, the technology can leverage specialized computing devices (e.g., devices associated with the sample handling system, such as sequencer systems; panel characterization systems; treatment systems; etc.) in determining and processing microbiome datasets for characterizing and/or determining therapies for a panel of conditions. The technology can, however, provide any other suitable benefit(s) in the context of using non-generalized computer systems for panel characterization and/or microbiome modulation.

3.1 System—Taxonomic Database

The taxonomic database 205 of the system 200 can function to provide marker information associated with a panel of conditions and suitable for comparison to user microbiome features in generating one or more panel characterizations. For example, the taxonomic database 205 can store microorganism genetic sequences in association with a corresponding plurality of taxa, which can be stored in association with one or more corresponding conditions. In another example, the taxonomic database 205 can store reference relative abundance ranges (e.g., associated with a healthy state for one or more conditions, associated with an unhealthy state, etc.) and/or other suitable microbiome features for microorganism taxonomic groups associated with the panel of conditions, where the reference microbiome features can be extracted based on a set of biological samples from a population of users (e.g., exhibiting one or more conditions of the panel of conditions; not exhibiting the conditions; etc.). In another example, the taxonomic database 205 can store user relative abundance ranges (e.g., for a user with an unknown microbiome profile in relation to the panel of conditions; etc.) and/or other suitable user microbiome features.

The taxonomic database 205 preferably stores markers including any one or more of: genetic sequences (e.g., sequences identifying a taxonomic group; microorganism sequences; human sequences; sequences indicative of conditions from a panel of conditions; sequences that are invariant across a set of microorganism taxonomic groups and/or users; conserved sequences; sequences including mutations; sequences including polymorphisms; etc.); peptide sequences; targets; features (e.g., microbiome composition diversity features, microbiome functional diversity features, microbiome pharmacogenomics features, etc.); protein types (e.g., serum proteins, antibodies, etc.); carbohydrate types; lipid types; whole cell markers; metabolite markers; natural product markers; genetic predisposition biomarkers; diagnostic biomarkers; prognostic biomarkers; predictive biomarkers; other molecular biomarkers; gene expression markers; imaging biomarkers; markers corresponding to functional, structural, evolutionary, and/or other suitable characteristics associated with microorganisms; and/or other suitable markers associated with microorganisms (e.g., taxa) and/or associated conditions. Genetic sequences stored by the taxonomic database 205 preferably include one or more gene sequences for rRNA (e.g., a variable region of an rRNA gene sequence), which can include any one or more of: 16S, 18S, 30S, 40S, 50S, 60S, 5S, 23S, 5.8S, 28S, 70S, 80S, and/or any other suitable rRNA. Additionally or alternatively, genetic sequences can include and/or otherwise be associated with other RNA genes, protein genes, other RNA sequences, DNA sequences and/or any other suitable genetic aspects. Different markers stored by the taxonomic database 205 preferably share a marker characteristic, which can include one or more of: conserved genetic sequences across the plurality of taxa (e.g., semi-conserved genetic sequences including a variable region; conserved sequences that can be targeted by primers for targeting a plurality of taxonomic groups associated with a panel of conditions; etc.), conserved peptide sequences, shared biomarkers, and/or any other suitable marker-associated information.

Stored markers are preferably associated with a plurality of taxa, in order to enable mapping of user microorganism sequences (e.g., derived from a collected biological sample of a user, etc.) to particular taxa based on a comparison with stored markers (e.g., comparing user microorganism sequences to stored markers to find matches satisfying predetermined conditions; identifying taxa associated with the matched markers; and associating the taxa to the user microorganism sequences; etc.). Taxonomic groups in relation to the taxonomic database 205, a panel of conditions (e.g., gut-related conditions), other system components, and/or any portion of the system 200 and method 100 can include one or more of: *Clostridium* (genus), *Clostridium difficile* (species), *Alistipes* (genus), *Alloprevotella* (genus), *Anaerofilum* (genus), *Bacteroides* (genus), *Barnesiella* (genus), *Bifidobacterium* (genus), *Blautia* (genus), *Butyricimonas* (genus), *Campylobacter* (genus), *Catenibacterium* (genus), *Christensenella* (genus), *Collinsella* (genus), *Coprococcus* (genus), *Dialister* (genus), *Eggerthella* (genus), *Escherichia-Shigella* (genus), *Faecalibacterium* (genus), *Flavonifractor* (genus), *Fusobacterium* (genus), *Gelria* (genus), *Haemophilus* (genus), *Holdemania* (genus), *Lactobacillus* (genus), *Odoribacter* (genus), *Oscillibacter* (genus), *Oscillospira* (genus), *Parabacteroides* (genus), *Paraprevotella* (genus), *Peptoclostridium* (genus), *Phascolarctobacterium* (genus), *Prevotella* (genus), *Pseudoflavonifractor* (genus), *Roseburia* (genus), *Ruminococcus* (genus), *Salmonella* (genus), *Streptococcus* (genus), *Turicibacter*

(genus), *Tyzzerella* (genus), *Veillonella* (genus), *Acetobacter nitrogenifigens* (species), *Acinetobacter baumannii* (species), *Akkermansia muciniphila* (species), *Anaerotruncus colihominis* (species), *Azospirillum brasilense* (species), *Bacillus cereus* (species), *Bacillus coagulans* (species), *Bacillus licheniformis* (species), *Bacteroides fragilis* (species), *Bacteroides vulgatus* (species), *Bifidobacterium longum* (species), *Bifidobacterium animalis* (species), *Bifidobacterium bifidum* (species), *Brevibacillus laterosporus* (species), *Butyrivibrio crossotus* (species), *Campylobacter jejuni* (species), *Campylobacter coli* (species), *Campylobacter lari* (species), *Christensenella minuta* (species), *Clavibacter michiganensis* (species), *Clostridium butyricum* (species), *Collinsella aerofaciens* (species), *Coprococcus eutactus* (species), *Desulfovibrio piger* (species), *Dialister invisus* (species), *Enterococcus italicus* (species), *Escherichia coli* (species), *Escherichia coli* O157 (species), *Faecalibacterium prausnitzii* (species), *Fibrobacter succinogenes* (species), *Kocuria rhizophila* (species), *Lactobacillus brevis* (species), *Lactobacillus coryniformis* (species), *Lactobacillus delbrueckii* (species), *Lactobacillus fermentum* (species), *Lactobacillus helveticus* (species), *Lactobacillus kefiranofaciens* (species), *Lactobacillus kunkeei* (species), *Lactobacillus rhamnosus* (species), *Lactobacillus salivarius* (species), *Lactococcus fujiensis* (species), *Lactococcus garvieae* (species), *Lactococcus lactis* (species), *Leptotrichia hofstadii* (species), *Leuconostoc fallax* (species), *Leuconostoc kimchii* (species), *Methanobrevibacter smithii* (species), *Oenococcus oeni* (species), *Oxalobacter formigenes* (species), *Paenibacillus apiarius* (species), *Pediococcus pentosaceus* (species), *Peptoclostridium difficile* (species), *Propionibacterium freudenreichii* (species), *Pseudoclavibacter helvolus* (species), *Renibacterium salmoninarum* (species), *Ruminococcus albus* (species), *Ruminococcus flavefaciens* (species), *Ruminococcus bromii* (species), *Ruminococcus gnavus* (species), *Salmonella bongori* (species), *Salmonella enterica* (species), *Shigella boydii* (species), *Shigella sonnei* (species), *Shigella flexneri* (species), *Shigella dysenteriae* (species), *Staphylococcus sciuri* (species), *Streptococcus sanguinis* (species), *Streptococcus thermophilus* (species), *Vibrio cholerae* (species), *Weissella koreensis* (species), *Yersinia enterocolitica* (species), and/or any other suitable marker-associated information (e.g., taxa). Additionally or alternatively, taxonomic groups can include any described in U.S. application Ser. No. 14/919,614, filed 21 Oct. 2015. For example, markers stored in association with one or more of the plurality of taxa described above can include 16S rRNA genetic sequences associated with the plurality of taxa. The markers and/or the plurality of taxa can be associated (e.g., positively associated, negatively associated, etc.) with one or more: conditions, pathogens, commensal bacteria, probiotic bacteria, and/or any other marker-associated information.

In variations, the taxonomic database 205 can store markers (e.g., microorganism sequences, abundance features such as relative abundance ranges, microbiome composition diversity features, microbiome functional diversity features, other features, etc.), associated taxonomic groups, and/or other suitable data related to probiotics (and/or other suitable microorganism-related therapies). As such, the taxonomic database 205 can improve storage and/or retrieval of probiotics-related data for characterizing a user microbiome in relation to probiotics-related microorganisms (e.g., taxonomic groups present in probiotics) and/or associated conditions (e.g., a panel of gut-related conditions and/or other suitable conditions, etc.). Food sources of probiotics can include: milk (e.g., raw cow milk), kefir, cheese (e.g., ovine cheese), cocoa, kimchi, yogurt, kombucha, sauerkraut, bee products, pickles, natto, pickles, fermented foods (e.g., fermented sausages), other probiotic foods, probiotic supplements (e.g., probiotic pills, commercial probiotics, etc.), and/or other suitable types of probiotics.

Figure 14:
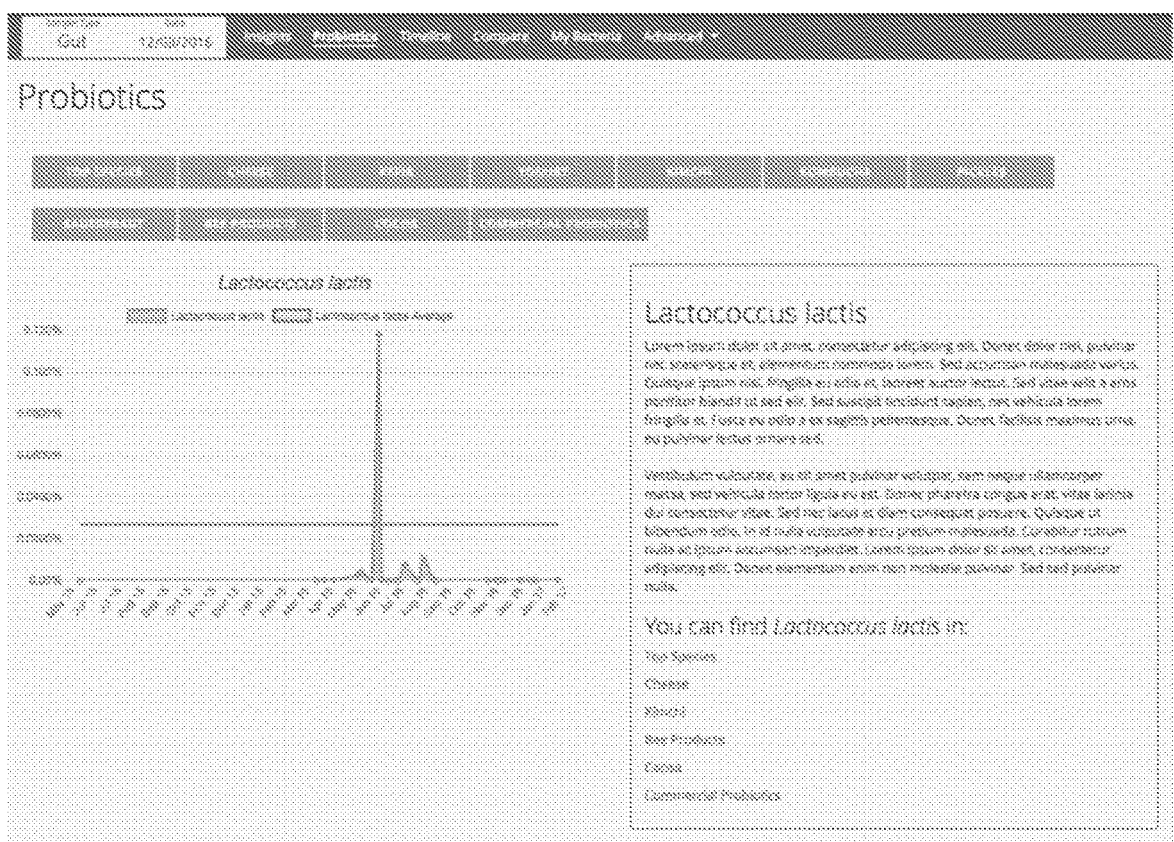
FIGS. 14-15 are examples of interfaces.
Figure 15:
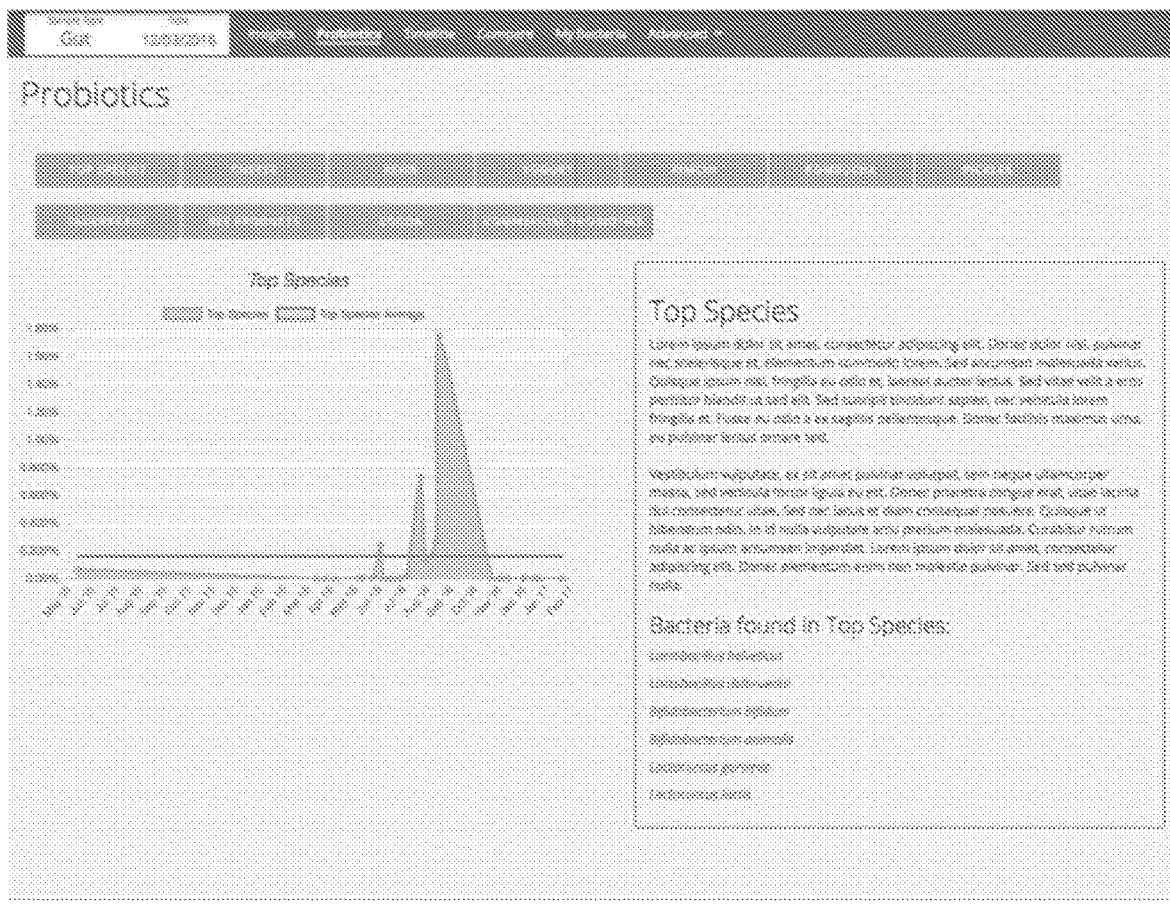

As shown in FIGS. 11-12 and 13A-13B, taxonomic groups associated with probiotics, conditions, other system components, and/or any portion of the system 200 and method 100 can include one or more of: *Bacillus coagulans* (species), *Bifidobacterium animalis* (species), *Clostridium butyricum* (species), *Lactobacillus brevis* (species), *Lactobacillus coryniformis* (species), *Lactobacillus fermentum* (species), *Lactobacillus helveticus* (species), *Lactobacillus rhamnosus* (species), *Streptococcus salivarius* (species), *Acetobacter nitrogenifigens* (species), *Azospirillum brasilense* (species), *Bacillus licheniformis* (species), *Bifidobacterium bifidum* (species), *Brevibacillus laterosporus* (species), *Clavibacter michiganensis* (species), *Enterococcus italicus* (species), *Kocuria rhizophila* (species), *Lactobacillus delbrueckii* (species), *Lactobacillus kefiranofaciens* (species), *Lactobacillus kunkeei* (species), *Lactobacillus salivarius* (species), *Lactococcus garvieae* (species), *Lactococcus lactis* (species), *Leptotrichia hofstadii* (species), *Leuconostoc fallax* (species), *Leuconostoc kimchii* (species), *Oenococcus oeni* (species), *Paenibacillus apiarius* (species), *Pediococcus pentosaceus* (species), *Propionibacterium freudenreichii* (species), *Pseudoclavibacter helvolus* (species), *Renibacterium salmoninarum* (species), *Ruminococcus flavefaciens* (species), *Staphylococcus sciuri* (species), *Streptococcus dysgalactiae* (species), *Streptococcus parauberis* (species), and *Weissella koreensis* (species). In a specific example, the taxonomic database 205 can include markers for a specific set of taxonomic groups including *Bacillus coagulans* (species), *Bifidobacterium animalis* (species), *Clostridium butyricum* (species), *Lactobacillus brevis* (species), *Lactobacillus coryniformis* (species), *Lactobacillus fermentum* (species), *Lactobacillus helveticus* (species), *Lactobacillus rhamnosus* (species), and *Streptococcus salivarius* (species), where the markers (e.g., for the specific set of taxonomic groups, for any suitable set of taxonomic groups, etc.) can be leveraged in generating a panel characterization of probiotics-related microorganisms (e.g., composition characteristics, functional diversity characteristics) in relation to corresponding probiotics (e.g., as shown in FIGS. 14-15). In a specific example of a taxonomic group characterization associated with probiotics can include, for the taxonomic group of *Pediococcus pentosaceus* (species): found in raw cow milk, kimchi, sauerkraut, pickles; spherical shape; 0.5-1.0 micrometer size; non-spore forming; non-motile; non-flagellate; G+; lactic acid producer; used as start culture in different fermentations; and/or other suitable characteristics. In another specific example, the taxonomic database can be leveraged for characterizing the specific set of taxonomic groups and/or other suitable set of taxonomic groups in relation to a set of conditions, such as based on an inverse association with IBS, an inverse association with type 2 diabetes, an inverse association with obesity, an inverse association with IBD, an inverse association respiratory infection duration, an association with weight loss, and/or any suitable association (e.g., inverse association, positive association, etc.) with any suitable condition. However, the taxonomic database 205 can be applied in relation to probiotics in any suitable manner.

The taxonomic database 205 can be generated, used for storage, retrieved from, determined, and/or otherwise applied through performing portions of the method 100 (e.g., Block S110). For example, the taxonomic database 205 can include a set of reference relative abundance ranges (and/or other suitable reference microbiome features) derived from: determining a target set of taxa associated with a panel of conditions (e.g., gut-related conditions, etc.), determining a set of reference markers; and determining the set of reference relative abundance ranges for a set of taxa selected based on a comparison between the set of reference markers and the target set of taxa. Determining the set of reference markers (and/or other reference microbiome features) can include determining the set of reference markers based on predicted reads derived from a set of primers selected based on a marker characteristic shared across a plurality of taxonomic groups (e.g., which can improve efficiency in sample processing for facilitating panel characterizations, where same or similar type of primers can be used to target markers across a plurality of taxonomic groups associated with a panel of conditions, etc.), where the comparison between the set of reference markers and the target set of taxa can include a sequence similarity between the predicted reads and reference microorganism sequences associated with the target set of taxa.

3.2 System—Handling System

The handling system 210 of the system 200 can function to receive and process (e.g., fragment, amplify, sequence, etc.) biological samples. The handling system 210 can additionally or alternatively function to provide and/or collect sample kits 250 (e.g., including containers configured for receiving biological material, instructions for users to guide a self-sampling process, etc.) for a plurality of users (e.g., in response to a purchase order for a sample kit 250), such as through a mail delivery system and/or other suitable process. In examples, the sample kits 250 can include materials and associated instructions for a user to collect a sample (e.g., through cotton tip swabs; aspiration of fluids; biopsy; etc.) from one or more collection sites. Collection sites can be associated with one or more of: the female genitals, the male genitals, the rectum, the gut, the skin, the mouth, the nose, any mucous membrane, and/or any other suitable sample providing site (e.g., blood, sweat, urine, feces, semen, vaginal discharges, tears, tissue samples, interstitial fluid, other body fluid, etc.), where any individual site or combination of sites can be correlated with any suitable taxonomic groups and/or associated conditions described herein. The handling system 210 can additionally or alternatively include a library preparation system operable to automatically prepare biological samples (e.g., fragment and/or amplify using primers compatible with nucleic acid sequences associated with the antibiotics-associated condition, such as in a multiplex manner, etc.) to be sequenced by a sequencer system (e.g., a next generation sequencing platform); and/or any suitable components. In another example, the handling system 210 can be operable to determine a microorganism sequence dataset based on amplification of nucleic acids from biological material using a primer of a set of primers (e.g., selected through performing Block S110 and/or other suitable portions of the method 100, etc.), where the primer targets a microorganism sequence corresponding to a taxonomic group associated with one or more conditions of a panel of conditions (and/or one or more probiotics). In variations, the handling system 210 can be configured in any manner and/or include components (e.g., sequencer systems) described in any manner analogous to U.S. application Ser. No. 14/919,614, filed 21 Oct. 2015. However, the handling system 210 and associated components can be configured in any suitable manner.

3.3 System—Panel Characterization System

The panel characterization system 220 of the system 200 can function to determine and/or analyze microbiome datasets and/or supplementary datasets for characterizing and/or determining therapies for a panel of conditions (e.g., through performing portions of the method 100, etc.). In a variation, the panel characterization system 220 can obtain and/or apply computer-implemented rules (e.g., taxonomic database 205 generation rules; feature selection rules; model generation rules; user preference rules; data storage, retrieval, and/or display rules; microorganism sequence generation rules; sequence alignment rules; and/or any other suitable rules). However, the panel characterization system 220 can be configured in any suitable manner.

3.4 System—Treatment System

The treatment system 230 of the system 200 functions to promote one or more treatments to a user (e.g., a human subject; a care provider facilitating provision of the treatment; etc.) for treating one or more conditions of the panel of conditions (e.g., reducing the risk of the conditions; improving states of the conditions; improving symptoms and/or other suitable aspects of the conditions; modifying a microbiome pharmacogenomics profile of a user towards a state susceptible to treatments for the conditions, etc.). The treatment system 230 can include any one or more of: a communications system (e.g., to communicate treatment recommendations, such as through an interface 240, through notifying a care provider to recommend and/or provide the treatment; to enable telemedicine; etc.), an application executable on a user device (e.g., a gut-panel condition application for promoting treatments for gut-related conditions; a medication reminder application; an application operable to communicate with an automatic medication dispenser; etc.), consumable therapies such as supplemental probiotics (e.g., type, dosage, treatment schedule, amounts and types of taxonomic groups included, etc.), probiotic foods, antibiotics (e.g., type, dosage, medication schedule etc.), supplementary medical devices (e.g., medication dispensers; medication devices associated with antibiotic provision, etc.), user devices (e.g., including biometric sensors), and/or any other suitable component. In an example, the treatment system 230 can be operable to facilitate provision of a consumable therapy based on the panel characterization, where the consumable therapy is operable to affect the user for at least one of a microbiome composition and a microbiome function associated with the condition (e.g., gut-related condition, etc.), in promoting improvement of a state of the condition. In a specific example, the therapy can include a probiotics-related therapy for the condition, where the probiotics-related therapy is associated with a set of taxa (e.g., including taxonomic groups described herein, etc.), and where the treatment system 230 includes an interface 240 for promoting the probiotics-related therapy in association with a taxonomic group from the set of taxa. One or more treatment systems 230 are preferably controllable by the panel characterization system 220. For example, the panel characterization system 220 can generate control instructions and/or notifications to transmit to the treatment system 230 for activating and/or otherwise operating the treatment system 230 in promoting therapies. However, the treatment system 230 can be configured in any other manner.

3.5 System—Interface

As shown in FIGS. 14-15, the system 200 can additionally or alternatively include an interface 240 that can function to improve presentation of panel characterization information, probiotic-related information, and/or other suitable microbiome-related information in relation to, for example, panel characterizations, associated therapy recommendations, comparisons to other users, comparisons based on demographics and/or other user characteristics, microbiome and/or composition diversity, microbiome functional diversity, microbiome pharmacogenomics, and/or other suitable aspects. In another example, the interface 240 can present panel characterization information including a microbiome composition (e.g., relative abundances of taxonomic groups), functional diversity (e.g., relative abundance of genes and/or other functional-related characteristics, etc.), and/or other suitable information for a panel of conditions (e.g., composition in relation to conditions of the panel, etc.). In another example, panel characterization information, probiotic-related information, and/or other suitable information can be presented relative to a user subgroups sharing a characteristic (e.g., similar dietary behaviors, similar demographic characteristics, patients sharing conditions, smokers, exercisers, users on different dietary regimens, consumers of probiotics, antibiotic users, groups undergoing particular therapies, etc.).

In another example, the interface 240 can be operable to present antibiotics-related information including a change in the microbiome pharmacogenomics profile (and/or microbiome composition, microbiome functional diversity, etc.) over time in relation to the treatment and the antibiotics-associated condition. In a specific example, the interface 240 can be operable to improve display of antibiotics-related information associated with the antibiotics-treatable condition and derived based on a comparison between a user microbiome pharmacogenomics profile for the user relative a user group sharing a demographic characteristic. In another specific example, the interface 240 can promote (e.g., present, provide a notification, etc.) a therapy (e.g., a probiotics-related therapy) in association with a taxonomic group from the set of taxa (e.g., recommending a probiotic including microorganisms of a taxonomic group associated with a condition of the panel of conditions, etc.). In another specific example, the interface's display of microbiome-related information can be improved through selection (e.g., based on components of the panel characterization satisfying a threshold condition; a user microbiome profile matching a reference profile beyond a threshold similarity; a risk of a condition of a panel exceeding a threshold; other trigger events; etc.) and presentation of a subset of the microbiome-related information (e.g., highlighting and/or otherwise emphasizing a subset of the information). However, the interface 240 can display any suitable information and can be configured in any suitable manner.

The system 200 and/or components of the system 200 can entirely or partially be executed by, hosted on, communicate with, and/or otherwise include: a remote computing system (e.g., a server, at least one networked computing system, stateless, stateful), a local computing system, databases (e.g., taxonomic database 205, user database, microbiome dataset database, panel of conditions database, treatment database, etc.), a user device (e.g., a user smart phone, computer, laptop, supplementary medical device, wearable medical device, care provider device, etc.), and/or any suitable component. For example, the system 200 can include a computing system operable to communicate with the handling system 210 (e.g., a next generation sequencing platform of the handling system 210) to perform suitable portions of the method 100, such as determining microbiome pharmacogenomics data. While the components of the system 200 are generally described as distinct components, they can be physically and/or logically integrated in any manner. For example, a smartphone application can partially or fully implement the panel characterization system 220 (e.g., apply a panel characterization model to generate a panel characterization for a panel of conditions, such as in real-time; sequence biological samples; process microorganism sequences; extract features from microbiome datasets; etc.) and the treatment system 230 (e.g., communicate with a calendar application of the smartphone to notify the user to take probiotics according to the parameters determined by a probiotic therapy model, etc.). Additionally or alternatively, the functionality of the system 200 can be distributed in any suitable manner amongst any suitable system components. However, the components of the system 200 can be configured in any suitable manner.

4. Method

Figure 1A:
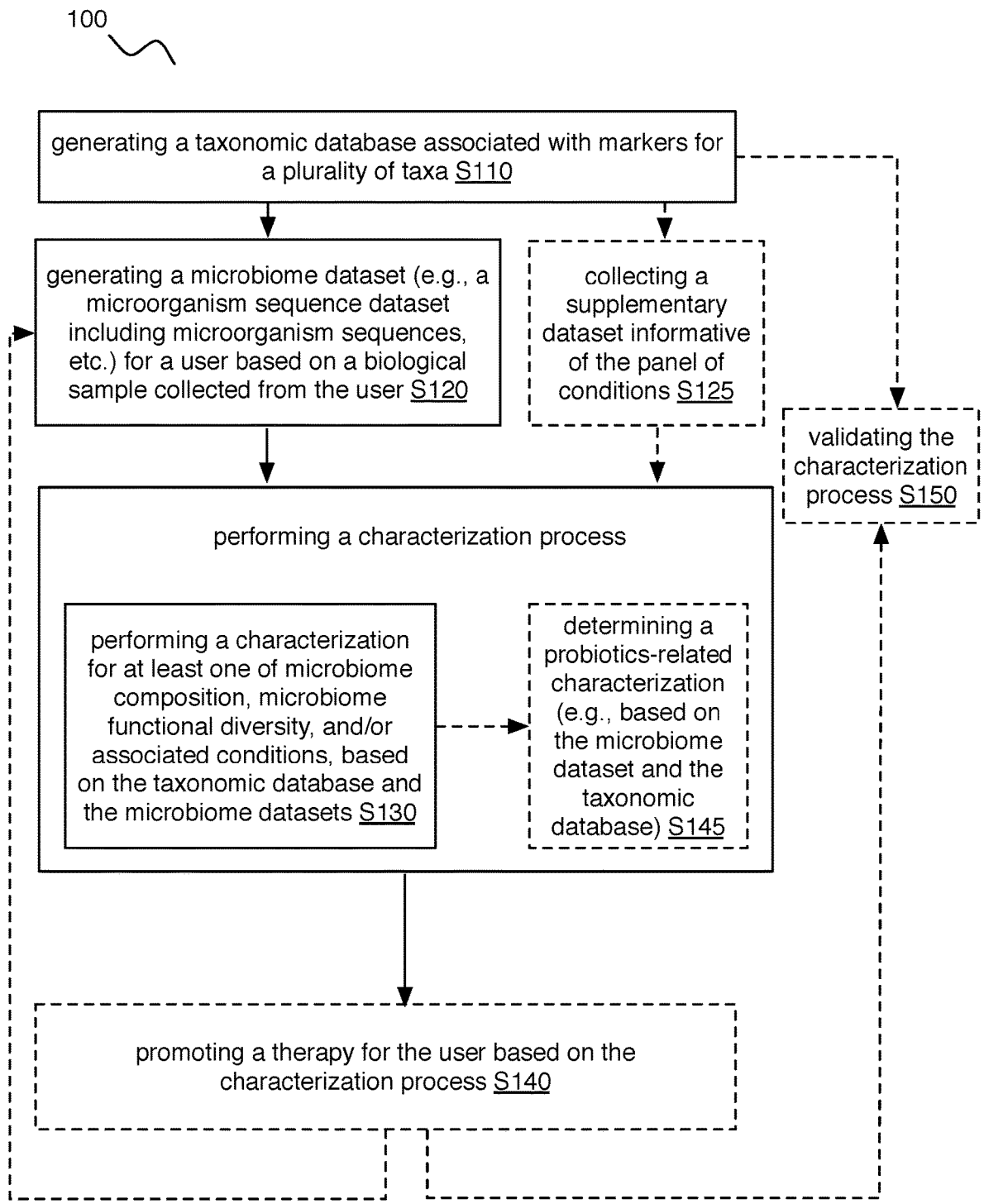
FIGS. 1A-1B are flowchart representations of variations of an embodiment of a method for characterizing a panel of conditions.
Figure 1B:
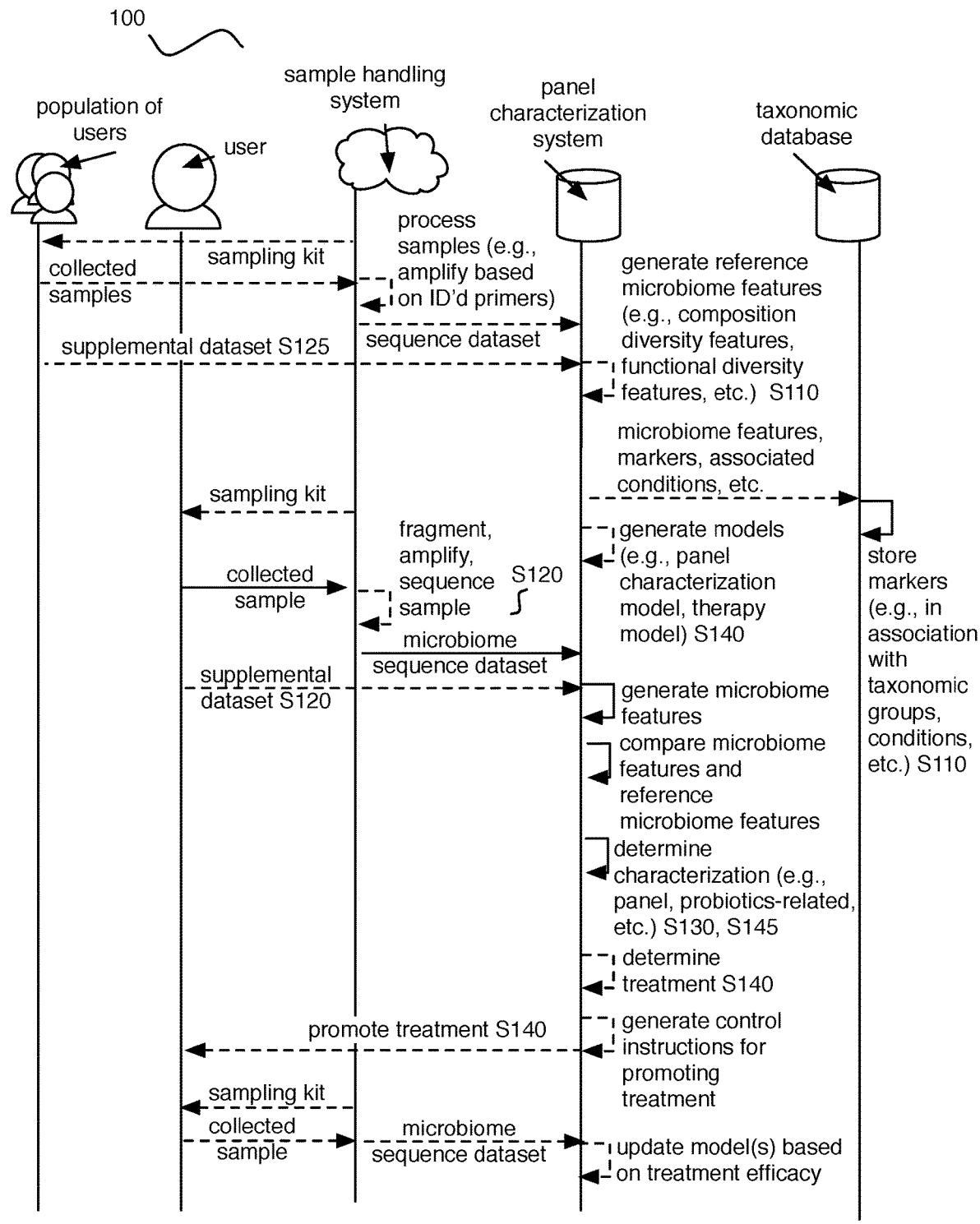
Figure 2:
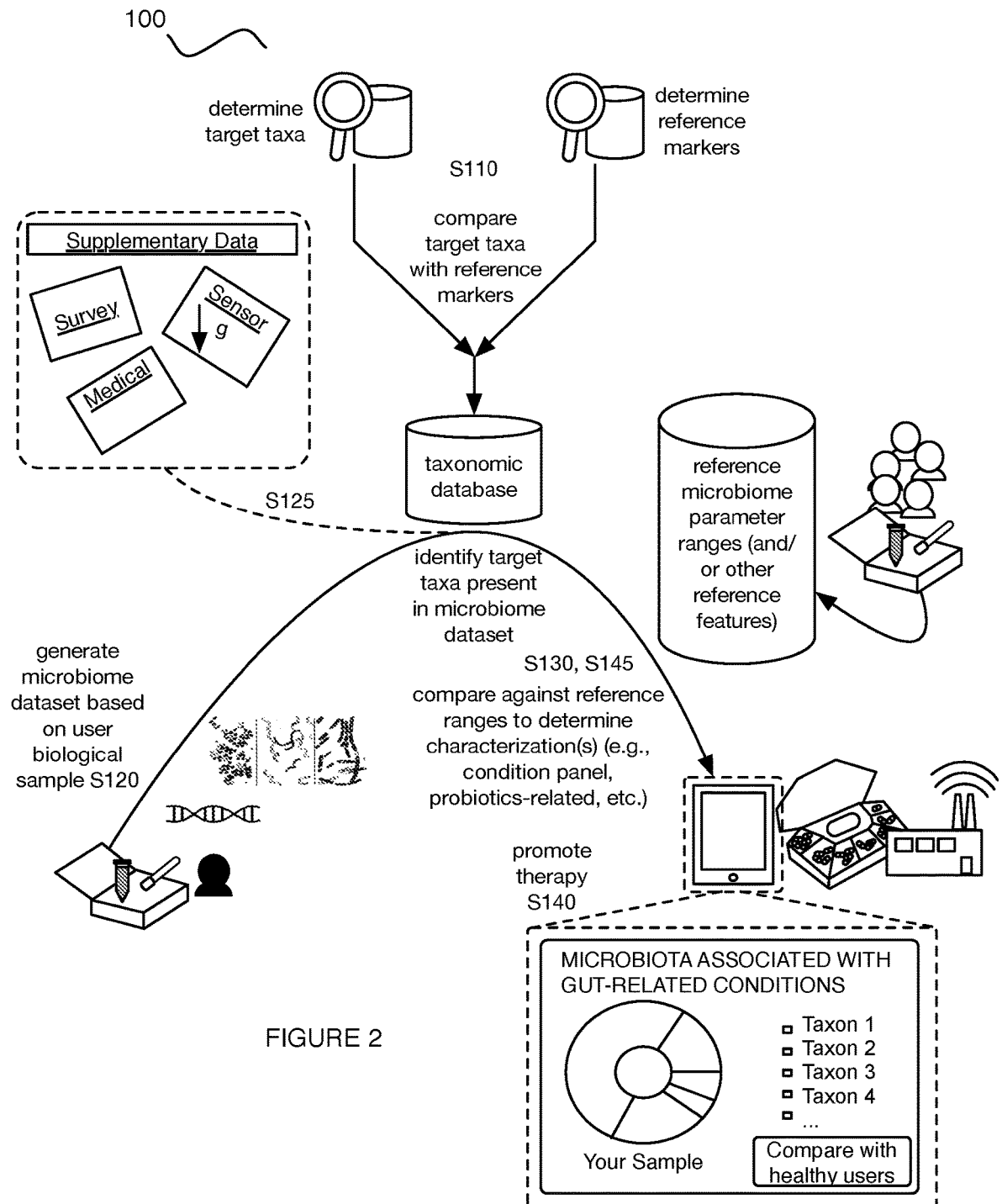
FIG. 2 is a flowchart representation of variations of an embodiment of a method for characterizing a panel of conditions.

As shown in FIGS. 1A-1B and 2, embodiments of a method 100 for characterizing a panel of conditions (e.g., gut-related conditions) based on processing a biological sample can include: generating a taxonomic database associated with markers for a plurality of taxa S110; generating a microbiome dataset (e.g., a microorganism sequence dataset including microorganism sequences, etc.) for a user based on a biological sample collected from the user S120; and/or performing a characterization process for at least one of microbiome composition, microbiome functional diversity, and/or associated conditions (e.g., determining a panel characterization for a panel of conditions), based on the taxonomic database and the microbiome datasets (and/or supplementary datasets and/or other suitable data) S130. The method 100 can additionally or alternatively include: collecting a supplementary dataset informative of the panel of conditions S125; promoting a therapy for the user based on the characterization process S140; determining a probiotics-related characterization S145; validating the characterization process S150; and/or any other suitable processes.

In variations, Blocks of the method 100 can be repeatedly performed in any suitable order to enable refining of the taxonomic database (e.g., through identifying new markers associated with different taxa and/or conditions, etc.), refining of the characterization process (e.g., through updating reference abundances used to compare against user relative abundances of targets for identifying clinically relevant results; through generation and updating of characterization models; through increasing the number of conditions that can be characterized using a single biological sample; etc.), the therapy process (e.g., through monitoring and modulating microbiome composition with therapies over time such as through iteratively performing Blocks S120 and S130 over time, where the therapies can be selected based on characterization results possessing sensitivity, specificity, precision, and negative predictive value; etc.), and/or other suitable processes.

One or more instances of the method 100 and/or processes described herein can be performed asynchronously (e.g., sequentially), concurrently (e.g., in parallel; multiplexing to enable processing of multiple biological samples in parallel; computationally characterizing different conditions concurrently on different threads for parallel computing to improve system processing ability; etc.), in temporal relation to a trigger event, and/or in any other suitable order at any suitable time and frequency by and/or using one or more instances of the system (e.g., including a sample handling network, a panel characterization system, a therapy system, sample kits, etc.), elements, and/or entities described herein.

Additionally or alternatively, data described herein (e.g., microorganism sequence data, microbiome features, characterizations such as panel characterizations and/or probiotics-related characterizations, population-level data; userlevel data; treatment-related data; etc.) can be associated with any suitable temporal indicators (e.g., seconds, minutes, hours, days, weeks, etc.; temporal indicators indicating when the data was collected, determined and/or otherwise processed; temporal indicators providing context to content described by the data, such as temporal indicators indicating a state of a panel of conditions at the time at which the biological sample was collected; etc.) and/or change in temporal indicators (e.g., microbiome features over time; microbiome composition diversity, functional diversity, and/or other suitable aspects over time; change in data; data patterns; data trends; data extrapolation and/or other prediction; etc.). However, the method can be performed in any suitable manner.

4.1 Method—Generating a Taxonomic Database.

Block S110 recites: generating one or more taxonomic databases associated with markers for a plurality of taxa, which can function to create a database including marker information suitable for comparison to user microorganism sequences in generating one or more characterizations.

Generating a taxonomic database S110 preferably includes determining a set of reference markers for the taxonomic database (e.g., based on predicted reads derived from primers selected based on a shared marker characteristic across a plurality of taxa; etc.); determining a target list of taxa (e.g., associated with gut-related conditions); filtering the target list of taxa based on a comparison (e.g., sequence comparison) against the reference markers (e.g., while using optimization parameters); and storing, at the taxonomic database, the filtered taxa (e.g., as shown in FIGS. 9A-9B) in association with corresponding reference markers.

Regarding Block S110, determining the set of reference markers is preferably based on one or more primers (e.g., primers to be used in amplification of genetic material from biological samples, as in Block S120, etc.). For example, Block S110 can include: predicting amplicons based on primers (e.g., V4 primers GTGCCAGCMGCCGCGGTAA for forward, and GGACTACHVGGGTWTCTAAT for reverse, etc.) allowing annealing satisfying a threshold condition (e.g., up to 2 mismatches over the entire sequence) for comparison to sequences from a reference database (e.g., SILVA database); filtering the amplicons based on degeneracy (e.g., filtering out degenerate amplicons that expand to more than 20 possible non-degenerate sequences); modifying the filtered amplicons to represent a forward read (e.g., including the forward primer and 125 bp to the 3' end of the forward primer, etc.) and a reverse read (e.g., including the reverse primer and 124 bp to the 3' end of the reverse primer, etc.); processing the modified amplicons (e.g., removing the primers); and storing the processed amplicons (e.g., the 125 bp after the forward read plus the 124 bp after the reverse read; in concatenated form; etc.) as reference markers. Additionally or alternatively, amplicon prediction, processing, and/or associated operations can be based on any suitable primers, and/or can be configured in any suitable manner for determining reference markers.

In relation to Block S110, determining a target list of taxa (e.g., a set of genera and a set of species associated with a set of conditions, etc.) preferably includes processing condition-related information sources (e.g., third-party information sources such as scientific literature, clinical tests, etc.; sources including information regarding conditions, associated microorganisms, and/or associated markers, etc.). In a variation, Block S110 can include manually processing condition-related information sources (e.g., with human curation of markers and/or associated information, etc.) to generate the target list of taxa. In another variation, Block S110 can include automatically processing condition-related information sources. For example, Block S110 can include: generating a list of online information sources; obtaining the online information sources based on the list; processing the online information sources to extract a set of taxa, associated conditions, and/or other associated data (e.g., through applying natural language processing techniques, etc.) for generating the target list of taxa.

Figure 6:
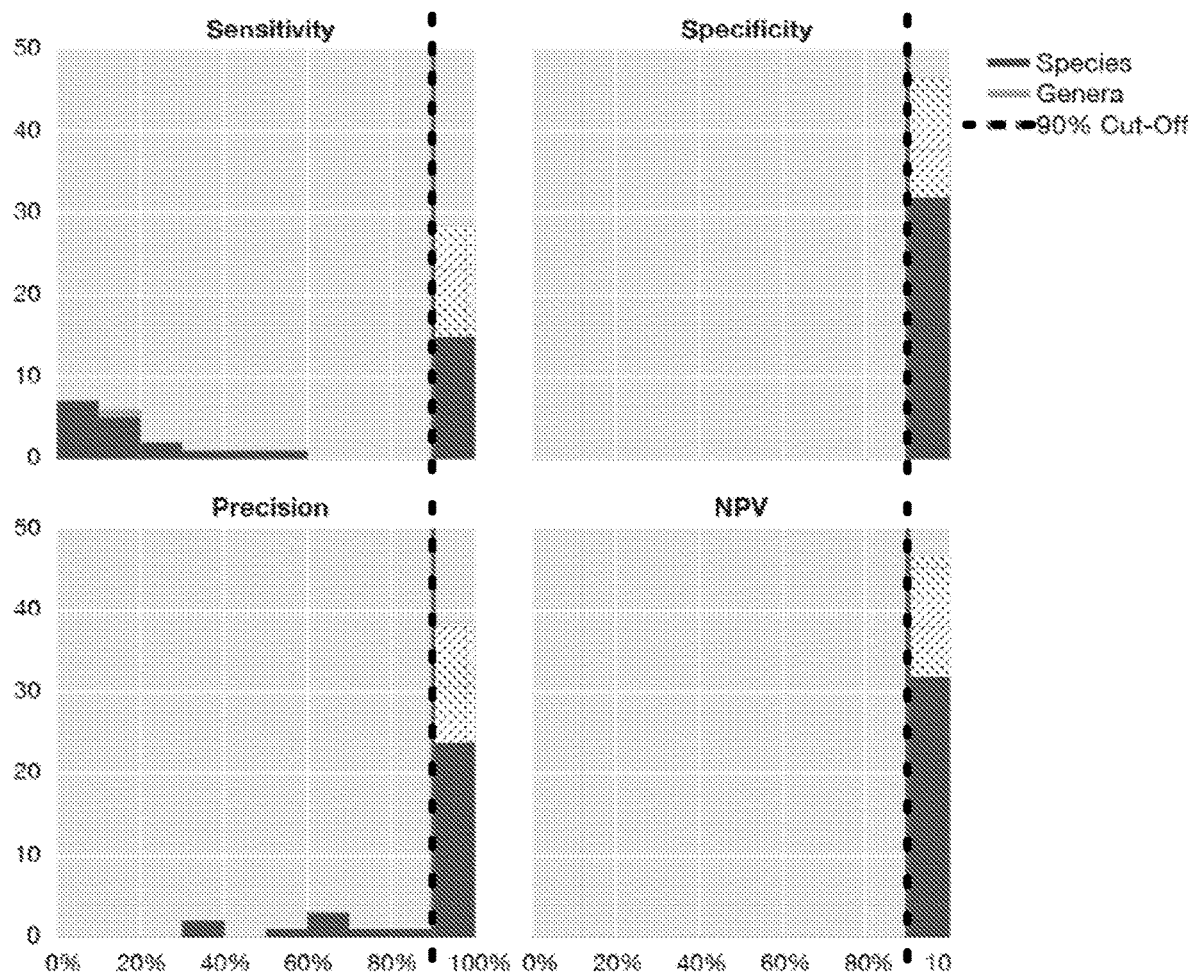
FIG. 6 is a chart representation of an example of optimization parameters for determining target taxa.

Determining the target list of taxa preferably includes filtering the target list of taxa based on a comparison with the set of reference markers. For example, Block S110 can include associating reference markers from the set of reference markers to taxa from the target list of taxa, such as based on a performing a sequence similarity search using 100% identity over 100% of the length of a genetic sequence associated with one or more taxa from the plurality of taxa (e.g., a 16S rRNA gene V4 region for a taxa), against the set of reference markers. However, any suitable identity parameter, length parameter, and/or other suitable parameters can be applied to a sequence similarity search, and associating reference markers with taxa can be performed in any suitable manner. Reference markers for different taxa of a preliminary target list are preferably filtered according to optimization parameters (e.g., optimizing for sensitivity, specificity, precision, negative predicting value, and/or other metrics, such as through using confusion matrices, etc.). In an example, as shown in FIGS. 6 and 9A-9B, taxa from the preliminary target list can be filtered based on an optimization parameter threshold (e.g., requiring each of the optimization parameters to exceed 90%; requiring precision of over 95%; etc.). In another example, Block S120 can include: generating a plurality of sub-databases associating a given taxa to different numbers of reference markers (e.g., sequences), resulting in different optimization parameter profiles. In a specific example, Block S110 can include: accepting a first subset of reference markers unambiguously corresponding to a taxa; ranking reference markers from a second subset of reference markers based on a quotient of dt/ti, where "ti" represents an annotation of the sequence to a taxa of interest, and "dt" represents an annotation of the sequence to a different taxa; generating a set of sub-databases for a taxa based on different quotient conditions (e.g., a sub-database optimized for specificity based on a quotient condition of 0; a sub-database optimized for identifying true positives based on a quotient condition of 100); determining sets of optimization parameters for the set of sub-databases; filtering the preliminary target list of taxa based on sub-databases for the taxa corresponding to optimization parameters satisfying the optimization parameter thresholds; and storing the filtered taxa in association with the corresponding reference markers at the taxonomic database. Additionally or alternatively, determining the target list of taxa can be performed in any suitable manner.

Regarding Block S110, additionally or alternatively, generating the taxonomic database can include identifying reference markers and associated taxa based on processing biological samples received from a population of users in relation to supplementary datasets received from the population of users (e.g., determining correlations with self-reported conditions for the users based on microbiome composition features and/or microbiome functional diversity features derived from biological samples collected from the users), but determining reference markers corresponding to target taxa can be performed in any suitable manner. However, generating a taxonomic database can be performed in any suitable manner.

4.2 Method—Generating Microbiome Datasets.

Block S120 recites: generating one or more microbiome datasets (e.g., a microorganism sequence dataset including microorganism sequences, etc.) for one or more users (e.g., a current subject for determining a panel characterization; a population of subjects for generating the taxonomic database; etc.) based on biological samples collected from the plurality of users. Block S120 functions to process biological samples collected from users in order to determine microorganism sequences that can be subsequently processed based on the taxonomic database (e.g., performing a sequence comparison between the microorganism sequences and genetic sequences stored at the taxonomic database) to determine characterizations for the users.

Block S120 can include any one or more of: lysing a biological sample (e.g., in conjunction with using stabilization buffer, etc.), disrupting membranes in cells of a biological sample, separation of undesired elements (e.g., RNA, proteins) from the biological sample (e.g., extracting microorganism DNA with a column-based approach using a liquid-handling robot, etc.), purification of nucleic acids (e.g., DNA) in a biological sample, amplification (e.g., with a library preparation system) of nucleic acids from the biological sample, further purification of amplified nucleic acids of the biological sample, sequencing of amplified nucleic acids of the biological sample (e.g., in a pair-end modality on a NextSeq platform to generate 2×150 bp pair-end sequences; etc.), and/or any other suitable sample processing operations, such as those described in relation to U.S. application Ser. No. 15/374,890 filed 9 Dec. 2016, which is incorporated in its entirety by this reference.

In variations of Block S120, amplification of purified nucleic acids can include one or more of: polymerase chain reaction (PCR)-based techniques (e.g., solid-phase PCR, RT-PCR, qPCR, multiplex PCR, touchdown PCR, nanoPCR, nested PCR, hot start PCR, etc.), helicase-dependent amplification (HDA), loop mediated isothermal amplification (LAMP), self-sustained sequence replication (3SR), nucleic acid sequence based amplification (NASBA), strand displacement amplification (SDA), rolling circle amplification (RCA), ligase chain reaction (LCR), and/or any other suitable amplification technique. In amplification of purified nucleic acids, the primers used are preferably selected to prevent or minimize amplification bias, and/or configured to amplify nucleic acid regions/sequences (e.g., of the 16S region, the 18S region, the ITS region, etc.) associated with markers stored in the taxonomic database (e.g., amplifying genetic sequences that can be compared to markers in the taxonomic database, in Block S130; amplifying genetic sequences corresponding to marker characteristics; amplifying genetic sequences informative taxonomically, phylogenetically, for diagnostics, for formulations such as for probiotic formulations; etc.), and/or configured for any other suitable purpose.

In an example in relation to Block S120, universal primers (e.g., a F27-R338 primer set for 16S RNA, a F515-R806 primer set for 16S RNA, etc.) configured to avoid amplification bias can be used in amplification. In a specific example, Block S120 can include amplifying 16S genes (e.g., genes coding for 16S rRNA) with universal V4 primers (e.g., 515F: GTGCCAGCMGCCGCGGTAA and 806R: GGACTACHVGGGTWTCTAAT), other suitable primers associated with variable (e.g., semi-conserved hypervariable regions, etc.) regions (e.g., V1-V8 regions), and/or any other suitable portions of RNA genes. In another example, Block S120 can include selecting primers associated with protein genes (e.g., coding for conserved protein gene sequences across a plurality of taxa, etc.). In another example, primers used in variations of Block S120 can additionally or alternatively include incorporated barcode sequences specific to each biological sample, which can facilitate identification of biological samples post-amplification. Selected primers can additionally or alternatively be associated with conditions, microbiome composition features (e.g., identified primers compatible with a genetic target corresponding to microbiome composition features associated with a group of taxa correlated with flatulence; genetic sequences from which relative abundance features are derived etc.), functional diversity features, supplementary features, and/or other suitable features. Primers can additionally or alternatively include adaptor regions configured to cooperate with sequencing techniques involving complementary adaptors (e.g., Illumina Sequencing). Primers (and/or other suitable molecules, markers, and/or biological material described herein) can possess any suitable size (e.g., sequence length, number of base pairs, conserved sequence length, variable region length, etc.). Additionally or alternatively, any suitable number of primers can be used in sample processing for performing characterizations (e.g., panel characterizations, probiotic-related characterizations, etc.), where the primers can be associated with any suitable number of targets, sequences, taxa, conditions, and/or other suitable aspects. Primers used in Block S120 and/or other suitable portions of the method 100 can be selected through processes described in Block S120 (e.g., primer selection based on parameters used in generating the taxonomic database) and/or any other suitable portions of the method 100. Additionally or alternatively, primers (and/or processes associated with primers) can include and/or be analogous to that described in U.S. application Ser. No. 14/919,614, filed 21 Oct. 2015. However, identification and or usage of primers can be configured in any suitable manner.

In variations, Block S120 can include, in relation to sequence reads, one or more of: filtering, trimming, appending, clustering, labeling (e.g., as the actual genetic sequence; as an error; etc.). In a specific example, Block S120 can include generating a set of reads based on amplification of the 16S gene; filtering the reads using an average Q-score>30; trimming primers and leading bases from the reads; appending forward and reverse reads; clustering using a distance of 1 nucleotide (e.g., with the Swarm algorithm); labeling the most abundant read sequence per cluster as the actual genetic sequence; for each cluster, assigning the most abundant read sequence with a count corresponding to the number of reads in the cluster; and, for each cluster, performing chimera removal on the most abundant read sequence (e.g., using a VSEARCH algorithm, etc.). However, sequencing can be performed in any suitable manner.

Any suitable processes described in Block S120 can be performed in a multiplex manner for any suitable number of biological samples. In an example, Block S120 can include barcoding a plurality of samples with forward and reverse indexes (e.g., unique combinations), sequencing the plurality of samples in a multiplex manner; and, after sequencing, demultiplexing the samples corresponding to different users (e.g., with a BCL2FASTQ algorithm, etc.). Additionally or alternatively, any number of instances of portions of Block S120 can be performed at any suitable time and frequency. However, Block S120 can be performed in any suitable manner analogous to U.S. application Ser. No. 15/374,890 filed 9 Dec. 2016, which is herein incorporated in its entirety by this reference, and/or can be performed in any suitable manner.

4.3 Method—Collecting a Supplementary Dataset.

Block S125 recites: receiving a supplementary dataset informative of a panel of conditions and/or probiotics-related information. Block S125 can function to acquire additional data associated with one or more users of a set of users, which can be used to train and/or validate the characterization process (e.g., characterization models) generated in Block S130, the therapy process (e.g., therapy models) in Block S140, and/or any other suitable processes. The supplementary dataset preferably includes survey-derived data, but can additionally or alternatively include any one or more of: diagnostic-related data (e.g., celiac disease testing, colonoscopy, sigmoidoscopy, lower GI series, upper GI endoscopy, upper GI series, virtual colonoscopy, etc.), contextual data derived from sensors and/or any other suitable components (e.g., components of the system 200, which can include treatment devices, user devices such as smartphones, wearable medical devices, etc.), medical data (e.g., current and historical medical data, such as antibiotics medical history), data informative of one or more conditions of a panel (e.g., indications of presence or absence of the conditions, associated diagnoses, associated treatments, progress over time, etc.), and/or any other suitable type of data. In variations of Block S125, the survey-derived data can provide physiological, demographic, and behavioral information in association with a subject. Additionally or alternatively, Block S125, can be performed in any manner analogous to U.S. application Ser. No. 14/919,614, filed 21 Oct. 2015, which is incorporated in its entirety by this reference. However processing supplementary datasets Block S125 can be performed in any suitable manner.

4.4 Method—Performing a Characterization Process.

Block S130 recites: performing a characterization process for at least one of microbiome composition, microbiome functional diversity, and/or associated conditions, based on the taxonomic database and the microbiome datasets. Block S130 can function to process microbiome datasets (e.g., generated in Block S120) in relation to the taxonomic database (e.g., generated in Block S110) to generate one or more characterizations for the users. Characterizations for the user can include any characterizations analogous to those described in U.S. application Ser. No. 15/374,890 filed 9 Dec. 2016, which is herein incorporated in its entirety by this reference (e.g., relative abundances of microbiome composition for different taxa in relation to different demographics of users; risk of conditions; associated trends over time; etc.).

Figure 8:
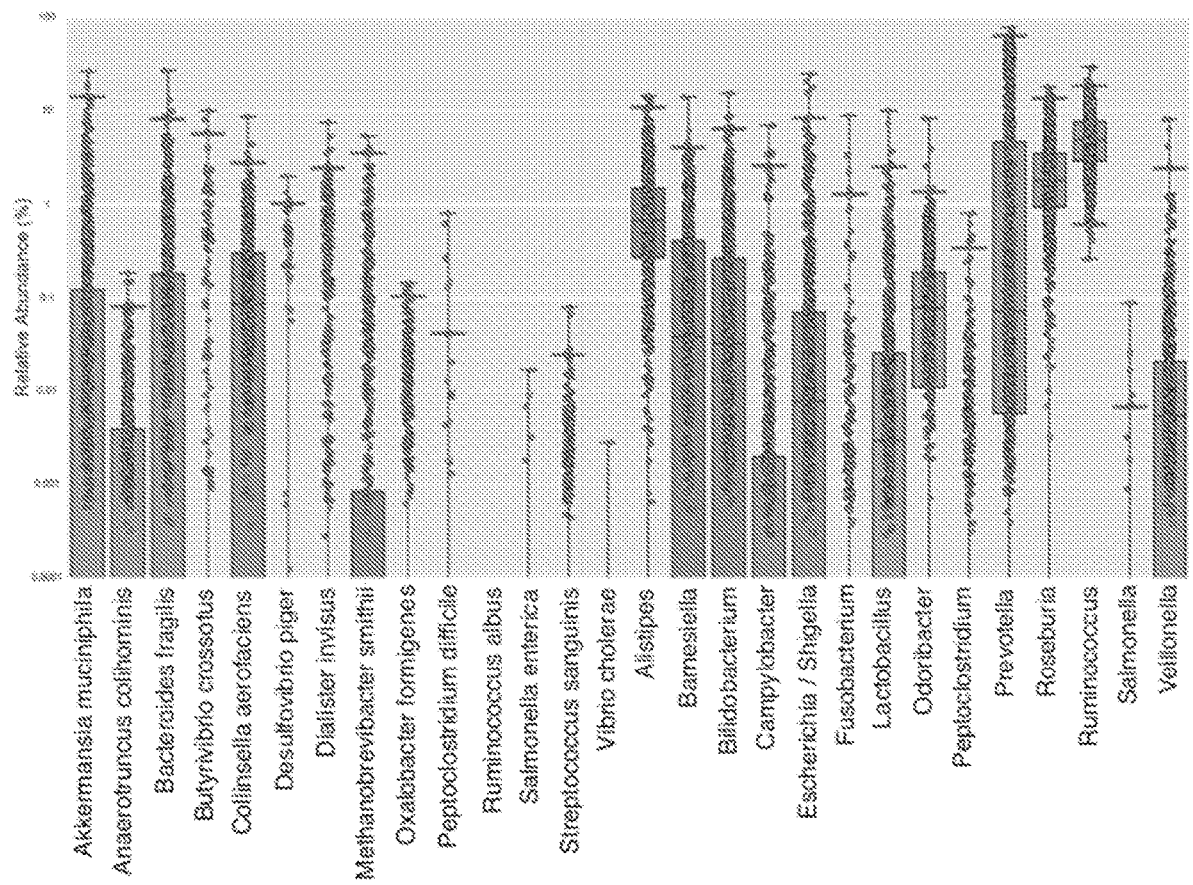
FIG. 8 is a chart representation of an example of healthy reference relative abundance ranges.

Block S130 can include one or more of: determining a reference microbiome parameter range (e.g., a healthy reference relative abundance range such as shown in FIG. 8, where the range can be associated with the absence of one or more conditions; a risky reference relative abundance range associated with the presence of and/or risk of one or more conditions; microorganism composition range for abundance of one or more taxa; microorganism functional diversity range for functional features associated with one or more taxa; etc.); determining a user microbiome parameter for a user; generating a characterization for the user based on a comparison between the user microbiome parameter and the reference microbiome parameter range (e.g., characterizing a user as possessing an unhealthy microbiome composition in relation to *Prevotella* based on the user microbiome parameter indicating a *Prevotella* abundance outside of the healthy reference range for *Prevotella*; etc.) and/or any other suitable operations. Reference microbiome parameter ranges can have any suitable lower- and upper-limits (e.g., a lower-limit above 0% for a relative abundance of *Ruminococcus*). Reference microbiome parameter ranges can include ranges representing any suitable confidence intervals (e.g., 99% confidence intervals across a population of users). In an example, reference relative abundance ranges can be calculated for any suitable taxa (e.g., from the target list of taxa), such as based on dividing the count of reads corresponding to that taxa by the total number of reads (e.g., total number of clustered and filtered reads); however, reference relative abundance ranges can be calculated in any suitable manner.

Block S130 preferably includes determining one or more panel characterizations for one or more panels of conditions (e.g., a panel of gut-related condition, etc.). Panel characterizations can include, for one or more conditions of the panel, one or more of: presence of conditions, absence of conditions, risk of conditions, severity of conditions, recommendations associated with the conditions, microbiome composition associated with the conditions (e.g., microbiome composition diversity including relative abundances of taxonomic groups associated with the conditions), microbiome functional diversity associated with the conditions, microbiome pharmacogenomics (e.g., pharmacogenomics profile of the user for potential efficacy of different antibiotics for the conditions) associated with the conditions, probiotics (e.g., sources, associated taxonomic groups, correlations, etc.) associated with the conditions, and/or any other suitable aspects related to panels of conditions.

In a variation of Block S130, determining reference microbiome parameter ranges can be performed empirically. For example, Block S130 can include collecting biological samples and supplementary datasets from a population of users. The population of users can include users associated with any suitable state of microbiome composition, microbiome functional diversity, conditions, and/or other suitable characteristics, where the supplementary datasets (e.g., digitally administered surveys at an application executing on mobile devices associated with the users) can be informative of the characteristics. In an example, the supplementary dataset can inform conditions including one or more of: cancer, infection, obesity, chronic health issues, mental health disorders, and/or any other suitable condition. In a specific example, the method 100 can include: processing biological samples from a population of healthy users (e.g., users never diagnosed with high blood sugar and/or diabetes, gut-related symptoms, and/or other conditions, etc.); processing the biological samples (e.g., as in Block S120) to determine microorganism sequences; determining relative abundance of each taxa (e.g., from the target list of taxa) for each user; and generating healthy ranges for each of the taxa based on the relative abundances across the population of healthy users. In another specific example, the method 100 can include: determining the set of reference relative abundance ranges for the set of taxa includes: collecting a set of supplementary biological samples and a set of supplementary datasets for a population of users; processing the set of supplementary biological samples to generate a supplementary microorganism sequence dataset using a set of primers associated with the panel of microorganism-related conditions; and determining the set of reference relative abundance ranges based on the supplementary microorganism sequence dataset and the set of supplementary datasets. However, empirically determining reference microbiome parameter ranges can be performed in any suitable manner. In another variation of Block S130, determining reference microbiome parameter ranges can be performed non-empirically, such as based on manually and/or automatically processing condition-related information sources. However, determining reference microbiome parameter ranges can be performed in any suitable manner.

Figure 4:
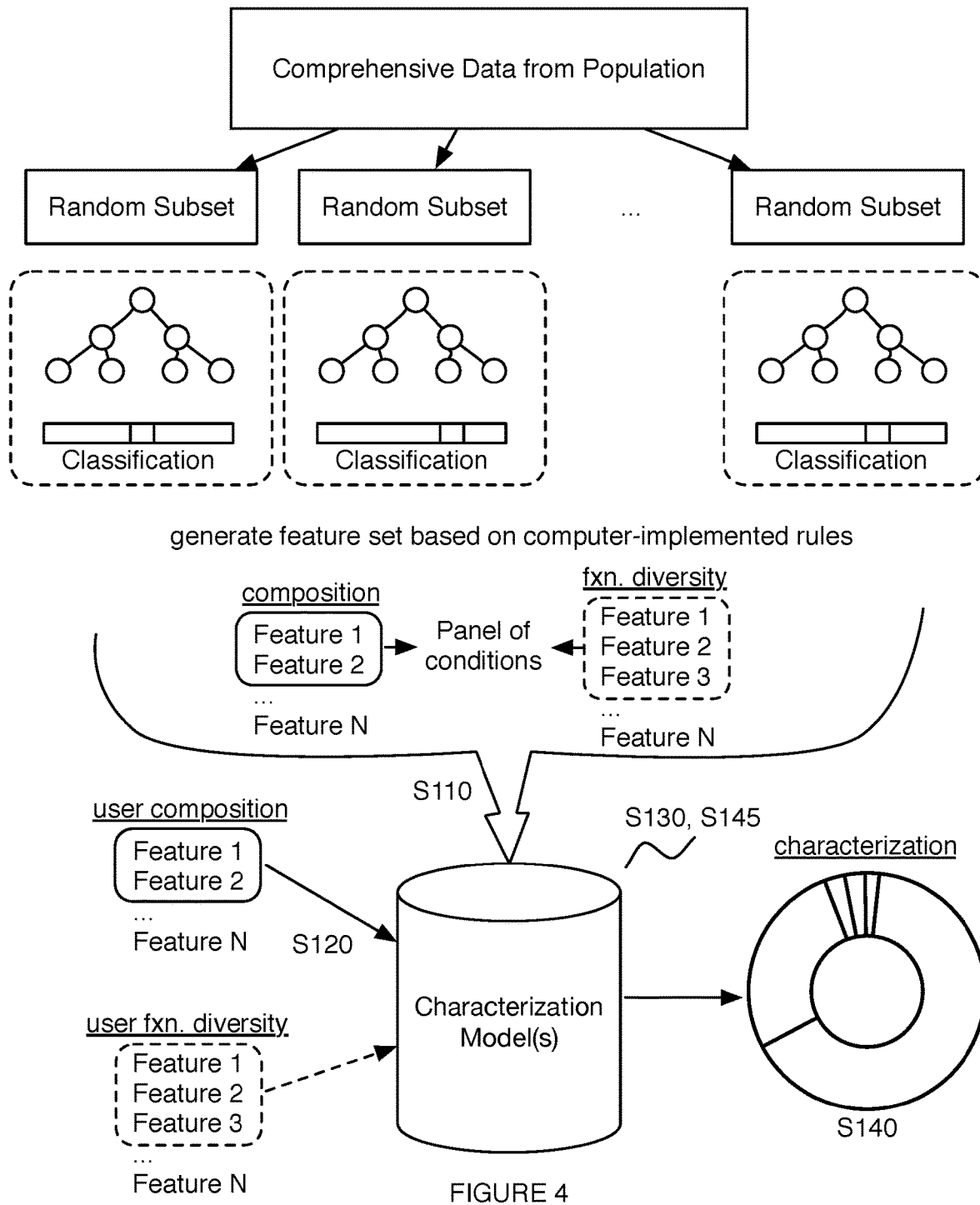
FIG. 4 is a schematic representation of variations of an embodiment of a method.

Regarding Block S130, determining a user microbiome parameter for a user is preferably based on generated microorganism sequences derived from biological samples of the user (e.g., as in Block S120; clustered and filtered reads; etc.). For example, determining a user microbiome parameter can include determining a relative abundance for different taxa (e.g., identified in the target list of taxa). In further examples, determining user microbiome parameters can include extracting panel-associated features (e.g., as shown in FIG. 4), which can include one or more of: microbiome composition features, microbiome functional features, microbiome pharmacogenomics features, and/or other suitable features associated with one or more conditions of the panel, such as in a manner analogous to U.S. application Ser. No. 15/374,890 filed 9 Dec. 2016, which is herein incorporated in its entirety by this reference. In an example, the method 100 can include: extracting a set of panel-associated features for the user based on the microorganism sequence dataset; determining a comparison between the reference features and the set of panel-associated features for the user; determining a panel characterization for the user for the panel of microorganism-related conditions based on the comparison. In a specific example, the method 100 can include: extracting a set of panel-associated features including extracting microbiome composition diversity features and microbiome functional diversity features of the set of panel-associated features based on the microorganism sequence dataset, and where determining the comparison includes determining the comparison of the reference features with the microbiome composition diversity features and the microbiome functional diversity features. In a specific example, the method 100 can include: determining reference microbiome parameter ranges from values of microbiome composition features and/or microbiome functional diversity features (e.g., derived from biological samples of healthy users, etc.); and comparing the user microbiome composition feature values and/or user microbiome functional diversity feature values to the reference microbiome parameter ranges to determine characterizations for the user (e.g., for conditions positively and/or negatively associated with the reference microbiome parameter ranges).

In relation to Block S130, comparing one or more user microbiome parameters to one or more reference microbiome parameter ranges associated with one or more characteristics (e.g., taxa, conditions, etc.) can include characterizing the user as possessing or not possessing the characteristic based on whether the user microbiome parameter values fall inside or outside the reference microbiome parameter ranges. For example, Block S130: can include deriving a healthy reference relative abundance range for a *Methanobrevibacter smithii*; and characterizing the user as at risk of irritable bowel syndrome in response to the user having a relative abundance of *Methanobrevibacter smithii* exceeding the healthy reference relative abundance range. In another example, determining a comparison between the reference features and a set of panel-associated features can include determining the set of panel-associated features as associated with at least one of: presence of microbiome composition features, absence of the microbiome composition features, relative abundance for taxonomic groups of the set of taxa, a ratio between at least two features associated with the set of taxa, interactions between the taxonomic groups, and phylogenetic distance between the taxonomic groups. In another example, generating the taxonomic database can include determining a set of reference relative abundance ranges for the set of taxa, where the set of reference relative abundance ranges is associated with the panel of microorganism-related conditions; extracting a set of user relative abundance ranges for the set of taxa based on a microorganism sequence dataset for the user; and determining a comparison between the set of reference relative abundance ranges and the set of user relative abundance ranges. In another example, determining a comparison between the reference features and the set of panel-associated features can include performing at least one of: a prediction analysis, multi hypothesis testing, a random forest test, and principal component analysis. However, comparing one or more user microbiome parameters can be performed in any suitable manner.

Additionally or alternatively for Block S130, performing the characterization process can be based on thresholds (e.g., determining risk of a panel of conditions based on relative abundances of a set of taxa in relation to a set of thresholds associated with the condition, etc.), weights (e.g., weighting relative abundance of a first taxa more heavily than relative abundance of a second taxa, such as when the first taxa has a greater correlation with the condition of interest, etc.), machine learning models (e.g., a classification model trained on microbiome features and corresponding labels for taxa stored in the taxonomic database; etc.), computer-implemented rules (e.g., feature-engineering rules for extracting microbiome features; model generation rules; user preference rules; microorganism sequence generation rules; sequence alignment rules; etc.), and/or any other suitable aspects.

Additionally or alternatively for Block S130, performing the characterization process can be configured as measuring at least one of the following: a risk score, and/or a significance index to associate a taxon or a set of taxa with a condition (or group of conditions) of interest in any manner analogous to that described in U.S. Provisional Application Ser. No. 62/558,489 filed 14 Sep. 2017, which is herein incorporated in its entirety by this reference. However, Block S130 can be performed in any suitable manner.

In variations, Block S130 and/or other suitable portions of the method 100 can include applying one or more models (e.g., panel characterization models; probiotics characterization models; therapy models; etc.) including one or more of: probabilistic properties, heuristic properties, deterministic properties, and/or any other suitable properties. Each model can be run or updated: once; at a predetermined frequency; every time an instance of an embodiment of the method and/or subprocess is performed; every time a trigger condition is satisfied (e.g., detection of audio activity in an audio dataset; detection of voice activity; detection of an unanticipated measurement; etc.), and/or at any other suitable time frequency. The module(s) can be run or updated concurrently with one or more other models, serially, at varying frequencies, and/or at any other suitable time. Each model can be validated, verified, reinforced, calibrated, or otherwise updated based on newly received, up-to-date data; historical data or be updated based on any other suitable data. Additionally or alternatively, models and/or associated aspects (e.g., approaches, algorithms, etc.) can be configured in any manner analogous to that described in U.S. application Ser. No. 15/374,890 filed 9 Dec. 2016, which is herein incorporated in its entirety by this reference. However, Block S130 can be performed in any suitable manner.

4.5 Method—Promoting a Therapy.

The method 100 can additionally or alternatively include Block S140, which recites: promoting a therapy based on the characterization process (e.g., based on panel characterizations, based on probiotics-related characterizations, based on features; etc.). Block S140 can function to determine, recommend, and/or provide a personalized therapy to the user, in order to modulate the microbiome composition and/or functional features of the user toward a desired equilibrium state, and/or to improve one or more conditions. For example, Block S140 can include promoting a probiotic consumable to the user based on the panel characterization (and/or probiotics-related characterization), where the probiotic consumable is operable to improve a plurality of the microorganism-related conditions of the panel of microorganism-related conditions. In another example, the method 100 can include collecting a diet-associated supplementary dataset associated with a dietary behavior of the user, where promoting the probiotic consumable includes promoting the probiotic consumable to the user based on the diet-associated supplementary dataset and the panel characterization (and/or probiotic characterization.

Therapies can include any one or more of: probiotics, consumables (e.g., food items, beverage items, etc.), topical therapies (e.g., lotions, ointments, antiseptics, etc.), nutritional supplements (e.g., vitamins, minerals, fiber, fatty acids, amino acids, prebiotics, etc.), medications, antibiotics, bacteriophages, and any other suitable therapeutic measure. Characterizations generated in Block S130 can be used to determine and/or promote a customized therapy, such as including formulation and regimen (e.g., dosage, usage instructions), to the user. For example, the method 100 can include: determining a user relative abundance for a taxa outside a health reference relative abundance range for the taxa; and promoting probiotics and/or other suitable therapies for modulating the microbiome composition of the user to achieve a user relative abundance within the health reference relative abundance range. As such, Block S140 can include determining and/or providing therapies configured to correct dysbiosis characteristics (e.g., identified based on characterizations determined in Block S130, etc.).

In variations, Block S140 can include determining and/or providing therapies with one or more therapy systems, which can include any one or more of: a communications system (e.g., to communicate therapy recommendations; to enable telemedicine; etc.; etc.), an application executable on a user device (e.g., gut-related condition application for promoting proper care of the gut, etc.), supplementary medical devices (e.g., treatment devices and/or diagnostic devices for gut-related conditions, medication dispensers, probiotic dispensers, etc.), user devices (e.g., including biometric sensors), and/or any other suitable component. As such, Block S140 can additionally or alternatively include generate control instructions and/or notifications for the therapy system for activating and/or otherwise operating the therapy system in association with promoting the therapy. However, using therapy systems for performing Block S140 can be performed in any suitable manner.

Figure 5:
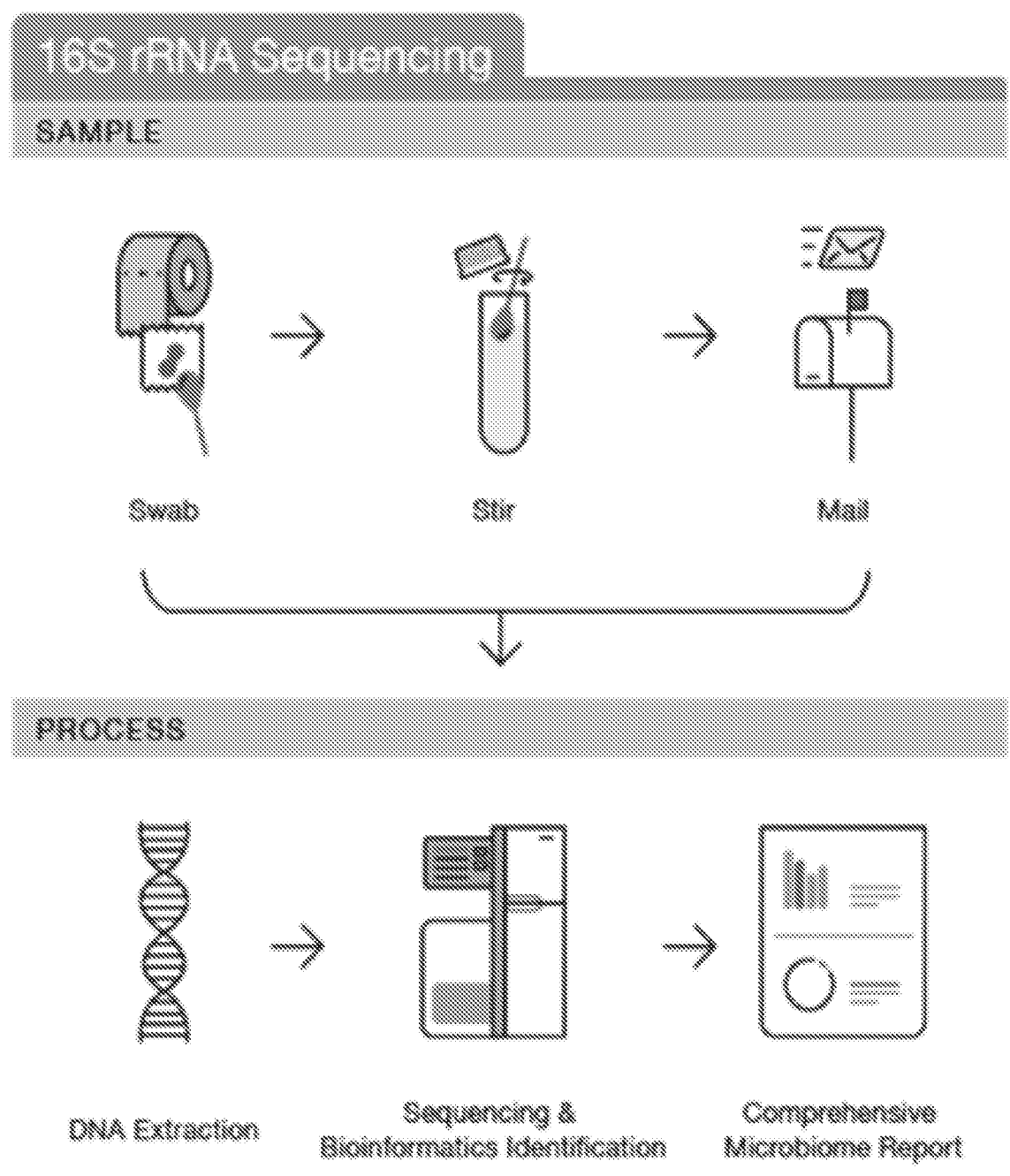
FIG. 5 is a schematic representation of processes in variations of a method for characterizing a panel of conditions.

In another variation, Block S140 can include generating and/or providing notifications (e.g., a microbiome report for a patient, as shown in FIG. 5) to a user regarding the therapies, the characterizations generated in Block S130, and/or any other suitable information. Types of notifications and manners of providing notifications can be analogous to that described in U.S. application Ser. No. 15/374,890 filed 9 Dec. 2016, which is incorporated in its entirety by this reference. However, Block S140 can be performed in any suitable manner.

4.6 Method—Determining a Probiotics-Related Characterization.

Figure 10:
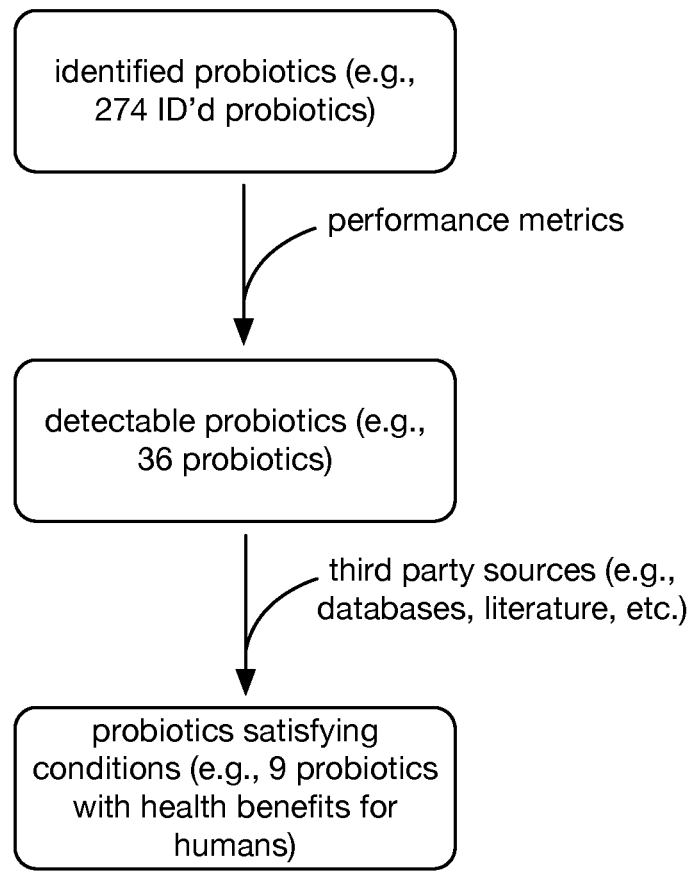
FIG. 10 is an example of selecting probiotics for characterizations.
Figure 12:
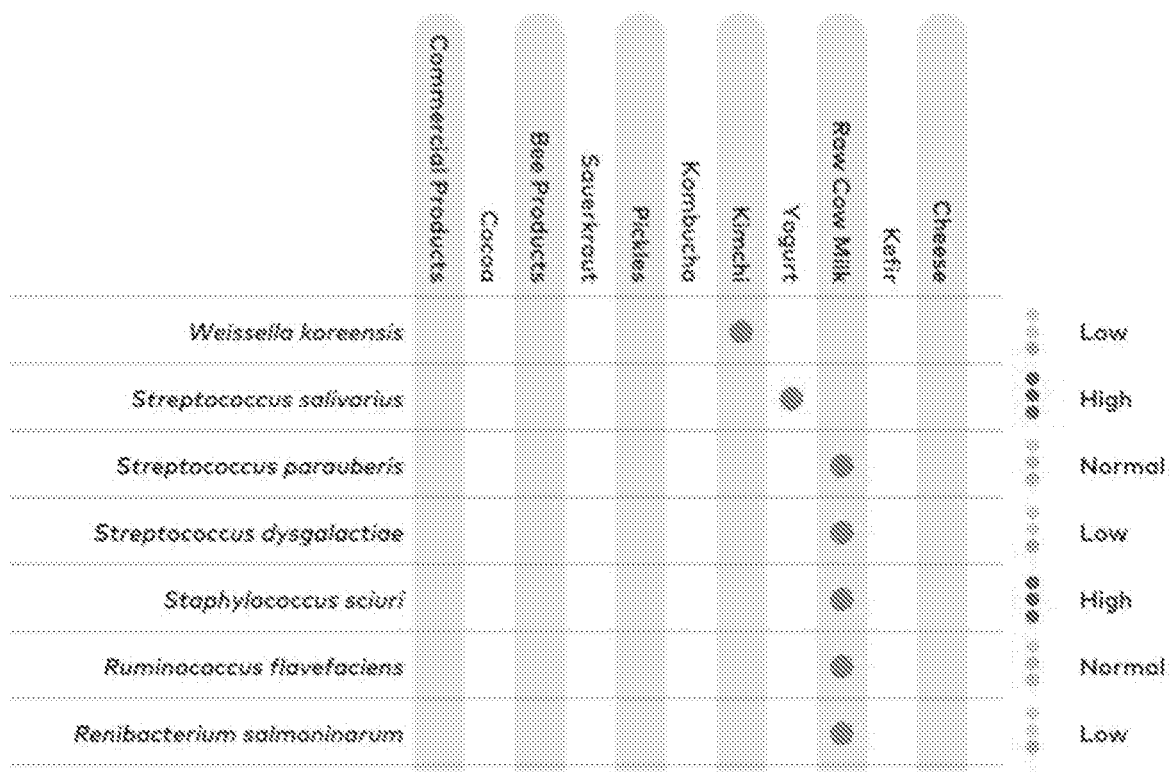
Figure 13A:
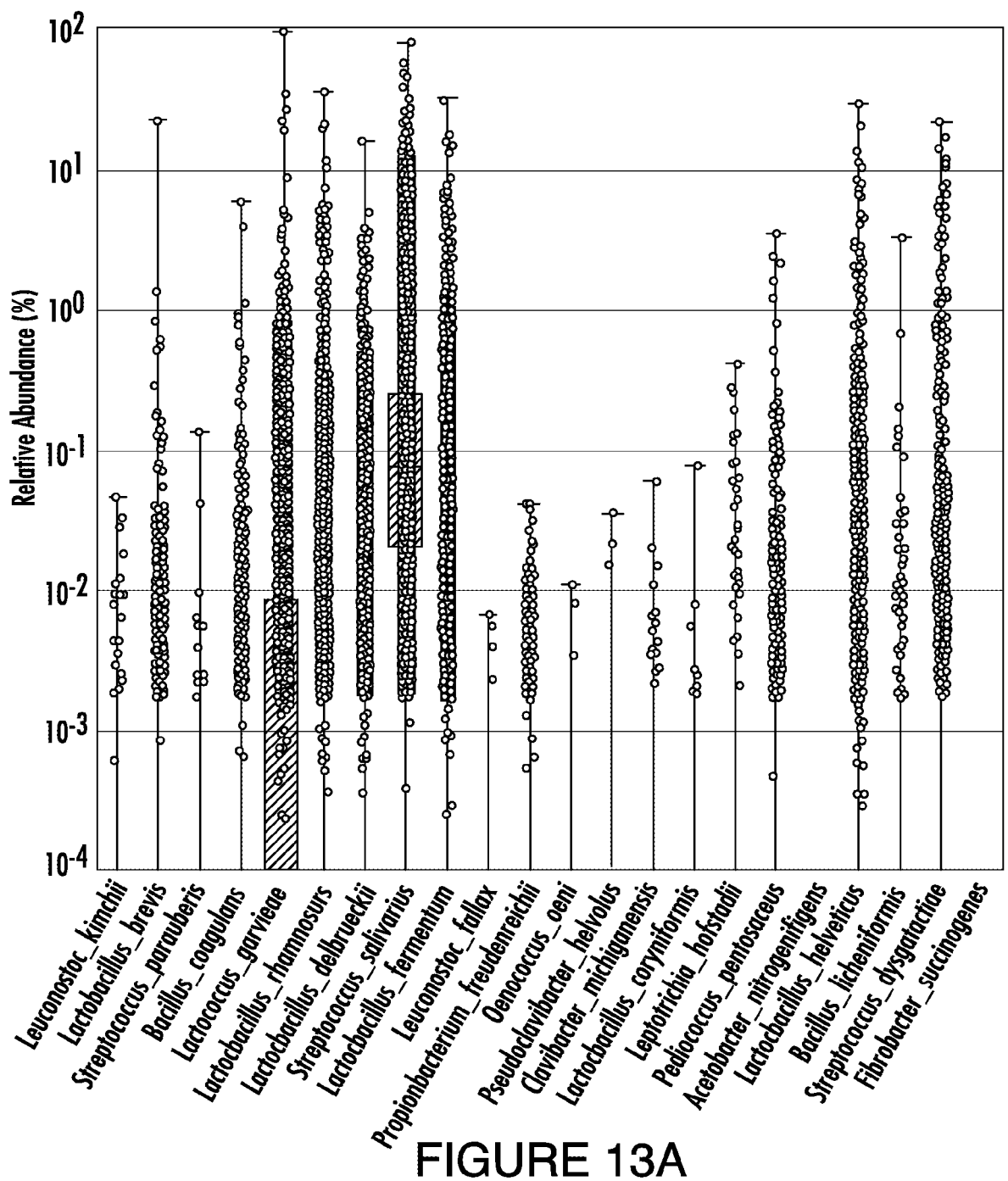
FIG. 13A-13B are examples of relative abundances associated with taxonomic groups related to probiotics.
Figure 13B:
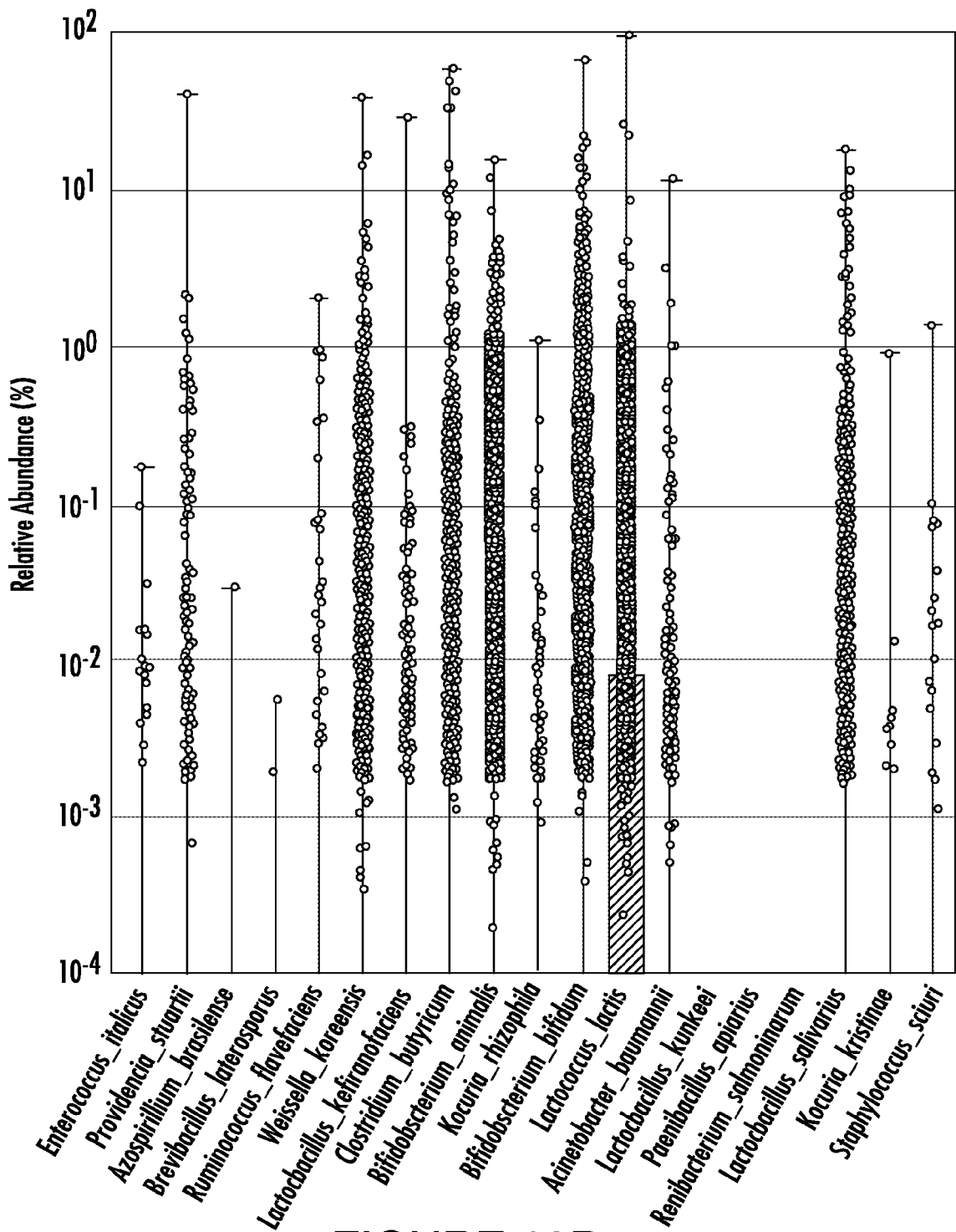

The method 100 can additionally or alternatively include Block S145: determining a probiotics-related characterization. Block S145 can function to process microbiome datasets (e.g., generated in Block S120) in relation to the taxonomic database (e.g., probiotics-related information included in the taxonomic database, etc.) to generate one or more probiotics-related characterizations for users. Additionally or alternatively, Block S145 can function to facilitate determination of panel characterizations upon which probiotic-related therapies can be based (e.g., determined and/or promoted). Block S145, as shown in FIG. 10, can include any one or more of: determining probiotic sources, determining taxonomic groups associated with probiotics, determining conditions (e.g., of a panel) associated with probiotics, generating characterizations describing probiotics-related information described herein and/or other suitable information, determining probiotics-related features (e.g., upon which characterizations and/or therapies can be based; etc.), and/or any other suitable processes. In a specific example, Block S145 can include: identifying potential probiotics; filtering the potential probiotics based on comparing characteristics of the probiotics to performance metrics associated with the probiotics; identifying probiotic-related conditions (e.g., health benefits, sources of probiotics, taxonomic groups associated with the probiotics); and performing a second filtering of the probiotics based on a comparison with the probiotic-related conditions. In another specific example, the method 100 can include: determining ranges (e.g., relative abundance ranges; healthy ranges; etc.) for probiotic strains (e.g., that can be identified reliably with analytical performance metrics, such as through performing one or more processes described herein); correlating the ranges (e.g., reference ranges) to one or more conditions; determining user ranges for a user; comparing the user ranges to the reference ranges; and/or determining therapies based on the comparisons. Taxonomic groups associated with probiotics can include any suitable taxonomic groups described herein (e.g., in relation to the taxonomic database, etc.). However, Block S145 can be performed in any suitable manner.

4.7 Method—Validating the Characterization Process.

Figure 7:
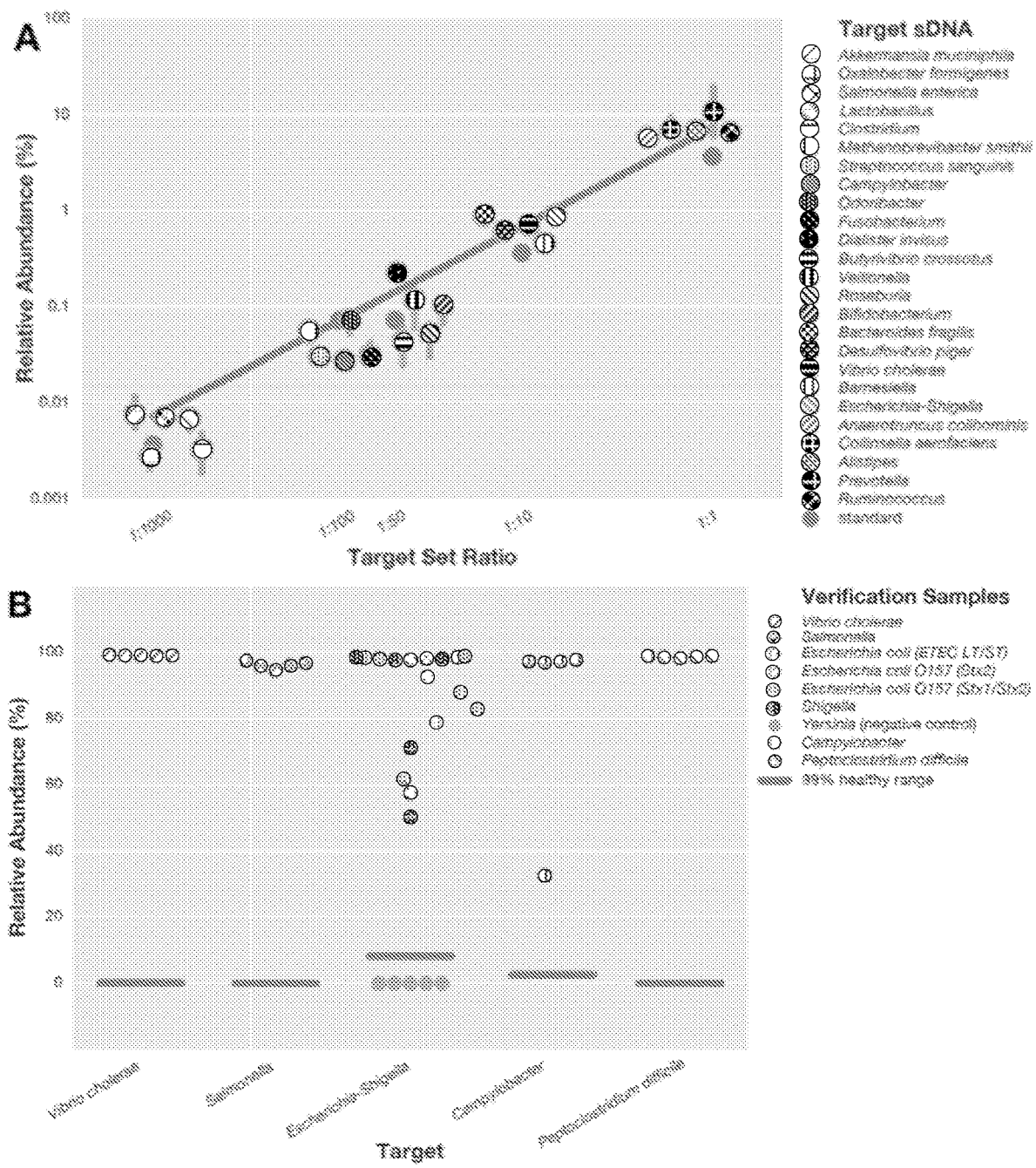
FIG. 7 is a graph representation of an example of validation of a characterization process.

The method 100 can additionally or alternatively include Block S150, which recites: validating the characterization process. Block S150 can function to validate the process used in generating one or more characterizations (e.g., as in Block S130) for a user based on microbiome datasets and the taxonomic database, in order to facilitate accurate determination of user microbiome parameters and/or reference microbiome parameter ranges (e.g., for relative abundances of a target taxa). Validating the characterization process preferably includes performing one or more of Blocks S110-S140 in relation to reference samples (e.g., with known microbiome composition and/or microbiome functional diversity, such as in relation to the target list of taxa, etc.). In a variation, Block S150 can include generating reference samples based on diluting genetic material (e.g., to any suitable ratio) associated with target taxa (e.g., synthetic genetic material such as synthetic double-stranded DNA representative of the V4 region of the 16S rRNA gene for different target taxa, as shown as "sDNA" in FIG. 7, etc.); and processing the reference samples by performing one or more of Blocks S110-S140 to verify detection of target taxa associated with the reference samples. In another variation, Block S150 can include processing reference samples derived from real or synthetic biological samples (e.g., stool samples with live or recombinant material of known composition, as shown as "Verification Samples" in FIG. 7; etc.) to verify detection of target taxa associated with the reference samples. Additionally or alternatively, Block S150 can include modifying one or more parameters of associated with one or more of Blocks S110-S140 based on the results of validating the characterization process. However, Block S150 can be performed in any suitable manner.

The method 100 and/or system of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a patient computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, though any suitable dedicated hardware device can (alternatively or additionally) execute the instructions.

The FIGURES illustrate the architecture, functionality and operation of possible implementations of compositions, methods, and systems according to preferred embodiments, example configurations, and variations thereof. It should also be noted that, in some alternative implementations, the functions noted can occur out of the order noted in the FIGURES. For example, aspects shown in succession may, in fact, be executed substantially concurrently, or the aspects may sometimes be executed in the reverse order, depending upon the functionality involved. The embodiments include every combination and permutation of the various system components and the various method processes, including any variations, examples, and specific examples. As a person skilled in the art will recognize from the previous detailed description and from the figures and claims, modifications and changes can be made to the embodiments without departing from the scope.

We claim:

1. A method for characterizing a panel of microorganism-related conditions associated with a set of taxa, the method comprising:

generating a taxonomic database comprising reference features associated with the set of taxa;

generating a microorganism sequence dataset for a user based on a biological sample collected from the user;

extracting a set of panel-associated features for the user based on the microorganism sequence dataset and by applying feature-selection rules;

determining a comparison between the reference features and the set of panel-associated features for the user;

determining a panel characterization for the user for the panel of microorganism-related conditions based on the comparison; and promoting a therapy for a microorganism-related condition of the panel of microorganism-related conditions, based on the panel characterization, collecting a diet-associated supplementary dataset associated with a dietary behavior of the user, wherein promoting the probiotic consumable comprises promoting the probiotic consumable to the user based on the diet-associated supplementary dataset and the panel characterization, wherein extracting the set of panel-associated features by applying the feature selection rules comprises extracting microbiome composition diversity features and microbiome functional diversity features of the set of panel-associated features based on the microorganism sequence dataset, and wherein determining the comparison comprises determining the comparison of the reference features with the microbiome composition diversity features and the microbiome functional diversity features, wherein promoting the therapy comprises promoting a probiotics-related therapy for the microorganism-related condition, wherein the probiotics-related therapy is associated with the set of taxa, and wherein the set of taxa comprises at least one of: *Bacillus coagulans* (species), *Bifidobacterium animalis* (species), *Clostridium butyricum* (species), *Lactobacillus brevis* (species), *Lactobacillus coryniformis* (species), *Lactobacillus fermentum* (species), *Lactobacillus helveticus* (species), *Lactobacillus rhamnosus* (species), and *Streptococcus salivarius* (species).

2. The method of claim 1, wherein the panel of microorganism-related conditions comprises a set of gut-related conditions associated with antibiotics, wherein extracting the set of panel-associated features comprises extracting microbiome pharmacogenomics features of the set of panel-associated features based on the microorganism sequence dataset, and wherein promoting the therapy comprises promoting an antibiotics-associated therapy for the set of gut-related conditions based on the microbiome pharmacogenomics features.

3. The method of claim 1, wherein determining the comparison between the reference features and the set of panel-associated features comprises determining the set of panel-associated features as associated with at least one of: presence of microbiome composition features, absence of the microbiome composition features, relative abundance for taxonomic groups of the set of taxa, diversity of microbiome composition including taxonomic and functional features, a ratio between at least two features associated with the set of taxa, interactions between the taxonomic groups, and phylogenetic distance between the taxonomic groups.

4. The method of claim 3, wherein generating the taxonomic database comprises determining a set of reference relative abundance ranges for the set of taxa, wherein the set of reference relative abundance ranges is associated with the panel of microorganism-related conditions, wherein extracting the set of panel-associated features comprises extracting a set of user relative abundance ranges for the set of taxa based on the microorganism sequence dataset, and wherein determining the comparison between the reference features and the set of panel-associated feature comprises determining the comparison between the set of reference relative abundance ranges and the set of user relative abundance ranges.

5. The method of claim 4, wherein determining the set of reference relative abundance ranges for the set of taxa comprises:

collecting a set of supplementary biological samples and a set of supplementary datasets for a population of users;

processing the set of supplementary biological samples to generate a supplementary microorganism sequence dataset using a set of primers associated with the panel of microorganism-related conditions; and determining the set of reference relative abundance ranges based on the supplementary microorganism sequence dataset and the set of supplementary datasets.

6. The method of claim 3, wherein determining the comparison between the reference features and the set of panel-associated features comprises performing at least one of: a prediction analysis, multi hypothesis testing, a random forest test, principal component analysis, significance index analysis, risk score analysis, and meta-analysis.

7. The method of claim 1, wherein the set of taxa further comprises at least one of: *Acetobacter nitrogenifigens* (species), *Azospirillum brasilense* (species), *Bacillus licheniformis* (species), *Bifidobacterium bifidum* (species), *Brevibacillus laterosporus* (species), *Clavibacter michiganensis* (species), *Enterococcus italicus* (species), *Kocuria rhizophila* (species), *Lactobacillus delbrueckii* (species), *Lactobacillus kefiranofaciens* (species), *Lactobacillus kunkeei* (species), *Lactobacillus salivarius* (species), *Lactococcus garvieae* (species), *Lactococcus lactis* (species), *Leptotrichia hofstadii* (species), *Leuconostoc fallax* (species), *Leuconostoc kimchii* (species), *Oenococcus oeni* (species), *Paenibacillus apiarius* (species), *Pediococcus pentosaceus* (species), *Propionibacterium freudenreichii* (species), *Pseudoclavibacter helvolus* (species), *Renibacterium salmoninarum* (species), *Ruminococcus flavefaciens* (species), *Staphylococcus sciuri* (species), *Streptococcus dysgalactiae* (species), *Streptococcus parauberis* (species), and *Weissella koreensis* (species).

8. The method of claim 1, wherein the panel of microorganism-related conditions comprises at least one of: Diarrhea, Irritable Bowel Syndrome (IBS), Inflammatory Bowel Disease (IBD), Crohn's Disease, Ulcerative Colitis, Constipation, Abdominal Tenderness, Bloating, Flatulence, Obesity, Type II Diabetes, Prediabetes, Kidney Stones, Cardiovascular health, and Anxiety.

9. The method of claim 1, wherein characterizing the panel of microorganism-related characterization comprises at least one of diagnosing and treating a gut-related panel of conditions.

* * * * *

SEQUENCE LISTING

<160> NUMBER OF SEQ ID NOS: 269

<210> SEQ ID NO 1
<211> LENGTH: 20
<212> TYPE: DNA
<213> ORGANISM: Unknown
<220> FEATURE:
<223> OTHER INFORMATION: Synthesized Degenerate Sequence

<400> SEQUENCE: 1
ccagcascyg cggtaattcc                                           20

<210> SEQ ID NO 2
<211> LENGTH: 18
<212> TYPE: DNA
<213> ORGANISM: Unknown
<220> FEATURE:
<223> OTHER INFORMATION: Synthesized Degenerate Sequence

<400> SEQUENCE: 2
actttcgttc ttgatyra                                             18

<210> SEQ ID NO 3
<211> LENGTH: 19
<212> TYPE: DNA
<213> ORGANISM: Unknown
<220> FEATURE:
<223> OTHER INFORMATION: Synthetic microbiome primer sequence

<400> SEQUENCE: 3
ccagcagctg cggtaattc                                            19

<210> SEQ ID NO 4
<211> LENGTH: 16
<212> TYPE: DNA
<213> ORGANISM: Unknown
<220> FEATURE:
<223> OTHER INFORMATION: Synthesized Synthetic Barcode Sequence -continued

<400> SEQUENCE: 4
tacgacggta cacagt                                                      16

<210> SEQ ID NO 5
<211> LENGTH: 18
<212> TYPE: DNA
<213> ORGANISM: Unknown
<220> FEATURE:
<223> OTHER INFORMATION: Synthesized Primer Sequence

<400> SEQUENCE: 5
tcgatcaaga acgaaagt                                                    18

<210> SEQ ID NO 6
<211> LENGTH: 20
<212> TYPE: DNA
<213> ORGANISM: Unknown
<220> FEATURE:
<223> OTHER INFORMATION: Synthesized Primer Sequence

<400> SEQUENCE: 6
tggtcattta gaggaagtaa                                                  20

<210> SEQ ID NO 7
<211> LENGTH: 18
<212> TYPE: DNA
<213> ORGANISM: Unknown
<220> FEATURE:
<223> OTHER INFORMATION: Synthesized Primer Sequence

<400> SEQUENCE: 7
tgcgttcttc atcgatgc                                                    18

<210> SEQ ID NO 8
<211> LENGTH: 20
<212> TYPE: DNA
<213> ORGANISM: Unknown
<220> FEATURE:
<223> OTHER INFORMATION: Synthesized Primer Sequence

<400> SEQUENCE: 8
tggtcattta gaggaagtaa                                                  20

<210> SEQ ID NO 9
<211> LENGTH: 16
<212> TYPE: DNA
<213> ORGANISM: Unknown
<220> FEATURE:
<223> OTHER INFORMATION: Synthesized Synthetic Barcode Sequence

<400> SEQUENCE: 9
tccgaaaggg ctttga                                                      16

<210> SEQ ID NO 10
<211> LENGTH: 18
<212> TYPE: DNA
<213> ORGANISM: Unknown
<220> FEATURE:
<223> OTHER INFORMATION: Synthesized Primer Sequence

<400> SEQUENCE: 10
gcatcgatga agaacgca                                                    18

```
<210> SEQ ID NO 11
<211> LENGTH: 19
<212> TYPE: DNA
<213> ORGANISM: Unknown
<220> FEATURE:
<223> OTHER INFORMATION: Synthesized Degenerate Primer Sequence

<400> SEQUENCE: 11
gtgccagcmg ccgcggtaa                                              19

<210> SEQ ID NO 12
<211> LENGTH: 20
<212> TYPE: DNA
<213> ORGANISM: Unknown
<220> FEATURE:
<223> OTHER INFORMATION: Synthesized Degenerate Primer Sequence

<400> SEQUENCE: 12
ggactachvg ggtwtctaat                                             20

<210> SEQ ID NO 13
<211> LENGTH: 20
<212> TYPE: DNA
<213> ORGANISM: Unknown
<220> FEATURE:
<223> OTHER INFORMATION: Synthesized Primer Sequence

<400> SEQUENCE: 13
agagtttgat cctggctcag                                             20

<210> SEQ ID NO 14
<211> LENGTH: 17
<212> TYPE: DNA
<213> ORGANISM: Unknown
<220> FEATURE:
<223> OTHER INFORMATION: Synthesized Primer Sequence

<400> SEQUENCE: 14
attaccgcgg ctgctgg                                                17

<210> SEQ ID NO 15
<211> LENGTH: 20
<212> TYPE: DNA
<213> ORGANISM: Unknown
<220> FEATURE:
<223> OTHER INFORMATION: Synthesized Primer Sequence

<400> SEQUENCE: 15
agagtttgat cctggctcag                                             20

<210> SEQ ID NO 16
<211> LENGTH: 15
<212> TYPE: DNA
<213> ORGANISM: Unknown
<220> FEATURE:
<223> OTHER INFORMATION: Synthesized synthetic barcode sequence

<400> SEQUENCE: 16
acccgtactt ctagt                                                  15

<210> SEQ ID NO 17
<211> LENGTH: 17
<212> TYPE: DNA
<213> ORGANISM: Unknown
<220> FEATURE:
<223> OTHER INFORMATION: Synthesized Primer Sequence
```

```
<400> SEQUENCE: 17
ccagcagccg cggtaat                                                    17

<210> SEQ ID NO 18
<211> LENGTH: 23
<212> TYPE: DNA
<213> ORGANISM: Unknown
<220> FEATURE:
<223> OTHER INFORMATION: Synthesized Fungal Primer Sequence

<400> SEQUENCE: 18
cttggtcatt tagaggaaag taa                                             23

<210> SEQ ID NO 19
<211> LENGTH: 20
<212> TYPE: DNA
<213> ORGANISM: Unknown
<220> FEATURE:
<223> OTHER INFORMATION: Synthesized Fungal Primer Sequence

<400> SEQUENCE: 19
gctgcgttct tcatcgatgc                                                 20

<210> SEQ ID NO 20
<211> LENGTH: 22
<212> TYPE: DNA
<213> ORGANISM: Unknown
<220> FEATURE:
<223> OTHER INFORMATION: Synthesized Bacteria and Archea 16s Primer
      Sequence

<400> SEQUENCE: 20
tcagagtttg atcctggctc ag                                              22

<210> SEQ ID NO 21
<211> LENGTH: 17
<212> TYPE: DNA
<213> ORGANISM: Unknown
<220> FEATURE:
<223> OTHER INFORMATION: Synthesized Bacteria and Archea 16s Primer
      Sequence

<400> SEQUENCE: 21
attaccgcgg ctgctgg                                                    17

<210> SEQ ID NO 22
<211> LENGTH: 22
<212> TYPE: DNA
<213> ORGANISM: Unknown
<220> FEATURE:
<223> OTHER INFORMATION: Synthesized Bacteria and Archea 16s Degenerate
      Primer Sequence

<400> SEQUENCE: 22
cgtgtgccag cmgccgcggt aa                                              22

<210> SEQ ID NO 23
<211> LENGTH: 22
<212> TYPE: DNA
<213> ORGANISM: Unknown
<220> FEATURE:
<223> OTHER INFORMATION: Synthesized Bacteria and Archea 16s Degenerate
      Primer Sequence

<400> SEQUENCE: 23
ccggactach vgggtwtcta at                                              22
```

```
<210> SEQ ID NO 24
<211> LENGTH: 20
<212> TYPE: DNA
<213> ORGANISM: Unknown
<220> FEATURE:
<223> OTHER INFORMATION: Synthesized Eukaryote 18s Degenerate Primer
      Sequence

<400> SEQUENCE: 24
ccagcascyg cggtaattcc                                              20

<210> SEQ ID NO 25
<211> LENGTH: 18
<212> TYPE: DNA
<213> ORGANISM: Unknown
<220> FEATURE:
<223> OTHER INFORMATION: Synthesized Eukaryote 18s Degenerate Primer
      Sequence

<400> SEQUENCE: 25
actttcgttc ttgatyra                                                18

<210> SEQ ID NO 26
<211> LENGTH: 20
<212> TYPE: DNA
<213> ORGANISM: Unknown
<220> FEATURE:
<223> OTHER INFORMATION: Synthesized Eukaryotic 18s Primer Sequence

<400> SEQUENCE: 26
ccagcascyg cggtaattcc                                              20

<210> SEQ ID NO 27
<211> LENGTH: 18
<212> TYPE: DNA
<213> ORGANISM: Unknown
<220> FEATURE:
<223> OTHER INFORMATION: Synthesized Eukaryotic 18s Primer Sequence

<400> SEQUENCE: 27
actttcgttc ttgatyra                                                18

<210> SEQ ID NO 28
<211> LENGTH: 22
<212> TYPE: DNA
<213> ORGANISM: Unknown
<220> FEATURE:
<223> OTHER INFORMATION: Synthesized Fungal Ribosomal ITS primer
      sequence

<400> SEQUENCE: 28
cttggtcatt tagaggaagt aa                                           22

<210> SEQ ID NO 29
<211> LENGTH: 20
<212> TYPE: DNA
<213> ORGANISM: Unknown
<220> FEATURE:
<223> OTHER INFORMATION: Synthesized Fungal Ribosomal ITS primer
      sequence

<400> SEQUENCE: 29
gctgcgttct tcatcgatgc                                              20
```

<210> SEQ ID NO 30
<211> LENGTH: 19
<212> TYPE: DNA
<213> ORGANISM: Unknown
<220> FEATURE:
<223> OTHER INFORMATION: Synthesized Bacterial Ribosomal 16S primer
      sequence

<400> SEQUENCE: 30
gtgccagcmg ccgcggtaa                                              19

<210> SEQ ID NO 31
<211> LENGTH: 20
<212> TYPE: DNA
<213> ORGANISM: Unknown
<220> FEATURE:
<223> OTHER INFORMATION: Synthesized Bacterial Ribosomal 16S primer
      sequence

<400> SEQUENCE: 31
ggactachvg ggtwtctaat                                             20

<210> SEQ ID NO 32
<211> LENGTH: 20
<212> TYPE: DNA
<213> ORGANISM: Unknown
<220> FEATURE:
<223> OTHER INFORMATION: Synthesized Bacterial Ribosomal 16S primer
      sequence

<400> SEQUENCE: 32
agagtttgat cctggctcag                                             20

<210> SEQ ID NO 33
<211> LENGTH: 17
<212> TYPE: DNA
<213> ORGANISM: Unknown
<220> FEATURE:
<223> OTHER INFORMATION: Synthesized Bacterial Ribosomal 16S primer
      sequence

<400> SEQUENCE: 33
attaccgcgg ctgctgg                                                17

<210> SEQ ID NO 34
<211> LENGTH: 17
<212> TYPE: DNA
<213> ORGANISM: Unknown
<220> FEATURE:
<223> OTHER INFORMATION: Synthesized Bacterial Ribosomal 16S primer
      sequence

<400> SEQUENCE: 34
cctacgggag gcagcag                                                17

<210> SEQ ID NO 35
<211> LENGTH: 18
<212> TYPE: DNA
<213> ORGANISM: Unknown
<220> FEATURE:
<223> OTHER INFORMATION: Synthesized Bacterial Ribosomal 16S primer
      sequence

<400> SEQUENCE: 35
ccgtcaattc mtttragt                                               18

```
<210> SEQ ID NO 36
<211> LENGTH: 19
<212> TYPE: DNA
<213> ORGANISM: Unknown
<220> FEATURE:
<223> OTHER INFORMATION: Synthesized Bacterial Ribosomal 16S primer
      sequence

<400> SEQUENCE: 36
caacgcgarg aaccttacc                                                       19

<210> SEQ ID NO 37
<211> LENGTH: 18
<212> TYPE: DNA
<213> ORGANISM: Unknown
<220> FEATURE:
<223> OTHER INFORMATION: Synthesized Bacterial Ribosomal 16S primer
      sequence

<400> SEQUENCE: 37
acaacacgag ctgacgac                                                        18

<210> SEQ ID NO 38
<211> LENGTH: 13
<212> TYPE: DNA
<213> ORGANISM: Unknown
<220> FEATURE:
<223> OTHER INFORMATION: Synthesized Bacterial Ribosomal 16S primer
      sequence

<400> SEQUENCE: 38
ggmttagata ccc                                                             13

<210> SEQ ID NO 39
<211> LENGTH: 15
<212> TYPE: DNA
<213> ORGANISM: Unknown
<220> FEATURE:
<223> OTHER INFORMATION: Synthesized Bacterial Ribosomal 16S primer
      sequence

<400> SEQUENCE: 39
crtacthchc aggyg                                                           15

<210> SEQ ID NO 40
<211> LENGTH: 17
<212> TYPE: DNA
<213> ORGANISM: Unknown
<220> FEATURE:
<223> OTHER INFORMATION: Synthesized Bacterial Ribosomal 16S primer
      sequence

<400> SEQUENCE: 40
cctacgggag gcagcag                                                         17

<210> SEQ ID NO 41
<211> LENGTH: 17
<212> TYPE: DNA
<213> ORGANISM: Unknown
<220> FEATURE:
<223> OTHER INFORMATION: Synthesized Bacterial Ribosomal 16S primer
      sequence

<400> SEQUENCE: 41
attaccgcgg ctgctgg                                                         17
```

```
<210> SEQ ID NO 42
<211> LENGTH: 30
<212> TYPE: DNA
<213> ORGANISM: Unknown
<220> FEATURE:
<223> OTHER INFORMATION: synthesized plant primer sequence

<400> SEQUENCE: 42
atgtcaccac aaacagagac taaagcaagt                                    30

<210> SEQ ID NO 43
<211> LENGTH: 21
<212> TYPE: DNA
<213> ORGANISM: Unknown
<220> FEATURE:
<223> OTHER INFORMATION: synthesized plant primer sequence

<400> SEQUENCE: 43
cttcttcagg tggaactcca g                                             21

<210> SEQ ID NO 44
<211> LENGTH: 20
<212> TYPE: DNA
<213> ORGANISM: Unknown
<220> FEATURE:
<223> OTHER INFORMATION: synthesized plant primer sequence

<400> SEQUENCE: 44
tcctccgctt attgatatgc                                               20

<210> SEQ ID NO 45
<211> LENGTH: 22
<212> TYPE: DNA
<213> ORGANISM: Unknown
<220> FEATURE:
<223> OTHER INFORMATION: synthesized plant primer sequence

<400> SEQUENCE: 45
cgatacttgg tgtgaattgc ag                                            22

<210> SEQ ID NO 46
<211> LENGTH: 20
<212> TYPE: DNA
<213> ORGANISM: Unknown
<220> FEATURE:
<223> OTHER INFORMATION: Synthesized euphausiid primer sequence

<400> SEQUENCE: 46
tttattgggg cgataaaaat                                               20

<210> SEQ ID NO 47
<211> LENGTH: 22
<212> TYPE: DNA
<213> ORGANISM: Unknown
<220> FEATURE:
<223> OTHER INFORMATION: Synthesized euphausiid primer sequence

<400> SEQUENCE: 47
tcgaggtcgy aatctttctt gt                                            22

<210> SEQ ID NO 48
<211> LENGTH: 20
<212> TYPE: DNA
<213> ORGANISM: Unknown
<220> FEATURE:
<223> OTHER INFORMATION: Synthesized mitochondrial 16s primer sequence
```

<400> SEQUENCE: 48
cccacatcaa ataccccta                                                    20

<210> SEQ ID NO 49
<211> LENGTH: 20
<212> TYPE: DNA
<213> ORGANISM: Unknown
<220> FEATURE:
<223> OTHER INFORMATION: Synthesized mitochondrial 16s primer sequence

<400> SEQUENCE: 49
gggtcattgg tggtcagaag                                                   20

<210> SEQ ID NO 50
<211> LENGTH: 21
<212> TYPE: DNA
<213> ORGANISM: Unknown
<220> FEATURE:
<223> OTHER INFORMATION: Synthesized Noto rDNA primer sequence

<400> SEQUENCE: 50
ccctatgaag cttyagacrt a                                                 21

<210> SEQ ID NO 51
<211> LENGTH: 23
<212> TYPE: DNA
<213> ORGANISM: Unknown
<220> FEATURE:
<223> OTHER INFORMATION: Synthesized Noto rDNA primer sequence

<400> SEQUENCE: 51
ccttgttgat awggtctcta aaa                                               23

<210> SEQ ID NO 52
<211> LENGTH: 26
<212> TYPE: DNA
<213> ORGANISM: Unknown
<220> FEATURE:
<223> OTHER INFORMATION: Synthesized synthesized amphipod 18S primer
      sequence

<400> SEQUENCE: 52
ctgcggttaa aaggctcgta gttgaa                                            26

<210> SEQ ID NO 53
<211> LENGTH: 24
<212> TYPE: DNA
<213> ORGANISM: Unknown
<220> FEATURE:
<223> OTHER INFORMATION: Synthesized synthesized amphipod 18S primer
      sequence

<400> SEQUENCE: 53
actgctttra gcactctgat ttac                                              24

<210> SEQ ID NO 54
<211> LENGTH: 30
<212> TYPE: DNA
<213> ORGANISM: Unknown
<220> FEATURE:
<223> OTHER INFORMATION: Synthesized cephalopod 28S primer sequence

<400> SEQUENCE: 54
cgccgaatcc cgtcgcmagt aaamggcttc                                        30

```
<210> SEQ ID NO 55
<211> LENGTH: 26
<212> TYPE: DNA
<213> ORGANISM: Unknown
<220> FEATURE:
<223> OTHER INFORMATION: Synthesized cephalopod 28S primer sequence

<400> SEQUENCE: 55
ccaagcaacc cgactctcgg atcgaa                                            26

<210> SEQ ID NO 56
<211> LENGTH: 15
<212> TYPE: DNA
<213> ORGANISM: Unknown
<220> FEATURE:
<223> OTHER INFORMATION: Synthesized all prey 16S primer sequence

<400> SEQUENCE: 56
gacgakaaga cccta                                                        15

<210> SEQ ID NO 57
<211> LENGTH: 22
<212> TYPE: DNA
<213> ORGANISM: Unknown
<220> FEATURE:
<223> OTHER INFORMATION: Synthesized all prey 16S primer sequence

<400> SEQUENCE: 57
cgctgttatc cctadrgtaa ct                                                22

<210> SEQ ID NO 58
<211> LENGTH: 17
<212> TYPE: DNA
<213> ORGANISM: Unknown
<220> FEATURE:
<223> OTHER INFORMATION: Synthesized green plants primer sequence

<400> SEQUENCE: 58
gggcaatcct gagccaa                                                      17

<210> SEQ ID NO 59
<211> LENGTH: 22
<212> TYPE: DNA
<213> ORGANISM: Unknown
<220> FEATURE:
<223> OTHER INFORMATION: Synthesized green plants primer sequence

<400> SEQUENCE: 59
ccattgagtc tctgcaccta tc                                                22

<210> SEQ ID NO 60
<211> LENGTH: 26
<212> TYPE: DNA
<213> ORGANISM: Unknown
<220> FEATURE:
<223> OTHER INFORMATION: Synthesized land plants primer sequence

<400> SEQUENCE: 60
atgtcaccac caacagagac taaagc                                            26

<210> SEQ ID NO 61
<211> LENGTH: 21
<212> TYPE: DNA
<213> ORGANISM: Unknown
<220> FEATURE:
<223> OTHER INFORMATION: Synthesized land plants primer sequence
```

<400> SEQUENCE: 61
cttcttcagg tggaactcca g                                      21

<210> SEQ ID NO 62
<211> LENGTH: 22
<212> TYPE: DNA
<213> ORGANISM: Unknown
<220> FEATURE:
<223> OTHER INFORMATION: Synthesized land plants primer sequence

<400> SEQUENCE: 62
gttatgcatg aacgtaatgc tc                                     22

<210> SEQ ID NO 63
<211> LENGTH: 21
<212> TYPE: DNA
<213> ORGANISM: Unknown
<220> FEATURE:
<223> OTHER INFORMATION: Synthesized land plants primer sequence

<400> SEQUENCE: 63
cgcgcatggt ggattcacaa t                                      21

<210> SEQ ID NO 64
<211> LENGTH: 18
<212> TYPE: DNA
<213> ORGANISM: Unknown
<220> FEATURE:
<223> OTHER INFORMATION: Synthesized vertebrates 12s primer sequence

<400> SEQUENCE: 64
tagaacaggc tcctctag                                          18

<210> SEQ ID NO 65
<211> LENGTH: 18
<212> TYPE: DNA
<213> ORGANISM: Unknown
<220> FEATURE:
<223> OTHER INFORMATION: Synthesized vertebrates 12s primer sequence

<400> SEQUENCE: 65
ttagataccc cactatgc                                          18

<210> SEQ ID NO 66
<211> LENGTH: 20
<212> TYPE: DNA
<213> ORGANISM: Unknown
<220> FEATURE:
<223> OTHER INFORMATION: Synthesized chordata 16s primer sequence

<400> SEQUENCE: 66
cgagaagacc ctrtggagct                                        20

<210> SEQ ID NO 67
<211> LENGTH: 19
<212> TYPE: DNA
<213> ORGANISM: Unknown
<220> FEATURE:
<223> OTHER INFORMATION: Synthesized chordata 16s primer sequence

<400> SEQUENCE: 67
ggattgcgct gttatccct                                         19

```
<210> SEQ ID NO 68
<211> LENGTH: 20
<212> TYPE: DNA
<213> ORGANISM: Unknown
<220> FEATURE:
<223> OTHER INFORMATION: Synthesized chordata 16s primer sequence

<400> SEQUENCE: 68
cgagaagacc ctrtggagct                                               20

<210> SEQ ID NO 69
<211> LENGTH: 16
<212> TYPE: DNA
<213> ORGANISM: Unknown
<220> FEATURE:
<223> OTHER INFORMATION: Synthesized chordata 16s primer sequence
<220> FEATURE:
<221> NAME/KEY: misc_feature
<222> LOCATION: (4)..(4)
<223> OTHER INFORMATION: n is a, c, g, or t

<400> SEQUENCE: 69
cctnggtcgc cccaac                                                   16

<210> SEQ ID NO 70
<211> LENGTH: 30
<212> TYPE: DNA
<213> ORGANISM: Unknown
<220> FEATURE:
<223> OTHER INFORMATION: Synthesized insecta COI primer sequence

<400> SEQUENCE: 70
agatattgga acwttatatt ttattttggg                                    30

<210> SEQ ID NO 71
<211> LENGTH: 24
<212> TYPE: DNA
<213> ORGANISM: Unknown
<220> FEATURE:
<223> OTHER INFORMATION: Synthesized insecta COI primer sequence

<400> SEQUENCE: 71
wactaatcaa ttwccaaatc ctcc                                          24

<210> SEQ ID NO 72
<211> LENGTH: 21
<212> TYPE: DNA
<213> ORGANISM: Unknown
<220> FEATURE:
<223> OTHER INFORMATION: Synthesized lumbricidae 12S primer sequence

<400> SEQUENCE: 72
tgtgtactgc cgtcgtaagc a                                             21

<210> SEQ ID NO 73
<211> LENGTH: 20
<212> TYPE: DNA
<213> ORGANISM: Unknown
<220> FEATURE:
<223> OTHER INFORMATION: Synthesized lumbricidae 12S primer sequence

<400> SEQUENCE: 73
aagagcgacg ggcgatgtgt                                               20
```

```
<210> SEQ ID NO 74
<211> LENGTH: 22
<212> TYPE: DNA
<213> ORGANISM: Unknown
<220> FEATURE:
<223> OTHER INFORMATION: Synthesized 16S primer sequence

<400> SEQUENCE: 74
ccggtctgaa ctcagatcac gt                                            22

<210> SEQ ID NO 75
<211> LENGTH: 20
<212> TYPE: DNA
<213> ORGANISM: Unknown
<220> FEATURE:
<223> OTHER INFORMATION: Synthesized 16S primer sequence

<400> SEQUENCE: 75
cgcctgttta tcaaaaacat                                               20

<210> SEQ ID NO 76
<211> LENGTH: 20
<212> TYPE: DNA
<213> ORGANISM: Unknown
<220> FEATURE:
<223> OTHER INFORMATION: Synthesized papillomavirus primer sequence

<400> SEQUENCE: 76
cgtccmarrg gawactgatc                                               20

<210> SEQ ID NO 77
<211> LENGTH: 20
<212> TYPE: DNA
<213> ORGANISM: Unknown
<220> FEATURE:
<223> OTHER INFORMATION: Synthesized papillomavirus primer sequence

<400> SEQUENCE: 77
gcmcagggwc ataayaatgg                                               20

<210> SEQ ID NO 78
<211> LENGTH: 27
<212> TYPE: DNA
<213> ORGANISM: Unknown
<220> FEATURE:
<223> OTHER INFORMATION: Synthesized coronavirus primer sequence

<400> SEQUENCE: 78
gggawgggat tacmcaaart gygaymg                                       27

<210> SEQ ID NO 79
<211> LENGTH: 24
<212> TYPE: DNA
<213> ORGANISM: Unknown
<220> FEATURE:
<223> OTHER INFORMATION: Synthesized coronavirus primer sequence
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 79
cccasaagwt gtaccnccng gytt                                          24
```

```
<210> SEQ ID NO 80
<211> LENGTH: 24
<212> TYPE: DNA
<213> ORGANISM: Unknown
<220> FEATURE:
<223> OTHER INFORMATION: Synthesized Epstein Barr virus primer sequence

<400> SEQUENCE: 80
gktagacttt gccagcytst accc                                          24

<210> SEQ ID NO 81
<211> LENGTH: 24
<212> TYPE: DNA
<213> ORGANISM: Unknown
<220> FEATURE:
<223> OTHER INFORMATION: Synthesized Epstein Barr virus primer sequence

<400> SEQUENCE: 81
gggagtcmgt gtcsccgtak atga                                          24

<210> SEQ ID NO 82
<211> LENGTH: 36
<212> TYPE: DNA
<213> ORGANISM: Unknown
<220> FEATURE:
<223> OTHER INFORMATION: Synthesized papillomavirus primer sequence
<220> FEATURE:
<221> NAME/KEY: misc_feature
<222> LOCATION: (30)..(30)
<223> OTHER INFORMATION: n is a, c, g, or t

<400> SEQUENCE: 82
gagcttataa acacagttat tgaggayggn gayatg                             36

<210> SEQ ID NO 83
<211> LENGTH: 32
<212> TYPE: DNA
<213> ORGANISM: Unknown
<220> FEATURE:
<223> OTHER INFORMATION: Synthesized papillomavirus primer sequence
<220> FEATURE:
<221> NAME/KEY: misc_feature
<222> LOCATION: (24)..(24)
<223> OTHER INFORMATION: n is a, c, g, or t

<400> SEQUENCE: 83
aacagttgat tgtcccagca gaynacrttr tt                                 32

<210> SEQ ID NO 84
<211> LENGTH: 15
<212> TYPE: DNA
<213> ORGANISM: Unknown
<220> FEATURE:
<223> OTHER INFORMATION: Synthesized enterovirus primer sequence

<400> SEQUENCE: 84 tccggccccct gaatg                                                   15

<210> SEQ ID NO 85
<211> LENGTH: 18
<212> TYPE: DNA
<213> ORGANISM: Unknown
<220> FEATURE:
<223> OTHER INFORMATION: Synthesized enterovirus primer sequence

<400> SEQUENCE: 85
caccggatgg ccaatcca                                                 18
```

```
<210> SEQ ID NO 86
<211> LENGTH: 20
<212> TYPE: DNA
<213> ORGANISM: Unknown
<220> FEATURE:
<223> OTHER INFORMATION: Synthesized influenza A primer sequence

<400> SEQUENCE: 86
cagattgctg actcccagca                                               20

<210> SEQ ID NO 87
<211> LENGTH: 23
<212> TYPE: DNA
<213> ORGANISM: Unknown
<220> FEATURE:
<223> OTHER INFORMATION: Synthesized influenza A primer sequence

<400> SEQUENCE: 87
gaccagcact ggagctagga tga                                           23

<210> SEQ ID NO 88
<211> LENGTH: 25
<212> TYPE: DNA
<213> ORGANISM: Unknown
<220> FEATURE:
<223> OTHER INFORMATION: Synthesized adenovirus primer sequence

<400> SEQUENCE: 88
gccgcagtgg tcttacatgc acatc                                         25

<210> SEQ ID NO 89
<211> LENGTH: 23
<212> TYPE: DNA
<213> ORGANISM: Unknown
<220> FEATURE:
<223> OTHER INFORMATION: Synthesized adenovirus primer sequence

<400> SEQUENCE: 89
cagcacgccg cggatgtcaa agt                                           23

<210> SEQ ID NO 90
<211> LENGTH: 20
<212> TYPE: DNA
<213> ORGANISM: Unknown
<220> FEATURE:
<223> OTHER INFORMATION: Synthesized cytomegalovirus primer sequence

<400> SEQUENCE: 90
gttctctcgt ctcctccgtg                                               20

<210> SEQ ID NO 91
<211> LENGTH: 20
<212> TYPE: DNA
<213> ORGANISM: Unknown
<220> FEATURE:
<223> OTHER INFORMATION: Synthesized cytomegalovirus primer sequence

<400> SEQUENCE: 91
cctgtggagc tcgttagagg                                               20

<210> SEQ ID NO 92
<211> LENGTH: 18
<212> TYPE: DNA
<213> ORGANISM: Unknown
<220> FEATURE:
<223> OTHER INFORMATION: Synthesized EBV primer sequence
```

```
<400> SEQUENCE: 92
gagggtggtt tggaaagc                                                    18

<210> SEQ ID NO 93
<211> LENGTH: 22
<212> TYPE: DNA
<213> ORGANISM: Unknown
<220> FEATURE:
<223> OTHER INFORMATION: Synthesized EBV primer sequence

<400> SEQUENCE: 93
aacagacaat ggactccctt ag                                               22

<210> SEQ ID NO 94
<211> LENGTH: 20
<212> TYPE: DNA
<213> ORGANISM: Unknown
<220> FEATURE:
<223> OTHER INFORMATION: Synthesized Parovirus B19 primer sequence

<400> SEQUENCE: 94
gatactcaac cccatggaga                                                  20

<210> SEQ ID NO 95
<211> LENGTH: 22
<212> TYPE: DNA
<213> ORGANISM: Unknown
<220> FEATURE:
<223> OTHER INFORMATION: Synthesized Parovirus B19 primer sequence

<400> SEQUENCE: 95
gccctaacac atatgggtac tt                                               22

<210> SEQ ID NO 96
<211> LENGTH: 23
<212> TYPE: DNA
<213> ORGANISM: Unknown
<220> FEATURE:
<223> OTHER INFORMATION: Synthesized human herpes primer sequence

<400> SEQUENCE: 96
taagatgtat gctgaagaac gtg                                              23

<210> SEQ ID NO 97
<211> LENGTH: 19
<212> TYPE: DNA
<213> ORGANISM: Unknown
<220> FEATURE:
<223> OTHER INFORMATION: Synthesized human herpes primer sequence

<400> SEQUENCE: 97
gcttgtcttc gtcgtttcg                                                   19

<210> SEQ ID NO 98
<211> LENGTH: 21
<212> TYPE: DNA
<213> ORGANISM: Unknown
<220> FEATURE:
<223> OTHER INFORMATION: Synthesized influenza A primer sequence

<400> SEQUENCE: 98
cttctaaccg aggtcgaaac g                                                21
```

-continued

```
<210> SEQ ID NO 99
<211> LENGTH: 25
<212> TYPE: DNA
<213> ORGANISM: Unknown
<220> FEATURE:
<223> OTHER INFORMATION: Synthesized influenza A primer sequence

<400> SEQUENCE: 99
agggcatttt ggacaaagtc gtcta                                          25

<210> SEQ ID NO 100
<211> LENGTH: 21
<212> TYPE: DNA
<213> ORGANISM: Unknown
<220> FEATURE:
<223> OTHER INFORMATION: Synthesized ABCCB-related hyperinsulinism
      primer sequence

<400> SEQUENCE: 100
cagctgagcc cgagcccaga c                                              21

<210> SEQ ID NO 101
<211> LENGTH: 23
<212> TYPE: DNA
<213> ORGANISM: Unknown
<220> FEATURE:
<223> OTHER INFORMATION: Synthesized ABCCB-related hyperinsulinism
      primer sequence

<400> SEQUENCE: 101
tcctccctcc ctgctctccc gtc                                            23

<210> SEQ ID NO 102
<211> LENGTH: 26
<212> TYPE: DNA
<213> ORGANISM: Unknown
<220> FEATURE:
<223> OTHER INFORMATION: Synthesized Alkaptonuria primer sequence

<400> SEQUENCE: 102
gggaattctg taaccggtta aataag                                         26

<210> SEQ ID NO 103
<211> LENGTH: 25
<212> TYPE: DNA
<213> ORGANISM: Unknown
<220> FEATURE:
<223> OTHER INFORMATION: Synthesized Alkaptonuria primer sequence

<400> SEQUENCE: 103
cttgctttaa ctcagccatt ttctc                                          25

<210> SEQ ID NO 104
<211> LENGTH: 22
<212> TYPE: DNA
<213> ORGANISM: Unknown
<220> FEATURE:
<223> OTHER INFORMATION: Synthesized Alpha-1 antitrypsin primer sequence

<400> SEQUENCE: 104
caccgtgaag gtgcctatga tg                                             22

<210> SEQ ID NO 105
<211> LENGTH: 22
<212> TYPE: DNA
<213> ORGANISM: Unknown
```

```
<220> FEATURE:
<223> OTHER INFORMATION: Synthesized Alpha-1 antitrypsin primer sequence

<400> SEQUENCE: 105
ggcattgccc aggtatttca tc                                              22

<210> SEQ ID NO 106
<211> LENGTH: 21
<212> TYPE: DNA
<213> ORGANISM: Unknown
<220> FEATURE:
<223> OTHER INFORMATION: Synthesized alpha-mannosidosis primer sequence

<400> SEQUENCE: 106
acgccagtgt cacctttagc c                                               21

<210> SEQ ID NO 107
<211> LENGTH: 20
<212> TYPE: DNA
<213> ORGANISM: Unknown
<220> FEATURE:
<223> OTHER INFORMATION: Synthesized alpha-mannosidosis primer sequence

<400> SEQUENCE: 107
gcacagccag acctcgcaat                                                 20

<210> SEQ ID NO 108
<211> LENGTH: 20
<212> TYPE: DNA
<213> ORGANISM: Unknown
<220> FEATURE:
<223> OTHER INFORMATION: Synthesized SLC12A6 primer sequence

<400> SEQUENCE: 108
tgaatcaaga aacccagact                                                 20

<210> SEQ ID NO 109
<211> LENGTH: 21
<212> TYPE: DNA
<213> ORGANISM: Unknown
<220> FEATURE:
<223> OTHER INFORMATION: Synthesized SLC12A6 primer sequence

<400> SEQUENCE: 109
attccatgtt ttcaccacta c                                               21

<210> SEQ ID NO 110
<211> LENGTH: 22
<212> TYPE: DNA
<213> ORGANISM: Unknown
<220> FEATURE:
<223> OTHER INFORMATION: Synthesized ARS1 primer sequence

<400> SEQUENCE: 110
cttttcccac gtggtggagt ag                                              22

<210> SEQ ID NO 111
<211> LENGTH: 21
<212> TYPE: DNA
<213> ORGANISM: Unknown
<220> FEATURE:
<223> OTHER INFORMATION: Synthesized ARS1 primer sequence

<400> SEQUENCE: 111
cccgcacaac aggtaaaaga c                                               21
```

<210> SEQ ID NO 112
<211> LENGTH: 18
<212> TYPE: DNA
<213> ORGANISM: Homo sapiens

<400> SEQUENCE: 112
ctgaaggccg aggccaag                                              18

<210> SEQ ID NO 113
<211> LENGTH: 19
<212> TYPE: DNA
<213> ORGANISM: Homo sapiens

<400> SEQUENCE: 113
cctcacggga cacaagcag                                             19

<210> SEQ ID NO 114
<211> LENGTH: 22
<212> TYPE: DNA
<213> ORGANISM: Homo sapiens

<400> SEQUENCE: 114
ggtagctgcg tggctaacgg ag                                         22

<210> SEQ ID NO 115
<211> LENGTH: 25
<212> TYPE: DNA
<213> ORGANISM: Homo sapiens

<400> SEQUENCE: 115
ccacatacat tatcatccac tgtag                                      25

<210> SEQ ID NO 116
<211> LENGTH: 25
<212> TYPE: DNA
<213> ORGANISM: Homo sapiens

<400> SEQUENCE: 116
gaaaggatca tttctcccctt gagtc                                     25

<210> SEQ ID NO 117
<211> LENGTH: 25
<212> TYPE: DNA
<213> ORGANISM: Homo sapiens

<400> SEQUENCE: 117
caggaacttg actccatagg gaaag                                      25

<210> SEQ ID NO 118
<211> LENGTH: 20
<212> TYPE: DNA
<213> ORGANISM: Homo sapiens

<400> SEQUENCE: 118
cctgtcttgc tttcctctcc                                            20

<210> SEQ ID NO 119
<211> LENGTH: 20
<212> TYPE: DNA
<213> ORGANISM: Homo sapiens

<400> SEQUENCE: 119
tcctcctctt tccccagaag                                            20

```
<210> SEQ ID NO 120
<211> LENGTH: 22
<212> TYPE: DNA
<213> ORGANISM: Homo sapiens

<400> SEQUENCE: 120
gccccattac attccagatt tg                                              22

<210> SEQ ID NO 121
<211> LENGTH: 20
<212> TYPE: DNA
<213> ORGANISM: Homo sapiens

<400> SEQUENCE: 121
ctcatacacg gcagccacat                                                 20

<210> SEQ ID NO 122
<211> LENGTH: 24
<212> TYPE: DNA
<213> ORGANISM: Homo sapiens

<400> SEQUENCE: 122
ctttcttttc gtaatatgcg gcct                                            24

<210> SEQ ID NO 123
<211> LENGTH: 25
<212> TYPE: DNA
<213> ORGANISM: Homo sapiens

<400> SEQUENCE: 123
tcctgagagg atcaagactg gaaac                                           25

<210> SEQ ID NO 124
<211> LENGTH: 20
<212> TYPE: DNA
<213> ORGANISM: Homo sapiens

<400> SEQUENCE: 124
gccacaatgc ctctgaaagc                                                 20

<210> SEQ ID NO 125
<211> LENGTH: 21
<212> TYPE: DNA
<213> ORGANISM: Homo sapiens

<400> SEQUENCE: 125
cttcatagca aggccaagaa c                                               21

<210> SEQ ID NO 126
<211> LENGTH: 21
<212> TYPE: DNA
<213> ORGANISM: Homo sapiens

<400> SEQUENCE: 126
cttcaaccct ccaggctaaa t                                               21

<210> SEQ ID NO 127
<211> LENGTH: 21
<212> TYPE: DNA
<213> ORGANISM: Homo sapiens

<400> SEQUENCE: 127
caaaactcgc cactgacaga a                                               21
```

```
<210> SEQ ID NO 128
<211> LENGTH: 19
<212> TYPE: DNA
<213> ORGANISM: Homo sapiens

<400> SEQUENCE: 128
tggcactggc tgtctcagg                                                   19

<210> SEQ ID NO 129
<211> LENGTH: 20
<212> TYPE: DNA
<213> ORGANISM: Homo sapiens

<400> SEQUENCE: 129
gacaggacag gttgcaggac                                                  20

<210> SEQ ID NO 130
<211> LENGTH: 22
<212> TYPE: DNA
<213> ORGANISM: Homo sapiens

<400> SEQUENCE: 130
cattctgtca cccttagaag cc                                               22

<210> SEQ ID NO 131
<211> LENGTH: 22
<212> TYPE: DNA
<213> ORGANISM: Homo sapiens

<400> SEQUENCE: 131
ggctatcaga gtccagattc cg                                               22

<210> SEQ ID NO 132
<211> LENGTH: 20
<212> TYPE: DNA
<213> ORGANISM: Homo sapiens

<400> SEQUENCE: 132
cgtacatacg tactgacgca                                                  20

<210> SEQ ID NO 133
<211> LENGTH: 19
<212> TYPE: DNA
<213> ORGANISM: Homo sapiens

<400> SEQUENCE: 133
taagcaacca cctgacagg                                                   19

<210> SEQ ID NO 134
<211> LENGTH: 25
<212> TYPE: DNA
<213> ORGANISM: Homo sapiens

<400> SEQUENCE: 134
gcatagcaga gtacctgaaa cagga                                            25

<210> SEQ ID NO 135
<211> LENGTH: 26
<212> TYPE: DNA
<213> ORGANISM: Homo sapiens

<400> SEQUENCE: 135
gacgtttgtc tcactaatga gtgaac                                           26
```

```
<210> SEQ ID NO 136
<211> LENGTH: 20
<212> TYPE: DNA
<213> ORGANISM: Homo sapiens

<400> SEQUENCE: 136
cagattgtct acagggagct                                              20

<210> SEQ ID NO 137
<211> LENGTH: 20
<212> TYPE: DNA
<213> ORGANISM: Homo sapiens

<400> SEQUENCE: 137
cttggcaaca aacagatcag                                              20

<210> SEQ ID NO 138
<211> LENGTH: 20
<212> TYPE: DNA
<213> ORGANISM: Homo sapiens

<400> SEQUENCE: 138
actacatttc ccaggattcc                                              20

<210> SEQ ID NO 139
<211> LENGTH: 20
<212> TYPE: DNA
<213> ORGANISM: Homo sapiens

<400> SEQUENCE: 139
tgcaggaaga gtaacaatcg                                              20

<210> SEQ ID NO 140
<211> LENGTH: 25
<212> TYPE: DNA
<213> ORGANISM: Homo sapiens

<400> SEQUENCE: 140
atgcctagac tcctgactac aacac                                        25

<210> SEQ ID NO 141
<211> LENGTH: 25
<212> TYPE: DNA
<213> ORGANISM: Homo sapiens

<400> SEQUENCE: 141
ctttgagtgg cagtgagaaa ataat                                        25

<210> SEQ ID NO 142
<211> LENGTH: 25
<212> TYPE: DNA
<213> ORGANISM: Homo sapiens

<400> SEQUENCE: 142
ctctcaaggt atatttctga catac                                        25

<210> SEQ ID NO 143
<211> LENGTH: 21
<212> TYPE: DNA
<213> ORGANISM: Homo sapiens

<400> SEQUENCE: 143
caaggcgtat ttgcttgaga g                                            21
```

```
<210> SEQ ID NO 144
<211> LENGTH: 19
<212> TYPE: DNA
<213> ORGANISM: Homo sapiens

<400> SEQUENCE: 144
gccagtgttt ttgcctgag                                               19

<210> SEQ ID NO 145
<211> LENGTH: 20
<212> TYPE: DNA
<213> ORGANISM: Homo sapiens

<400> SEQUENCE: 145
gactgctctc atagcatcgc                                              20

<210> SEQ ID NO 146
<211> LENGTH: 20
<212> TYPE: DNA
<213> ORGANISM: Homo sapiens

<400> SEQUENCE: 146
agttggcacc agctaaagat                                              20

<210> SEQ ID NO 147
<211> LENGTH: 20
<212> TYPE: DNA
<213> ORGANISM: Homo sapiens

<400> SEQUENCE: 147
tgtgaaccac agcagaatct                                              20

<210> SEQ ID NO 148
<211> LENGTH: 22
<212> TYPE: DNA
<213> ORGANISM: Homo sapiens

<400> SEQUENCE: 148
gtgaaggcac tgataaaaga gc                                           22

<210> SEQ ID NO 149
<211> LENGTH: 23
<212> TYPE: DNA
<213> ORGANISM: Homo sapiens

<400> SEQUENCE: 149
tggtagagtc cctgaagtca gaa                                          23

<210> SEQ ID NO 150
<211> LENGTH: 28
<212> TYPE: DNA
<213> ORGANISM: Homo sapiens

<400> SEQUENCE: 150
tcaggcgctc agctccgttt cggtttca                                     28

<210> SEQ ID NO 151
<211> LENGTH: 26
<212> TYPE: DNA
<213> ORGANISM: Homo sapiens

<400> SEQUENCE: 151
aagcgccatt ggagccccgc acttcc                                       26
```

```
<210> SEQ ID NO 152
<211> LENGTH: 20
<212> TYPE: DNA
<213> ORGANISM: Homo sapiens

<400> SEQUENCE: 152
agaggctggg gccaactgga                                              20

<210> SEQ ID NO 153
<211> LENGTH: 27
<212> TYPE: DNA
<213> ORGANISM: Homo sapiens

<400> SEQUENCE: 153
catactgcat gtgagagtct ggagacg                                      27

<210> SEQ ID NO 154
<211> LENGTH: 23
<212> TYPE: DNA
<213> ORGANISM: Homo sapiens

<400> SEQUENCE: 154
acccaggagc ccaagttccc ttt                                          23

<210> SEQ ID NO 155
<211> LENGTH: 20
<212> TYPE: DNA
<213> ORGANISM: Homo sapiens

<400> SEQUENCE: 155
acagatcagc atggctaaat                                              20

<210> SEQ ID NO 156
<211> LENGTH: 20
<212> TYPE: DNA
<213> ORGANISM: Homo sapiens

<400> SEQUENCE: 156
ttggtgtttg ctcaggaaga                                              20

<210> SEQ ID NO 157
<211> LENGTH: 20
<212> TYPE: DNA
<213> ORGANISM: Homo sapiens

<400> SEQUENCE: 157
ggcctacagg ggtttcaaat                                              20

<210> SEQ ID NO 158
<211> LENGTH: 18
<212> TYPE: DNA
<213> ORGANISM: Homo sapiens

<400> SEQUENCE: 158
caatagggcc ggcttgac                                                18

<210> SEQ ID NO 159
<211> LENGTH: 22
<212> TYPE: DNA
<213> ORGANISM: Homo sapiens

<400> SEQUENCE: 159
tgcaacaatt agttggaaaa gc                                           22
```

-continued

```
<210> SEQ ID NO 160
<211> LENGTH: 20
<212> TYPE: DNA
<213> ORGANISM: Homo sapiens

<400> SEQUENCE: 160
agtgtggggt cgggagtgtg                                               20

<210> SEQ ID NO 161
<211> LENGTH: 20
<212> TYPE: DNA
<213> ORGANISM: Homo sapiens

<400> SEQUENCE: 161
cgggcagctc tcggattctg                                               20

<210> SEQ ID NO 162
<211> LENGTH: 20
<212> TYPE: DNA
<213> ORGANISM: Homo sapiens

<400> SEQUENCE: 162
ccaaacccac ctctagcaaa                                               20

<210> SEQ ID NO 163
<211> LENGTH: 18
<212> TYPE: DNA
<213> ORGANISM: Homo sapiens

<400> SEQUENCE: 163
agagctgagg cggaatgg                                                 18

<210> SEQ ID NO 164
<211> LENGTH: 21
<212> TYPE: DNA
<213> ORGANISM: Homo sapiens

<400> SEQUENCE: 164
ctatgcctgg ttgcttagct g                                             21

<210> SEQ ID NO 165
<211> LENGTH: 22
<212> TYPE: DNA
<213> ORGANISM: Homo sapiens

<400> SEQUENCE: 165
cttcgttcta cccgaatcca tt                                            22

<210> SEQ ID NO 166
<211> LENGTH: 18
<212> TYPE: DNA
<213> ORGANISM: Homo sapiens

<400> SEQUENCE: 166
ctcaagcaca gtggattg                                                 18

<210> SEQ ID NO 167
<211> LENGTH: 19
<212> TYPE: DNA
<213> ORGANISM: Homo sapiens

<400> SEQUENCE: 167
gctctgaaga aaactctag                                                19
```

```
<210> SEQ ID NO 168
<211> LENGTH: 20
<212> TYPE: DNA
<213> ORGANISM: Homo sapiens

<400> SEQUENCE: 168
acggctgtca tcacttagac                                              20

<210> SEQ ID NO 169
<211> LENGTH: 20
<212> TYPE: DNA
<213> ORGANISM: Homo sapiens

<400> SEQUENCE: 169
ctccccttcc tatgacatga                                              20

<210> SEQ ID NO 170
<211> LENGTH: 21
<212> TYPE: DNA
<213> ORGANISM: Homo sapiens

<400> SEQUENCE: 170
aagcactgca gtaccttgga a                                            21

<210> SEQ ID NO 171
<211> LENGTH: 24
<212> TYPE: DNA
<213> ORGANISM: Homo sapiens

<400> SEQUENCE: 171
tcatgtagca tttaccacag ttga                                         24

<210> SEQ ID NO 172
<211> LENGTH: 10
<212> TYPE: DNA
<213> ORGANISM: Homo sapiens

<400> SEQUENCE: 172
tgcaagcgag                                                         10

<210> SEQ ID NO 173
<211> LENGTH: 11
<212> TYPE: DNA
<213> ORGANISM: Homo sapiens

<400> SEQUENCE: 173 caagcccttta t                                                      11

<210> SEQ ID NO 174
<211> LENGTH: 22
<212> TYPE: DNA
<213> ORGANISM: Homo sapiens

<400> SEQUENCE: 174
acctttgcag ggaatacagg gc                                           22

<210> SEQ ID NO 175
<211> LENGTH: 24
<212> TYPE: DNA
<213> ORGANISM: Homo sapiens

<400> SEQUENCE: 175
tgtcttcctc tctctaaggg gttc                                         24
```

```
<210> SEQ ID NO 176
<211> LENGTH: 20
<212> TYPE: DNA
<213> ORGANISM: Homo sapiens

<400> SEQUENCE: 176
cggagattta acggggacgt                                              20

<210> SEQ ID NO 177
<211> LENGTH: 20
<212> TYPE: DNA
<213> ORGANISM: Homo sapiens

<400> SEQUENCE: 177 tcgattttc caccccgcc                                                20

<210> SEQ ID NO 178
<211> LENGTH: 20
<212> TYPE: DNA
<213> ORGANISM: Homo sapiens

<400> SEQUENCE: 178
cctaggtttg tgatgcctct                                              20

<210> SEQ ID NO 179
<211> LENGTH: 20
<212> TYPE: DNA
<213> ORGANISM: Homo sapiens

<400> SEQUENCE: 179
taggttcaac tctctcctga                                              20

<210> SEQ ID NO 180
<211> LENGTH: 20
<212> TYPE: DNA
<213> ORGANISM: Homo sapiens

<400> SEQUENCE: 180
ccaggcaggg acccaagaat                                              20

<210> SEQ ID NO 181
<211> LENGTH: 20
<212> TYPE: DNA
<213> ORGANISM: Homo sapiens

<400> SEQUENCE: 181
ccactccgca ctgtccctct                                              20

<210> SEQ ID NO 182
<211> LENGTH: 16
<212> TYPE: DNA
<213> ORGANISM: Homo sapiens

<400> SEQUENCE: 182
acccaacccc tcccac                                                  16

<210> SEQ ID NO 183
<211> LENGTH: 17
<212> TYPE: DNA
<213> ORGANISM: Homo sapiens

<400> SEQUENCE: 183
agcttcagag accggag                                                 17
```

```
<210> SEQ ID NO 184
<211> LENGTH: 20
<212> TYPE: DNA
<213> ORGANISM: Homo sapiens

<400> SEQUENCE: 184
caaagaggtg ccctatggtg                                          20

<210> SEQ ID NO 185
<211> LENGTH: 19
<212> TYPE: DNA
<213> ORGANISM: Homo sapiens

<400> SEQUENCE: 185
caatcacgcg agctctctc                                           19

<210> SEQ ID NO 186
<211> LENGTH: 20
<212> TYPE: DNA
<213> ORGANISM: Homo sapiens

<400> SEQUENCE: 186
caccgttatc ccttaggtct                                          20

<210> SEQ ID NO 187
<211> LENGTH: 19
<212> TYPE: DNA
<213> ORGANISM: Homo sapiens

<400> SEQUENCE: 187
taggtcaagc tctgggaca                                           19

<210> SEQ ID NO 188
<211> LENGTH: 21
<212> TYPE: DNA
<213> ORGANISM: Homo sapiens

<400> SEQUENCE: 188
cctatatgga aaacaatgtg g                                        21

<210> SEQ ID NO 189
<211> LENGTH: 20
<212> TYPE: DNA
<213> ORGANISM: Homo sapiens

<400> SEQUENCE: 189
aaggagctaa catttcaggc                                          20

<210> SEQ ID NO 190
<211> LENGTH: 21
<212> TYPE: DNA
<213> ORGANISM: Homo sapiens

<400> SEQUENCE: 190
gcgcttctct cggctcctta g                                        21

<210> SEQ ID NO 191
<211> LENGTH: 19
<212> TYPE: DNA
<213> ORGANISM: Homo sapiens

<400> SEQUENCE: 191
ggctgcgctg ggtgtagtg                                           19
```

```
<210> SEQ ID NO 192
<211> LENGTH: 20
<212> TYPE: DNA
<213> ORGANISM: Homo sapiens

<400> SEQUENCE: 192
cttcccctgc aatttcattt                                              20

<210> SEQ ID NO 193
<211> LENGTH: 20
<212> TYPE: DNA
<213> ORGANISM: Homo sapiens

<400> SEQUENCE: 193
ccagggacct tcctagacaa                                              20

<210> SEQ ID NO 194
<211> LENGTH: 20
<212> TYPE: DNA
<213> ORGANISM: Homo sapiens

<400> SEQUENCE: 194
ccatgaccca ggagccattc                                              20

<210> SEQ ID NO 195
<211> LENGTH: 25
<212> TYPE: DNA
<213> ORGANISM: Homo sapiens

<400> SEQUENCE: 195
cgattacctc gacgactgag taaga                                        25

<210> SEQ ID NO 196
<211> LENGTH: 29
<212> TYPE: DNA
<213> ORGANISM: Homo sapiens

<400> SEQUENCE: 196
ggtacgtggg gctgcttgaa gagacgctg                                    29

<210> SEQ ID NO 197
<211> LENGTH: 32
<212> TYPE: DNA
<213> ORGANISM: Homo sapiens

<400> SEQUENCE: 197
gaagatctgg gtaggcagca ggtccaggga gc                                32

<210> SEQ ID NO 198
<211> LENGTH: 18
<212> TYPE: DNA
<213> ORGANISM: Homo sapiens

<400> SEQUENCE: 198
ccgaagcagg gagctttg                                                18

<210> SEQ ID NO 199
<211> LENGTH: 18
<212> TYPE: DNA
<213> ORGANISM: Homo sapiens

<400> SEQUENCE: 199
cggtgcatgc cttcacaa                                                18
```

-continued

<210> SEQ ID NO 200
<211> LENGTH: 18
<212> TYPE: DNA
<213> ORGANISM: Homo sapiens

<400> SEQUENCE: 200
ctacgcctgc ccgcactg                                           18

<210> SEQ ID NO 201
<211> LENGTH: 19
<212> TYPE: DNA
<213> ORGANISM: Homo sapiens

<400> SEQUENCE: 201
ccaaggacca cagggggaca                                          19

<210> SEQ ID NO 202
<211> LENGTH: 21
<212> TYPE: DNA
<213> ORGANISM: Homo sapiens

<400> SEQUENCE: 202
cattcacctc tgtgggtaag c                                       21

<210> SEQ ID NO 203
<211> LENGTH: 20
<212> TYPE: DNA
<213> ORGANISM: Homo sapiens

<400> SEQUENCE: 203
aggccttcac atttcacagc                                         20

<210> SEQ ID NO 204
<211> LENGTH: 20
<212> TYPE: DNA
<213> ORGANISM: Homo sapiens

<400> SEQUENCE: 204
agcattcctg atgccatgga                                         20

<210> SEQ ID NO 205
<211> LENGTH: 19
<212> TYPE: DNA
<213> ORGANISM: Homo sapiens

<400> SEQUENCE: 205
cttgcgaaag ccttccttg                                          19

<210> SEQ ID NO 206
<211> LENGTH: 25
<212> TYPE: DNA
<213> ORGANISM: Homo sapiens

<400> SEQUENCE: 206
ggctgtgtca ttttcttctc gctgg                                   25

<210> SEQ ID NO 207
<211> LENGTH: 23
<212> TYPE: DNA
<213> ORGANISM: Homo sapiens

<400> SEQUENCE: 207
tccaccaaac gtacccagac aag                                     23

<210> SEQ ID NO 208
<211> LENGTH: 24
<212> TYPE: DNA
<213> ORGANISM: Homo sapiens

<400> SEQUENCE: 208
tgtgtatgtg tctatcaact tatc                                          24

<210> SEQ ID NO 209
<211> LENGTH: 21
<212> TYPE: DNA
<213> ORGANISM: Homo sapiens

<400> SEQUENCE: 209
caaccccctt actggaaact a                                             21

<210> SEQ ID NO 210
<211> LENGTH: 34
<212> TYPE: DNA
<213> ORGANISM: Homo sapiens

<400> SEQUENCE: 210
catgtgaagc ttatgaatcc tgcgagcgat gggg                               34

<210> SEQ ID NO 211
<211> LENGTH: 32
<212> TYPE: DNA
<213> ORGANISM: Homo sapiens

<400> SEQUENCE: 211
accatggaat tcctatggcc tcttttccgc ag                                 32

<210> SEQ ID NO 212
<211> LENGTH: 16
<212> TYPE: DNA
<213> ORGANISM: Homo sapiens

<400> SEQUENCE: 212
cccctgcgtg gcagcc                                                   16

<210> SEQ ID NO 213
<211> LENGTH: 22
<212> TYPE: DNA
<213> ORGANISM: Homo sapiens

<400> SEQUENCE: 213
gtctttccca accgatccta tc                                            22

<210> SEQ ID NO 214
<211> LENGTH: 26
<212> TYPE: DNA
<213> ORGANISM: Homo sapiens

<400> SEQUENCE: 214
cgtgcgaaga tttgatgaac gaggtg                                        26

<210> SEQ ID NO 215
<211> LENGTH: 24
<212> TYPE: DNA
<213> ORGANISM: Homo sapiens

<400> SEQUENCE: 215
gcccttctgg gtagtctctg gatc                                          24

-continued

```
<210> SEQ ID NO 216
<211> LENGTH: 19
<212> TYPE: DNA
<213> ORGANISM: Homo sapiens

<400> SEQUENCE: 216
cactgcttaa ccaaatcac                                                   19

<210> SEQ ID NO 217
<211> LENGTH: 20
<212> TYPE: DNA
<213> ORGANISM: Homo sapiens

<400> SEQUENCE: 217
cagagcacag tgaaatttag                                                  20

<210> SEQ ID NO 218
<211> LENGTH: 30
<212> TYPE: DNA
<213> ORGANISM: Homo sapiens

<400> SEQUENCE: 218
ccggaattcg agacgcttca tctgaaggaa                                       30

<210> SEQ ID NO 219
<211> LENGTH: 31
<212> TYPE: DNA
<213> ORGANISM: Homo sapiens

<400> SEQUENCE: 219
cccaagcttc tgactcaaac acctgctgga t                                     31

<210> SEQ ID NO 220
<211> LENGTH: 19
<212> TYPE: DNA
<213> ORGANISM: Homo sapiens

<400> SEQUENCE: 220
ccagccgctg attgggaag                                                   19

<210> SEQ ID NO 221
<211> LENGTH: 19
<212> TYPE: DNA
<213> ORGANISM: Homo sapiens

<400> SEQUENCE: 221
gaactcagcc accatgtcc                                                   19

<210> SEQ ID NO 222
<211> LENGTH: 19
<212> TYPE: DNA
<213> ORGANISM: Homo sapiens

<400> SEQUENCE: 222
ggacggtctt gggtcgcct                                                   19

<210> SEQ ID NO 223
<211> LENGTH: 19
<212> TYPE: DNA
<213> ORGANISM: Homo sapiens

<400> SEQUENCE: 223
tgctccgggg tcgctatca                                                   19
```

```
<210> SEQ ID NO 224
<211> LENGTH: 22
<212> TYPE: DNA
<213> ORGANISM: Homo sapiens

<400> SEQUENCE: 224
ccgcagcaca agcacagata ag                                              22

<210> SEQ ID NO 225
<211> LENGTH: 19
<212> TYPE: DNA
<213> ORGANISM: Homo sapiens

<400> SEQUENCE: 225
cccccgagtg accccccact                                                 19

<210> SEQ ID NO 226
<211> LENGTH: 17
<212> TYPE: DNA
<213> ORGANISM: Homo sapiens

<400> SEQUENCE: 226
ggcacgagct gcccagg                                                    17

<210> SEQ ID NO 227
<211> LENGTH: 19
<212> TYPE: DNA
<213> ORGANISM: Homo sapiens

<400> SEQUENCE: 227
cccaaaactc caagcctgc                                                  19

<210> SEQ ID NO 228
<211> LENGTH: 23
<212> TYPE: DNA
<213> ORGANISM: Homo sapiens

<400> SEQUENCE: 228
gtcagagatt cagggacact tgg                                             23

<210> SEQ ID NO 229
<211> LENGTH: 19
<212> TYPE: DNA
<213> ORGANISM: Homo sapiens

<400> SEQUENCE: 229
atgctttcag cctcacacc                                                  19

<210> SEQ ID NO 230
<211> LENGTH: 29
<212> TYPE: DNA
<213> ORGANISM: Homo sapiens

<400> SEQUENCE: 230
cggtcgacgg gggaccctttt gtcatgaag                                      29

<210> SEQ ID NO 231
<211> LENGTH: 29
<212> TYPE: DNA
<213> ORGANISM: Homo sapiens

<400> SEQUENCE: 231
cgggatccca tttgatacca gcggttgtt                                       29
```

```
<210> SEQ ID NO 232
<211> LENGTH: 37
<212> TYPE: DNA
<213> ORGANISM: Homo sapiens

<400> SEQUENCE: 232
actgaatgtc agtgcagtcc aatttacagg ctggagc                              37

<210> SEQ ID NO 233
<211> LENGTH: 36
<212> TYPE: DNA
<213> ORGANISM: Homo sapiens

<400> SEQUENCE: 233
cctctgtccc atttgcaagc ttcagtaact gttccc                               36

<210> SEQ ID NO 234
<211> LENGTH: 20
<212> TYPE: DNA
<213> ORGANISM: Homo sapiens

<400> SEQUENCE: 234
tggaaccaga tgtaccagca                                                 20

<210> SEQ ID NO 235
<211> LENGTH: 20
<212> TYPE: DNA
<213> ORGANISM: Homo sapiens

<400> SEQUENCE: 235
gggaagaggg actgatttgc                                                 20

<210> SEQ ID NO 236
<211> LENGTH: 20
<212> TYPE: DNA
<213> ORGANISM: Homo sapiens

<400> SEQUENCE: 236
acgtagggct taatagtggg                                                 20

<210> SEQ ID NO 237
<211> LENGTH: 20
<212> TYPE: DNA
<213> ORGANISM: Homo sapiens

<400> SEQUENCE: 237
gtttaatgct caaacgctcc                                                 20

<210> SEQ ID NO 238
<211> LENGTH: 30
<212> TYPE: DNA
<213> ORGANISM: Homo sapiens

<400> SEQUENCE: 238
aatctcattt atatgtactt acatgccagt                                      30

<210> SEQ ID NO 239
<211> LENGTH: 29
<212> TYPE: DNA
<213> ORGANISM: Homo sapiens

<400> SEQUENCE: 239
ggttcatatt cataccaaag aatgacatc                                       29
```

-continued

<210> SEQ ID NO 240
<211> LENGTH: 20
<212> TYPE: DNA
<213> ORGANISM: Homo sapiens

<400> SEQUENCE: 240
gctgctgggc cagggctgtg                                              20

<210> SEQ ID NO 241
<211> LENGTH: 20
<212> TYPE: DNA
<213> ORGANISM: Homo sapiens

<400> SEQUENCE: 241
gcagaggcag ctggcaccag                                              20

<210> SEQ ID NO 242
<211> LENGTH: 19
<212> TYPE: DNA
<213> ORGANISM: Homo sapiens

<400> SEQUENCE: 242
gccggcagag cggcggtac                                               19

<210> SEQ ID NO 243
<211> LENGTH: 18
<212> TYPE: DNA
<213> ORGANISM: Homo sapiens

<400> SEQUENCE: 243
ctggctcccg cgccttcc                                                18

<210> SEQ ID NO 244
<211> LENGTH: 20
<212> TYPE: DNA
<213> ORGANISM: Homo sapiens

<400> SEQUENCE: 244
tggctggatt ttgtacttac                                              20

<210> SEQ ID NO 245
<211> LENGTH: 20
<212> TYPE: DNA
<213> ORGANISM: Homo sapiens

<400> SEQUENCE: 245
accagaaagc aggatttagt                                              20

<210> SEQ ID NO 246
<211> LENGTH: 22
<212> TYPE: DNA
<213> ORGANISM: Homo sapiens

<400> SEQUENCE: 246
cataccacag gggcatcctc ac                                           22

<210> SEQ ID NO 247
<211> LENGTH: 22
<212> TYPE: DNA
<213> ORGANISM: Homo sapiens

<400> SEQUENCE: 247
cagagcaggt gcgtgaggtg ct                                           22

```
<210> SEQ ID NO 248
<211> LENGTH: 20
<212> TYPE: DNA
<213> ORGANISM: Homo sapiens

<400> SEQUENCE: 248
gctgactctg ccagtgcctg                                            20

<210> SEQ ID NO 249
<211> LENGTH: 20
<212> TYPE: DNA
<213> ORGANISM: Homo sapiens

<400> SEQUENCE: 249
cagggccatc acaggtcccc                                            20

<210> SEQ ID NO 250
<211> LENGTH: 24
<212> TYPE: DNA
<213> ORGANISM: Homo sapiens

<400> SEQUENCE: 250
tggctatttt tacctccttt gttt                                       24

<210> SEQ ID NO 251
<211> LENGTH: 20
<212> TYPE: DNA
<213> ORGANISM: Homo sapiens

<400> SEQUENCE: 251
agttccagat ggatcccaga                                            20

<210> SEQ ID NO 252
<211> LENGTH: 20
<212> TYPE: DNA
<213> ORGANISM: Homo sapiens

<400> SEQUENCE: 252
agaacccctg actccttaga                                            20

<210> SEQ ID NO 253
<211> LENGTH: 18
<212> TYPE: DNA
<213> ORGANISM: Homo sapiens

<400> SEQUENCE: 253
gagggagagg cattcaaa                                              18

<210> SEQ ID NO 254
<211> LENGTH: 20
<212> TYPE: DNA
<213> ORGANISM: Homo sapiens

<400> SEQUENCE: 254
ttgtcttttg ggctgtagca                                            20

<210> SEQ ID NO 255
<211> LENGTH: 26
<212> TYPE: DNA
<213> ORGANISM: Homo sapiens

<400> SEQUENCE: 255
tcatgacaga gatcattgta ctgaaa                                     26
```

```
<210> SEQ ID NO 256
<211> LENGTH: 29
<212> TYPE: DNA
<213> ORGANISM: Homo sapiens

<400> SEQUENCE: 256
tcccattgct cacaaaggtc ttgttttg                                29

<210> SEQ ID NO 257
<211> LENGTH: 20
<212> TYPE: DNA
<213> ORGANISM: Homo sapiens

<400> SEQUENCE: 257
attcctcgca acactgggaa                                         20

<210> SEQ ID NO 258
<211> LENGTH: 18
<212> TYPE: DNA
<213> ORGANISM: Homo sapiens

<400> SEQUENCE: 258
gacgccagag ctgggtca                                           18

<210> SEQ ID NO 259
<211> LENGTH: 18
<212> TYPE: DNA
<213> ORGANISM: Homo sapiens

<400> SEQUENCE: 259
ctgcccaccg tccctctt                                           18

<210> SEQ ID NO 260
<211> LENGTH: 20
<212> TYPE: DNA
<213> ORGANISM: Homo sapiens

<400> SEQUENCE: 260
tgcctgtgac actgaactcc                                         20

<210> SEQ ID NO 261
<211> LENGTH: 20
<212> TYPE: DNA
<213> ORGANISM: Homo sapiens

<400> SEQUENCE: 261
tcctgaggca gaacttcacc                                         20

<210> SEQ ID NO 262
<211> LENGTH: 21
<212> TYPE: DNA
<213> ORGANISM: Homo sapiens

<400> SEQUENCE: 262
aaagcagatg ggtttgtttt g                                       21

<210> SEQ ID NO 263
<211> LENGTH: 18
<212> TYPE: DNA
<213> ORGANISM: Homo sapiens

<400> SEQUENCE: 263
ggccacgctg gtagagag                                           18
```

-continued

```
<210> SEQ ID NO 264
<211> LENGTH: 10
<212> TYPE: DNA
<213> ORGANISM: Unknown
<220> FEATURE:
<223> OTHER INFORMATION: Synthetic microbiome 16s primer sequence

<400> SEQUENCE: 264 gtgccagcmg                                                              10

<210> SEQ ID NO 265
<211> LENGTH: 10
<212> TYPE: DNA
<213> ORGANISM: Unknown
<220> FEATURE:
<223> OTHER INFORMATION: Synthetic microbiome 16s primer sequence

<400> SEQUENCE: 265 ggactachvg                                                              10

<210> SEQ ID NO 266
<211> LENGTH: 17
<212> TYPE: DNA
<213> ORGANISM: Unknown
<220> FEATURE:
<223> OTHER INFORMATION: Synthetic microbiome transposase sequence

<400> SEQUENCE: 266
tcgtcggcag cgtcaga                                                      17

<210> SEQ ID NO 267
<211> LENGTH: 17
<212> TYPE: DNA
<213> ORGANISM: Unknown
<220> FEATURE:
<223> OTHER INFORMATION: Synthetic microbiome transposase sequence

<400> SEQUENCE: 267
gtctcgtggg ctcggag                                                      17

<210> SEQ ID NO 268
<211> LENGTH: 14
<212> TYPE: DNA
<213> ORGANISM: Unknown
<220> FEATURE:
<223> OTHER INFORMATION: Synthetic microbiome forward index sequence

<400> SEQUENCE: 268
aatgatacgg cgac                                                         14

<210> SEQ ID NO 269
<211> LENGTH: 14
<212> TYPE: DNA
<213> ORGANISM: Unknown
<220> FEATURE:
<223> OTHER INFORMATION: Synthetic microbiome forward index sequence

<400> SEQUENCE: 269
caagcagaag acgg                                                         14
```